(12) United States Patent
Grant et al.

(10) Patent No.: US 6,657,104 B1
(45) Date of Patent: Dec. 2, 2003

(54) TRANSGENIC MOUSE MODEL FOR CARDIAC HYPERTROPHY AND METHODS OF USE THEREOF

(75) Inventors: Stephen R. Grant, Ft. Worth; Eric N. Olson, Dallas, both of TX (US); Jeffrey D. Molkentin, Cincinnati, OH (US)

(73) Assignees: Texas Systems, University of the Board of the Regents, Austin, TX (US); University of North Texas Health Science Center, Fort Worth, TX (US)

( * ) Notice: Subject to any disclaimer, the term of this patent is extended or adjusted under 35 U.S.C. 154(b) by 0 days.

(21) Appl. No.: 09/173,799

(22) Filed: Oct. 15, 1998

Related U.S. Application Data

(63) Continuation of application No. 09/061,417, filed on Apr. 16, 1998.
(60) Provisional application No. 60/081,853, filed on Apr. 15, 1998, provisional application No. 60/065,178, filed on Nov. 10, 1997, and provisional application No. 60/062,864, filed on Oct. 16, 1997.

(51) Int. Cl.$^7$ .................. C12N 15/85; C12N 15/86; C12N 15/00
(52) U.S. Cl. .................. 800/18; 435/325; 435/352; 435/354; 800/3; 800/25; 800/14; 800/13; 800/9
(58) Field of Search .............. 800/3, 13, 14, 800/18, 25, 22; 435/325

(56) References Cited

U.S. PATENT DOCUMENTS

| | | |
|---|---|---|
| 5,093,246 A | 3/1992 | Cech et al. ............... 435/6 |
| 5,284,826 A | 2/1994 | Eberle .................... 514/11 |
| 5,493,019 A | 2/1996 | Bulusu .................. 540/456 |
| 5,525,590 A | 6/1996 | Bollinger et al. .......... 514/11 |
| 5,530,120 A | 6/1996 | Luly et al. .............. 540/456 |
| 5,604,251 A | 2/1997 | Heitsch et al. .......... 514/396 |
| 5,641,745 A | 6/1997 | Ramtoola ................ 514/11 |
| 5,739,105 A | 4/1998 | Kim et al. ............... 514/11 |

FOREIGN PATENT DOCUMENTS

| | | |
|---|---|---|
| GB | 2257359 | 1/1993 |
| WO | WO 93/20218 | 10/1993 |
| WO | WO 93/23569 | 11/1993 |
| WO | WO 94/29442 A3 | 12/1994 |
| WO | WO 94/29442 A2 | 12/1994 |
| WO | WO 95/34285 | 12/1995 |
| WO | WO 96/01313 | 1/1996 |
| WO | WO 96/40892 | 12/1996 |
| WO | WO 97/07787 | 3/1997 |
| WO | WO 97/40163 | 10/1997 |
| WO | WO 98/27098 | 6/1998 |
| WO | WO 98/33791 | 8/1998 |

OTHER PUBLICATIONS

Hammer et al. Spontaneous inflammatory disease in transgenic rats expressing HLA–B27 and human b2m: An animal model of HLA–B27–associated human disorders. Cell 63: 1099–1112, Nov. 1990.*

Mullins et al. Fulminant hypertension in transgenic rats harbouring the mouse Ren–2 gene. Nature 344: 541–544, Apr. 1990.*

Mullins et al. Expression of the DBA/2J Ren–2 gene in the adrenal gland of transgenic mice. EMBO J. 8(13): 4065–4072, 1989.*

Taurog et al. HLA–B27 in inbred and non–inbred transgenic mice. J. Immunol. 141: 4020–4023, Dec. 1988.*

Wall, RJ Transgenic livestock: Progress and prospects for the future. Theriogenology 45: 57–68, 1996.*

Ausubel et al., eds., *Current Protocols in Molecular Biology*, vols. 1,2, and 3, John Wiley and Sons, Inc. (1987) Title page and table of contents only.

Bunn and Poyton, "Oxygen sensing and molecular adaptation to hypoxia" *Physiol. Rev.* 76(3):839–885 (1996).

Bustamante et al., "Stretch–activated channels in heart cells: Relevance to cardiac hypertrophy" *J. Cardiovasc. Pharmacol.* 17(Suppl. 2):S110–S113 (1991).

Chen and Schwartz, "Recruitment of the Tinman Homolog Nkx–2.5 by serum response factor activates cardiac α–actin gene transcription", *Mol. Cell. Biol.* 16(11):6372–6384 (1996).

Chien, et al., "Transcriptional regulation during cardiac growth and development" *Annual Rev. Physiol.* 55:77–95 (1993).

Chomczynski and Sacchi, "Single–step method of RNA isolation by acid guanidinium thiocyanate–phenol–chloroform extraction" *Anal. Biochem.* 162:156–159 (1987).

Coligan, J.E. et al., eds., *Current Protocols in Immunology* (1991) Title page and table of contents only.

Crooke, S.T. and Lebleu, B. eds., *Antisense Research and Applications* CRC Press (1993) Title page and table of contents only.

Cruzalegui and Means, "Biochemical characterization of the multifunctional $Ca^{2+}$/Calmodulin–dependent protein kinase type IV expressed in insect cells" *J. Biol. Chem.* 268(35):26171–26178 (1993).

(List continued on next page.)

Primary Examiner—Deborah J. R. Clark
Assistant Examiner—Anne-Marie Baker
(74) Attorney, Agent, or Firm—Fulbright & Jaworski

(57) ABSTRACT

Transgene constructs for generating transgenic animals, wherein the transgene encodes a gene product which modulates transcription of a hypertrophy-sensitive gene, are provided. Further provided are recombinant vectors comprising the transgenes of the invention. Further provided are transgenic animals generated using the transgene constructs. Further provided are enzyme-based, cell-based, and whole-animal-based assays for detecting substances having therapeutic activity toward cardiac hypertrophy. Further provided are compositions comprising substances which modulate levels of active product of a hypertrophy-sensitive gene. Further provided are methods of treating cardiac hypertrophy.

19 Claims, 23 Drawing Sheets

(4 of 23 Drawing Sheet(s) Filed in Color)

OTHER PUBLICATIONS

Dachs and Stratford, "The molecular response of mammalian cells to hypoxia and the potential for exploitation in cancer therapy", *Br. J. Cancer* 74:S125–S132 (1996).

Faller and Baltimore, "Liposome encapsulation of retrovirus allows efficient superinfection of resistant cell lines" *J. Virol.* 49(1):269–272 (1984).

Farrance et al., "M–CAT binding factor is related to the SV40 enhancer binding factor, TEF–1" *J. Biol. Chem.* 267(24):17234–17240 (1992).

Fields and Song, "A novel genetic system to detect protein–protein interactions" *Nature* 340:245–246 (1989).

Firth et al., "Oxygen–regulated control elements in the phosphoglycerate kinase 1 and lactate dehydrogenase A genes: Similarities with the erythropoitein 3' enhancer" *Proc. Natl. Acad. Sci. USA* 91:6496–6500 (1994).

Flanagan et al., "Nuclear association of a T–cell transcription factor blocked by FK–506 and cyclosporin A" *Nature* 352:803–807 (1991).

Force et al., "Stress–activated protein kinases in cardiovascular disease" *Circ. Res.* 78(6):947–953 (1996).

Franz et al., "Analysis of tissue–specific gene delivery by recombinant adenoviruses containing cardiac–specific promoters" *Cardiovasc. Res.* 35:560–566 (1997).

Freshney, R.I. ed., *Animal Cell Culture,* IRL Press (1987) Title page and table of contents only.

Gait, M.J. ed., *Oligonucleotide Synthesis,* IRL Press (1984) Title page and table of contents only.

Gennaro, ed., *Remington: The Science and Practice of Pharmacy,* 19th edition (1995) Title page and table of contents only.

Gossen and Bujard, "Tight control of gene expression in mammalian cells by tetracycline–responsive promoters" *Proc. Natl. Acad. Sci. USA* 89:5547–5551 (1992).

Gossen, http://www.zmbh.uni–heidelberg.de/bujard/reporter/pUHD10–3.html, (Dec. 23, 1998) 5 pages.

Gruver et al., "Targeted developmental overexpression of calmodulin induces proliferative and hypertrophic growth of cardiomyocytes in transgenic mice" *Endocrinology* 133(1):376–388 (1993).

Guillemin and Krasnow, "The hypoxic response: Huffing and HIFing" *Cell* 89(1):9–12 (1997).

Hansen et al., "Re–examination and further development of a precise and rapid dye method for measuring cell growth/cell kill"*J. Immunol. Method.* 119:203–210 (1989).

Harlow et al., *Antibodies: A Laboratory Manual* (Cold Spring Harbor, NY) (1988) Title page and table of contents only.

Hasegawa et al., "cis–acting sequences that mediate induction of β–myosin heavy chain gene expression during left ventricular hypertrophy due to aortic constriction" *Circulation* 96(11):3943–3953 (1997).

Heim and Tsien, "Engineering green fluorescent protein for improved brightness, loner wavelengths and fluorescence resonance energy transfer" *Curr. Biol.* 6(2):178–182 (1996).

Herzig et al., "Angiotensin II type$_{Ia}$ receptor gene expression in the heart: AP-1 and ATAT-4 participate in the response to pressure overload" *Proc. Natl. Acad. Sci. USA* 94:7543–7548 (1997).

Hillen and Wissmann, "Tet repressor–tet operator interaction" *Protein–Nucleic Acid Interaction,* Saenger and Heinemann, eds., CRC Press, Inc., pp. 143–162 (1989).

Hodgson and Solaiman, "Virosomes: Cationic liposomes enhance retroviral transduction" *Nature Biotechnol.* 14(3):339–342 (1996).

Hogan et al., *Manipulating the Mouse Embryo—A Laboratory Manual* (Cold Spring Harbor Laboratory, Cold Spring Harbor, NY) (1986).

Hongo et al., "Effect of stretch on contraction and the $Ca^{2+}$ transient in ferrent ventricular muscles during hypoxia and acidosis" *Am.J. Physiol.* 269(3):C690–C697 (1995).

Hunter et al., "Targeting gene expression to specific cardiovascular cell types in transgenic mice" *Hypertension* 22(4):608–617 (1993).

Jakoby, ed., *Methods in Enzymology,* Academic Press, Inc. (1979) Title page and table of contents only.

Jiang et al., "V–SRC induces expression of hypoxia–inducible factor 1 (HIF–1) and transcription of genes encoding vascular endothelial growth factor and enolase 1: Involvement of HIF–1 in tumor progression" *Cancer Res.* 57:5328–5335 (1997).

Johnstone and Thorpe, eds., *Immunochemistry in Practice,* 3rd edition, Blackwell Science (1996) p. 69.

Jones et al., "Ablation of the murine = myosin heavy chain gene leads to dosage effects and functional deficits in the heart" *J. Clin. Invest.* 98(8):1906–1917 (1996).

Jones et al., "Murine pulmonary myocardium: Developmental analysis of cardiac gene expression" *Dev. Dyn.* 200:117–128 (1994).

Kariya et al., "An enhancer core element mediates stimulation of the rat β–myosin heavy chain promoter by an $\alpha_1$–adrenergic agonist and activated β–protein kinase C in hypertrophy of cardiac myocytes" *J. Biol. Chem.* 269(5):3775–3782 (1994).

Karliner et al., "Effects of pertussis toxin on $\alpha_1$–agonist–mediated phosphatidylinositide turnover and myocardial cell hypertrohy in neonatal rat ventricular myocytes" *Experientia* 46:81–84 (1990).

Karns et al., "M–CAT, CArG, and Sp1 elements are required for $\alpha_1$–adrenergic induction of the skeletal α–actin promoter during cardiac myocyte hypertrophy" *J.Biol. Chem.* 270(1):410–417 (1995).

Kikura and Levy, "New cardiac drugs" *Int. Anesthesiol. Clin.* 33(1):21–37 (1995).

Kincaid et al., "Cloning and characterization of molecular isoforms of the catalytic subunit of calcineurin using nonisotopic methods" *Biol. Chem.* 265(19):11312–11319 (1990).

Komuro and Yazaki, "Control of cardiac gene expression by mechanical stress" *Annu. Rev. Physiol.* 55:55–75 (1993).

Kovacic–Milivojevic et al., "Selective regulation of the atrial natriureteic peptide gene by individual components of the activator protein–1 complex" *Endocrinol.* 137(3):1108–1117 (1996).

LaPointe et al., "Tissue–specific expression of the human brain natriuretic peptide gene in cardiac myocytes" *Hypertension* 27(3):715–722 (1996).

Leite et al., "Regulation of ANP secretion by endothelin–1 in cultured atrial myocytes: desensitization and receptor subtype" *Am. J. Physiol.* 267(6):H2193–H2203 (1994).

Linn et al., "Conservation of an AE3 $Cl^-/HCO_3^-$ exchanger cardiac–specific exon and promoter region and AE3 mRNA expression patterns in murine and human hearts" *Circ. Res.* 76:584–591 (1995).

Loh et al., "Calcineurin binds the transcription factor NFAT1 and reversibly regulates its activity" *J. Biol. Chem.* 271(18):10884–10891 (1996).

Loh et al., "T–cell receptor stimulation elicits an early phase of activation and a later phase of deactivation of the transcription factor NFAT1" *Mol. Cell Biol.* 16(7):3945–3954 (1996).

MacLellan et al., "Transforming growth factor–β response elements of the skeleta α–actin gene" *J. Biol. Chem.*, 269(24):16754–16760 (1994).

Mar and Ordahl, "M–CAT binding factor, a novel trans–acting factor governing muscle–specific transcription" *Mol. Cell Biol.* 10(8):4271–4283 (1990).

Marban et al., "Intracellular free calcium concentration measured with $^{19}F$ NMR spectroscopy in intact ferret hearts" *Proc. Natl. Acad. Sci. USA* 84:6005–6009 (1987).

McBride et al., "fos/jun repression of cardiac–specific transcription in quiescent and growth–stimulated myocytes is targeted at a tissue–specific cis element" *Mol. Cell. Biol.* 13(1):600–612 (1993).

Melton, D.A., ed. *Antisense RNA and DNA,* Cold Spring Harbor Laboratory, Cold Spring Harbor, NY (1988) Title page and table of contents only.

Mercadier et al., "Altered sarcoplasmic reticulum $Ca^{2+}$–ATPase gene expression in the human ventricle during end–stage heart failure" *J. Clin. Invest.* 85:305–309 (1990).

Miller, J.M. and Calos, M.P., eds., *Gene Transfer Vectors for Mammalian Cells* (1987) Title page and table of contents only.

Mitra et al., "Fluorescence resonance energy transfer between blue–emitting and red–shifted excitation derivatives of the green fluorescent protein" *Gene* 173:13–17 (1996).

Molkentin and Olson, "GATA4: A Novel transcriptional regulator of cardiac hypertrophy?" *Circulation* 96(11):3833–3835 (1997).

Molkentin et al., "A Calcineurin–dependent transcriptional pathway for cardiac hypertrophy" *Cell* 93:215–228 (1998).

Mullis et al., eds., *PCR: The Polymerase Chain Reaction* (1994) Title page and table of contents only.

Muramatsu and Kincaid, "Molecular cloning and chromosomal mapping of the human gene for the testis–specific catalytic subunit of calmodulin–dependent protein phosphatase (calcineurin A)" *Biochem. Biophys. Res. Comm.* 188(1):265–271 (1992).

Naldini et al., "In vivo gene delivery and stable transduction of nondividing cells by a lentiviral vector" *Science* 272:263–267 (1996).

O'Keefe et al., "FK–506– and CsA–sensitive activation of the interleukin-2 promoter by calcineurin" *Nature* 357:692–694 (1992).

Palmiter et al., "Dramatic growth of mice that devleop from eggs microinjected with metallothionein–growth hormone fusion genes" *Nature* 300:611–615 (1982).

Parmacek et al., "A novel myogenic regulatory circuit controls slow/cardiac troponin C gene transcription in skeletal muscle" *Mol. Cell. Biol.* 14(3):1870–1885 (1994).

Parsons et al., "Regulation of calcineurin phosphatase activity and interaction with the FK–506•FK–506 binding protein complex" *JBC* 269(30):19610–19616 (1994).

Rao et al., "Transcription factors of the NFAT family: Regulation and function" *Ann. Rev. Immunol.* 15:707–747 (1997).

Robbins et al., "In vivo definition of a cardiac specific promoter and its potential utility in remodeling the heart" *Ann. N.Y. Acad. Sci.* 752:492–505 (1995).

Sadoshima and Izumo, "Signal transduction pathways of angiotensin II–induced c–fos gene expression in cardiac myocytes in vitro" *Circ. Res.* 73:424–438 (1993).

Sadoshima and Izumo, "The cellular and molecular response of cardiac myocytes to mechanical stress" *Annual Rev. Physiol.* 59:551–571 (1997).

Sadoshima et al., "Autocrine release of angiotensin II mediates stretch–induced hypertrophy of cardiac myocytes in vitro" *Cell* 75:977–984 (1993).

Sambrook, et al., *Molecular Cloning: A Laboratory Manual* (Cold Spring Harbor Laboratory, Cold Spring Harbor, NY) (1989) Title page and table of contents only.

Sartorelli et al., "Myocardial activation of the human cardiac α–actin promoter by helix–loop–helix proteins" *Proc. Natl. Acad. Sci. USA* 89:4047–4051 (1992).

Schwinger et al., "Unchanged protein levels of SERCA II and phospholamban but reduced $Ca^{2+}$ uptake and $Ca^{2+}$–ATPase activity of cardiac sarcoplasmic reticulum from dilated cardiomyopathy patients compared with patients with nonfailing hearts" *Circulation* 92(11):3220–3228 (1995).

Scopes, R., *Protein Purification: Principles and Practice,* Springer–Verlag (1987) Title page and table of contents only.

Sei et al., "The α–adrenergic stimulation of atrial natriuretic factor expression in cardiac myocytes requires calcium influx, protein kinase C, and calmodulin–regulated pathways" *J. Biol. Chem.* 266(24):15910–15916 (1991).

Shaw et al., "Immunosuppressive drugs prevent a rapid dephosphorylation of transcription factor NFAT1 in stimulated immune cells" *Proc. Natl. Acad. Sci. USA* 92: 11205–11209 (1995).

Shi et al., "Transcriptional repression by YY1, a human GLI–Krüppel–related protein, and relief of repression by adenovirus E1A protein" *Cell* 67:377–388 (1991).

Sun et al., "Differential activation of CREB by $Ca^{2+}$/calmodulin–dependent protein kinases type II and type IV involves phosphorylation of a site that negatively regulates activity" *Genes Dev.* 8:2527–2539 (1994).

Thorburn et al., "HRas–dependent pathways can activate morphological and genetic markers of cardiac muscle cell hypertrophy" *J. Biol. Chem.* 268(3):2244–2249 (1993).

Thuerauf and Glembotski, "Differential effects of protein kinase C, Ras, and Raf–1 kinase on the induction of the cardiac B–type natriuretic peptide gene through a critical promoter–proximal M–CAT element" *J. Biol. Chem.* 272(11):7464–7472 (1997).

VanBerkum et al., "Calmodulin activation of target enzymes" *J. Biol. Chem.* 265(7):3750–3756 (1990).

Verma and Somia, "Gene therapy–promises, problems and prospects" *Nature* 389:239–242 (1997).

Wang et al., "Molecular cloning and characterization of a novel p38 mitogen–activated protein kinase" *J. Biol. Chem.* 272(38):23668–23674 (1997).

Weir, D.M. et al., eds., *Handbook of Experimental Immunology,* vols. 1–4 (1986) Title page and table of contents only.

Wilson et al., "Biological properties of poliovirus encapsulated in lipid vesicles: Antibody resistance and infectivity in virus–resistant cells" *Proc. Natl. Acad. Sci. USA* 74(8):3471–3475 (1997).

Woods and Ellis, *Laboratory Histopathology: A Complete Reference,* Churchill Livingstone Publishers, pp. 7.1–13 (1994)

Yamazaki et al., "Endothelin–1 is involved in mechanical stress–induced cardiomyocyte hypertrophy" *J. Biol. Chem.* 271(6):3221–3228 (1996).

Yang et al., "Optimized codon usage and chromophore mutations provide enhanced sensitivity with the green fluorescent protein" *Nucl. Acids. Res.* 24(22):4592–4593 (1996).

Yu et al., "Conditional transgene expression in the heart" *Circ. Res.* 79(4):691–697 (1996).

Zou et al., "Protein kinase C, but not tyrosine kinases or ras, plays a critical role in antiotensin II–induced activation of raf–1 kinase and extracellular signal–regulated proein kinases in cardiac myocytes" *J. Biol. Chem.* 271(52):33592–33597 (1996).

\* cited by examiner

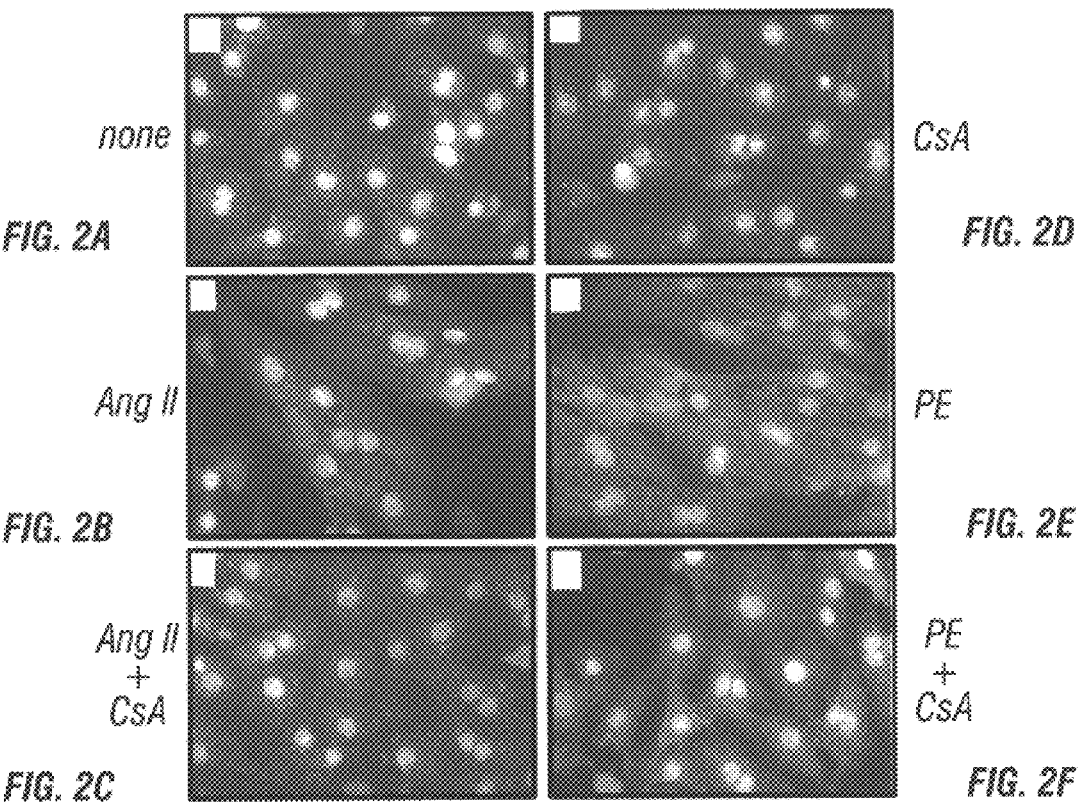
FIG. 2A none
FIG. 2B Ang II
FIG. 2C Ang II + CsA
FIG. 2D CsA
FIG. 2E PE
FIG. 2F PE + CsA

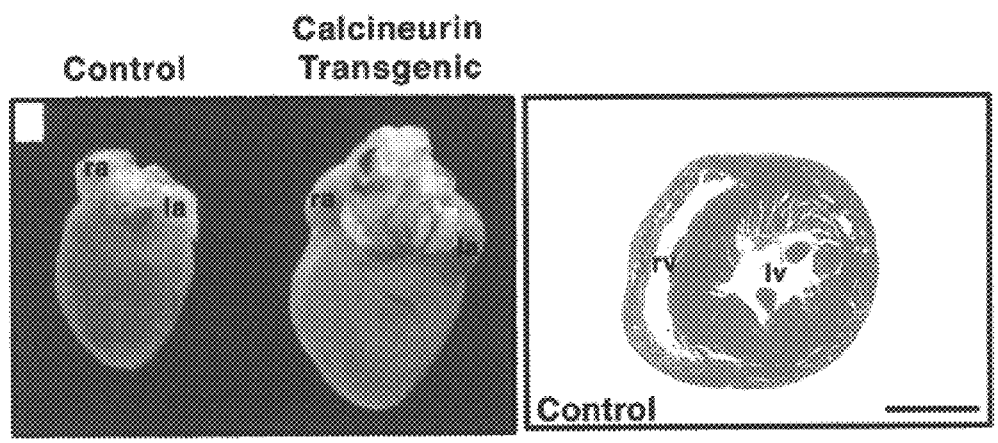
FIG. 3A  FIG. 3F
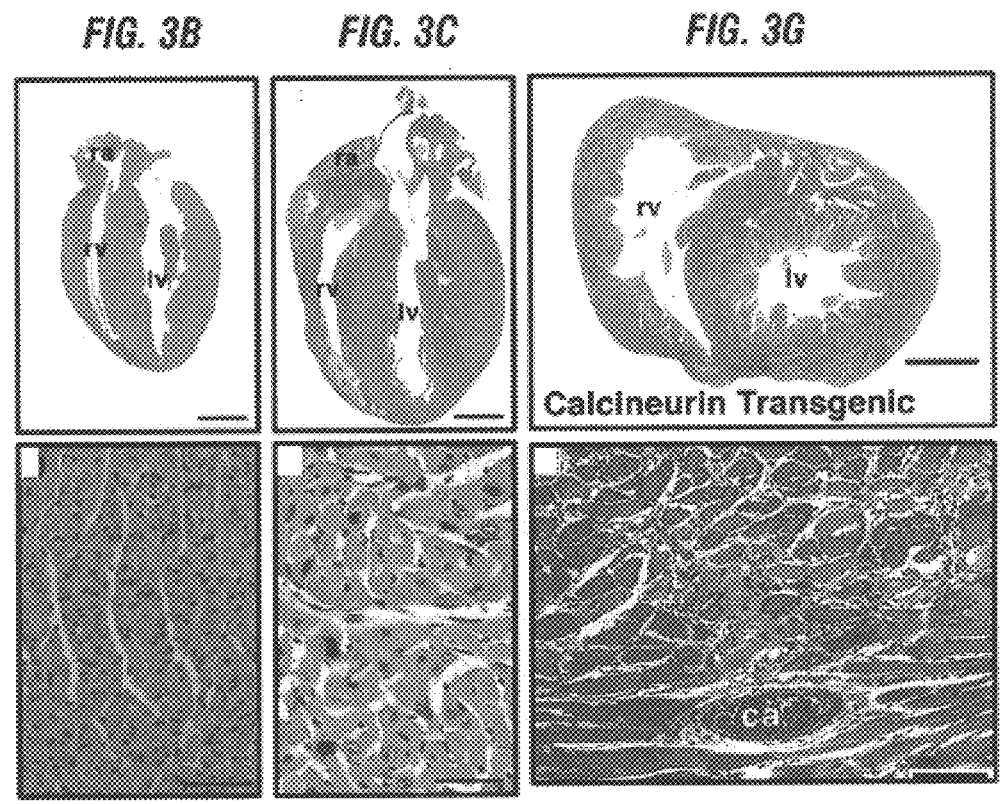
FIG. 3B  FIG. 3C  FIG. 3G
FIG. 3D  FIG. 3E  FIG. 3H

```
                           SEQUENCE LISTING

<160> NUMBER OF SEQ ID NOS: 1

<210> SEQ ID NO: 1
<211> LENGTH: 13
<212> TYPE: PRT
<213> ORGANISM: Artificial Sequence
<220> FEATURE:
<223> OTHER INFORMATION: Description of Artificial Sequence:
      Autocamtide-2

<400> SEQUENCE: 1

Lys Lys Ala Leu Arg Arg Gln Glu Thr Val Asp Ala Leu
 1               5                  10
```

TRANSGENIC MOUSE MODEL FOR CARDIAC HYPERTROPHY AND METHODS OF USE THEREOF

CROSS-REFERENCE TO RELATED APPLICATIONS

This application claims benefit of U.S. Provisional Application Serial No. 60/062,864, filed Oct. 16, 1997, U.S. Provisional Application Serial No. 60/065,178, filed Nov. 10, 1997, U.S. Provisional Application Serial No. 60/081,853, filed Apr. 15, 1998, and is a continuation of U.S. patent application Ser. No. 09/061,417, filed Apr. 16, 1998, now pending.

STATEMENT OF RIGHTS TO INVENTIONS MADE UNDER FEDERALLY SPONSORED RESEARCH

Financial support for the present invention was provided in part by the U.S. Government under Grant No. 805-3351 awarded by the National Institutes of Health. Accordingly, the U.S. Government may have certain rights in the claimed invention.

TECHNICAL FIELD

The present invention relates to transgenic animal models for cardiac hypertrophy. It further relates to the use of such transgenic animals to detect substances with therapeutic activity toward cardiac hypertrophy. It further relates to assays to detect substances for use in treating cardiac hypertrophy. It further relates to methods for treating cardiac hypertrophy.

BACKGROUND ART

Cardiac Hypertrophy

Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to dilated cardiomyopathy, heart failure, and sudden death. In the United States, approximately half a million individuals are diagnosed with heart failure each year, with a mortality rate approaching 50%.

Despite the diverse stimuli that lead to cardiac hypertrophy, there is a prototypical final molecular response of cardiomyocytes to hypertrophic signals that involves an increase in cell size and protein synthesis, enhanced sarcomeric organization, up-regulation of fetal cardiac genes, and induction of immediate-early genes, such as c-fos and c-myc. See, Chien et al. (1993) *Ann. Rev. Physiol.* 55:77–95; and Sadoshima and Izumo (1997) *Ann. Rev. Physiol.* 59:551–571. The causes and effects of cardiac hypertrophy have been extensively documented, but the underlying molecular mechanisms that couple hypertrophic signals initiated at the cell membrane to the reprogramming of cardiomyocyte gene expression remain poorly understood. Elucidation of these mechanisms is a central issue in cardiovascular biology and will be critical for designing new strategies for prevention or treatment of cardiac hypertrophy and heart failure.

Numerous studies have implicated intracellular $Ca^{2+}$ as a signal for cardiac hypertrophy. In response to myocyte stretch or increased loads on working heart preparations, intracellular $Ca^{2+}$ concentrations increase (Marban et al. (1987) *Proc. Natl. Acad. Sci. USA* 84:6005–6009; Bustamante et al. (1991) *J. Cardiovasc. Pharmacol.* 17:S110–S113; and Hongo et al. (1995) *Am J. Physiol.* 269:C690–C697, consistent with a role of $Ca^{2+}$ in coordinating physiologic responses with enhanced cardiac output. A variety of humoral factors, including angiotensin II (AngII), phenylephrine (PE), and endothelin-1 (ET-1), which induce the hypertrophic response in cardiomyocytes, also share the ability to elevate intracellular $Ca^{2+}$ concentrations. Karliner et al. (1 990) *Experientia* 46:81–84; Sadoshima and Izumo (1993) *Circ. Res.* 73:424–438; Sadoshima et al. (1993) *Cell* 75:977–984; and Leite et al. (1994) *Am. J. Physiol.* 267:H2193–H2203.

Hypertrophic stimuli result in reprogramming of gene expression in the adult myocardiumn, such that genes encoding fetal protein isoforms like β-myosin heavy chain (MHC) and α-skeletal actin are up-regulated, whereas the corresponding adult isoforms, α-MHC and α-cardiac actin, are down-regulated. The natriuretic peptides, atrial natriuretic factor (ANF), and b-type natriuretic peptide (BNP), which decrease blood pressure by vasodilation and natriuresis, are also rapidly up-regulated in the heart in response to hypertrophic signals. Komuro and Yazaki (1993) *Ann. Rev. Physiol.* 55:55–75. The mechanisms involved in coordinately regulating these cardiac genes during hypertrophy are unknown, although binding sites for several transcription factors, including serum response factor (SRF), TEF-1, AP-1, and Sp1, are important for activation of fetal cardiac genes in response to hypertrophy. Sadoshima and Izumo (1993); Sadoshima et al. (1993); Kariya et al. (1994) *J. Biol. Chem.* 269:3775–3782; Karns et al. (1995) *J. Biol. Chem.* 270:410–417; and Kovacic-Milivojevic et al. (1996) *Endocrinol.* 137:1108–1117. Most recently, the cardiac-restricted zinc finger transcription factor GATA4 has also been shown to be required for transcriptional activation of the genes for Ang II type 1a receptor and β-MHC during hypertrophy. Herzig et al. (1997) *Proc. Natl. Acad. Sci. USA* 94:7543–7548; Hasegawa et al. (1997) *Circulation* 96:3943–3953; and Molkentin and Olson (1997) *Circulation* 96:3833–3835.

A number of intracellular signaling pathways have been implicated in transduction of hypertrophic stimuli. For example, occupancy of the cell surface receptors for AngII, PE, and ET-1 leads to activation of phospholipase C, resulting in the production of diacylglycerol and inositol triphosphate, which in turn results in mobilization of intracellular $Ca^{2+}$ and activation of protein kinase C (PKC). Sadoshima and Izumo (1 993); Yamazaki et al. (1996) *J. Biol. Chem.* 271:3221–3228; and Zou et al. (1996) *J. Biol. Chem.* 271:33592–33597. There is also evidence that the Ras and mitogen-activated protein (MAP) kinase pathways are transducers of hypertrophic signals. Thorburn et al. (1 993) *J. Biol. Chem.* 268:2244–2249; and Force et al. (1996) *Circ. Res.* 78:947–953. The extent to which these signaling pathways are coordinated during cardiac hypertrophy is unknown. However, all of these pathways are associated with an increase in intracellular $Ca^{2+}$, consistent with a central regulatory role of $Ca^{2+}$ in coordinating the activities of multiple hypertrophic signaling pathways.

In B and T cells, the $Ca^{2+}$, calmodulin-dependent phosphatase calcineurin has been shown to link intracellular signaling pathways that result in elevation of intracellular $Ca^{2+}$ with activation of the immune response. Calcineurin regulates immune response genes through dephosphorylation of a family of transcription factors known as NF-ATs (nuclear factors of activated T cells). Rao et al. (1997) *Ann. Rev. Immunol.* 15:707–747. Once dephosphorylated by calcineurin, NF-AT transcription factors translocate to the nucleus and directly activate immune response genes. Flanagan et al. (1991) *Nature* 352:803–807; Loh et al. (1996) *Mol. Cell. Biol.* 16:3945–3954; and Loh et al. (1996) *J. Biol. Chem.* 271:10884–10891. The immunosuppressant drugs cyclosporin A (CsA) and FK506 suppress the immune response by inhibiting calcineurin's ability to activate NF-AT transcription factors. Shaw et al. (1995) *Proc. Natl. Acad. Sci. USA* 92:11205–11209; Loh et al. (1996) *J. Biol. Chem.* 271:10884–10891.

There are no spontaneous mouse mutations with sufficient similarities to cardiac hypertrophy to be usefil as experimental models. A transgenic rodent line has been produced that overexpresses calmodulin under the control of the human atrial natriuretic factor gene. Gruver et al. (1993) *Endocrinology* 133:376–388. In these mice, developmental overexpression of CaM in mouse cardiomyocytes produced a markedly exaggerated cardiac growth response, characterized by the presence of cardiomyocyte hypertrophy in regions demonstrated to overexpress CaM and by cardiomyocyte hyperplasia, apparent at early developmental stages. However, the expression of calmodulin in these animals is constitutive and is thus not reflective of physiological conditions in humans. Transgenic mice have been created in which a reporter gene is regulated by a tetracycline-controlled transactivator (tTA), which in turn is under the transcriptional control of 2.9 kb of 5' flanking sequence from the rat α-myosin heavy chain gene. Yu et al. (1996) *Circ. Res.* 79:691–697.

Current medical management of cardiac hypertrophy includes the use of three types of drugs: calcium channel blocking agents, β-adrenergic blocking agents, and disopyramide. Kikura and Levy (1995) *Int. Anesthesiol. Clin.* 33:21–37. Therapeutic agents for heart failure include angiotensin II converting enmine (ACE) inhibitors and diuretics. Other pharmaceutical agents which have been disclosed for treatment of cardiac hypertrophy include angiotensin II receptor antagonists (U.S. Pat. No. 5,604,251); and neuropeptide Y antagonists (International Patent Publication No. WO 98/33791). Despite currently available pharmaceutical compounds, prevention and treatment of cardiac hypertrophy, and subsequent heart failure, continue to present a therapeutic challenge.

Thus, there is a need for the development of new pharmacologic strategies for prophylaxis and treatment of cardiac hypertrophy in humans. In order to develop such strategies, there is a need for animal models which accurately reflect the pathological profile of the disease, to allow identification of novel targets for therapeutic intervention. In addition, there is a need for novel assays that allow identification of potential new therapeutic agents to treat cardiac hypertrophy.

SUMMARY OF THE INVENTION

The present invention provides non-human animal models for cardiac hypertrophy. Such models are useful for identifying additional targets for treatment of cardiac hypertrophy, and for testing substances for efficacy in treating cardiac hypertrophy. In one aspect, the invention provides a transgenic non-human animal comprising as a transgene a polynucleotide which, when introduced at an early stage into a fertilized egg or embryo of a mammalian non-human animal, can be functionally integrated into the genome thereof, thereby to produce a transgenic animal, characterized in that the polynucleotide comprises a nucleotide sequence encoding a gene product which modulates transcription of at least one gene that is expressed in cardiomyocytes in response to a cardiac hypertrophic signal, in combination with control sequences, including, for example, a promoter, which direct and regulate expression of the gene in somatic cells of the transgenic animal, particularly in cardiomyocytes.

The present invention encompasses a transgenic animal comprising as a transgene a polynucleotide encoding a gene product that modulates transcription of at least one gene expressed in cardiomyocytes in response to a cardiac hypertrophic signal, wherein the animal has a substantially increased probability of spontaneously developing symptoms of hypertrophic cardiomyopathy or similar heart dysfimction.

The present invention further encompasses a transgenic animal comprising as a transgene a polynucleotide encoding a gene product that modulates transcription of at least one gene expressed in cardiomyocytes in response to a cardiac hypertrophic signal, wherein the animal has a substantially decreased probability of spontaneously developing symptoms of hypertrophic cardiomyopathy or similar heart dysfimction.

Transgenic animals of the invention are useful in identifying novel targets for prophylaxis and therapy of cardiac hypertrophy and cardiac hypertrophy-induced dysfunctions. These animals are also useful for investigative purposes, for examining signal transduction pathways involved in response to hypertrophic signals. These animals are further useful to screen for potential therapeutic agents for treatment and/or prophylaxis of cardiac hypertrophy.

Preferably, the polynucleotide used to generate a transgenic animal of the invention is a recombinant DNA construct in which the promoter and at least some control sequences direct expression of an operably linked coding sequence. In some embodiments, the promoter and control sequences are expressed in a cardiomyocyte-specific manner. The coding sequence is fused to a downstream segment comprising at least a fragment of a eukaryotic gene sequence effective to provide signals for terminating transcription and for controlling processing of transcribed RNA during expression of the encoded gene product. In one embodiment, the promoter is derived from an α-myosin heavy chain gene (α-MHC). In other embodiments, the transcriptional control sequences comprise elements which confer inducible expression on the operably linked coding sequence. In some embodiments, the transgenic animal comprises a transgene which encodes a polypeptide which modulates transcription of at least one cardiac hypertrophy-sensitive gene. In these embodiments, the polypeptide can comprise a wild-type amino acid sequence or a mutant amino acid sequence such that the polypeptide has altered function, such as an altered enzymatic fimction or has altered regulatory properties, including, for example, a dominant negative mutant. In other embodiments, the transgene-encoded gene product is an antisense polynucleotide. In yet other embodiments, the transgene-encoded gene product is a ribozyme.

The constructs are introduced into animal embryos using standard techniques such as microinjection or embryonic stem cells. Cell culture-based models can also be prepared by various methods. For example, cells can be isolated from the transgenic animals or prepared from established cell cultures using the same constructs with standard cell transfection techniques.

The invention further provides a method for producing a transgenic animal, for example a mouse or other rodent, having either a substantially increased probability of spontaneously developing hypertrophic cardiomyopathy or similar heart dysfunction or a substantially decreased probability of spontaneously developing hypertrophic cardiomyopathy or similar heart dysfunction, said method comprising incorporating a polynucleotide as specified above into the genome of a non-human animal such that it is functionally integrated therein. At least in preferred embodiments the nucleic acid is a recombinant DNA which is introduced into a fertilized egg or embryo of the animal in order to become functionally integrated into the genome thereof, said recombinant DNA being characterized in that it contains a segment comprising a gene sequence coding a gene product which of modulates transcription of at least one gene that is expressed in cardiomyocytes in response to a hypertrophic signal, or for a derivative of such a gene product, which segment is fused to an upstream segment comprising promoter and at least some control sequences effective to direct and regulate expression of said coding, and also, preferably, to a downstream segment comprising a eukaryotic gene sequence or fragment effective to provide signals for termination of transcription and for controlling processing of the transcribed RNA.

Constructs for use in generating transgenic animals can be constructed such that expression of the transgene can be constitutive or inducible. A polynucleotide, for use in generating a transgenic animal, comprises a nucleotide sequence which encodes a gene product which modulates transcription of at least one gene that is expressed in cardiomyocytes in response to a hypertrophic signal. In one aspect, the nucleotide sequence which encodes a gene product which modulates transcription of at least one gene that is expressed in cardiomyocytes in response to a hypertrophic signal is constitutively expressed. In another aspect, the gene which encodes a gene product which modulates transcription of at least one gene that is expressed in cardiomyocytes in response to a hypertrophic signal is expressed in a regulatable manner. In another aspect, the gene which encodes a gene product that modulates transcription of at least one gene that is expressed in cardiomyocytes in response to a hypertrophic signal comprises a portion which encodes a dominant negative mutant of a polypeptide.

In one aspect of the invention, a transgenic animal comprises, as a transgene a gene encoding a gene product that represses the transcription of at least one gene that is expressed in cardiomyocytes in response to a hypertrophic signal. In another aspect of the invention, the transgene-encoded gene product induces the transcription of at least one gene that is expressed in cardiomyocytes in response to a hypertrophic signal. For example, the transcription factor YY1 is a global repressor of cardiac hypertrophic responsive genes, while calcineurin generally induces the transcription of cardiac hypertrophic responsive genes.

Another aspect of the invention relates to cells isolated from the above-described transgenic animals. Preferably, such cells are derived from cardiac tissue and are cardiomyocytes. Cardiomyocytes isolated from the transgenic animals of the present invention can be used to test cardiotherapeutic properties of substances to which the cells are exposed in vitro. Thus, the cells are useful to screen for potential therapeutic agents for treatment and/or prophylaxis of cardiac hypertrophy. Such cells can also be used to identify novel targets for prophylaxis and therapy of cardiac hypertrophy and cardiac hypertrophy-induced dysfunctions. These cells are also useful for investigative purposes, for examining signal transduction pathways involved in response to hypertrophic signals.

The invention further provides methods for screening substances for use in treating a cardiac hypertrophy-induced disease state (dysfunction).

In some embodiments, enzyme-based screening assays are provided, wherein the enzymes used are involved in modulating levels of active product of at least one gene that is expressed in cardiomyocytes in response to a hypertrophic signal. The methods generally involve contacting the enzyme with a substance being tested and measuring an activity of the enzyme, compared to a control sample comprising the enzyme in the absence of the substance being tested.

In other embodiments, cell-based screening assays are provided, wherein substantially isolated cardiomyocytes are contacted with a substance to be tested, followed by measuring a cardiomyocyte function or parameter. An alteration in the cardiomyocyte function being measured, when compared to a control cell sample to which no substance is added, indicates that the substance is suitable for use in treatment of a cardiac hypertrophy-induced dysfunction. In some of these embodiments, the cardiomyocytes are derived from a transgenic animal of the invention. In other embodiments, the cardiomyocytes are derived from a non-transgenic animal.

In still other embodiments, whole animal-based screening assays are provided. In these embodiments, invention encompasses the use of transgenic animals of the invention, or parts thereof, for testing cardiotherapeutic properties of substances administered to said animals, or for testing the activity of such substances in controlling or inhibiting the development of hypertrophic cardiomyopathy. Thus, according to another aspect of the invention, a method of screening and identifying or testing a drug or other substance for activity against the development of or in the treatment of hypertrophic cardiomyopathy, comprising treating a transgenic animal of the invention, or a part thereof, with said drug or other substance concerned and detecting or noting any reduced incidence in the development of hypertrophic cardiomyopathy and reduction in morbidity, as compared with corresponding animals that are not treated with the drug or substance, or detecting or noting an effectiveness in maintaining, restoring or improving heart function.

The invention further provides the use of compositions comprising substances identified by the methods of the present invention, as well as known substances, for treating cardiac hypertrophy and heart failure. Such compositions include substances which increase active levels of one or more gene products which normally repress transcription of at least one gene that is expressed in cardiomyocytes in response to a hypertrophic signal, thereby reducing the expression of the at least one gene that is expressed in cardiomyocytes in response to a hypertrophic signal. Such compositions also include substances which reduce active levels of one or more gene products which normally increase transcription of at least one gene that is expressed in cardiomyocytes in response to a hypertrophic signal, thereby reducing the expression of the at least one gene that is expressed in cardiomyocytes in response to a hypertrophic signal. Further included are substances which are known modulators of gene products that modulate transcription of at least one gene that is expressed in cardiomyocytes in response to a hypertrophic signal, for use in treating a cardiac hypertrophy-induced dysfunction. Included are known inhibitors of calcineurin, and derivatives of these inhibitors that inhibit a phosphatase activity of calcineurin.

The invention further provides methods of treating cardiac hypertrophy using modulators of gene products which modulate transcription of at least one gene that is expressed in cardiomyocytes in response to a hypertrophic signal. In one aspect of the invention, calcineurin inhibitors are used to control cardiac hypertrophy and heart failure. The invention further provides methods of treating cardiac hypertrophy, or a cardiac hypertrophy-induced dysfunction, comprising administering to an individual in need thereof a substance which diminishes or reverses the progression of the dysfunction. In some embodiments, the substances inhibit expression of genes whose products modulate transcription of at least one gene that is expressed in cardiomyocytes in response to a hypertrophic signal. In other embodiments, the substances inhibit an activity of a product of such a gene. In some embodiments, the methods comprise adminstering a composition comprising a known inhibitor of calcineurin, and derivatives of these inhibitors that inhibit a phosphatase activity of calcineurn.

BRIEF DESCRIPTION OF THE DRAWINGS

The patent or application file contains at least one photograph executed in color. Copies of this patent or patent application publication with color photographs will be provided by the Office upon request and payment of the necessary fee.

FIGS. 2A–F show inhibition of Angiotensin II- and phenylephrine-induced hypertrophy of primary cardiomyocytes by CsA and FK506. A–F, Primary rat cardiocytes in serum-free medium were stimulated with AngII (10 nM) or PE (10 μm) for 72 hours. Cells were then fixed and stained with anti-α-actinin antibody to reveal sarcomeres and Hoechst stain to reveal nuclei. CsA (500 ng/ml) was added to one set of cultures at the time of AngII addition.

FIGS. 3A–H show photographs of hearts of α-MHC calcineurin transgenic mice. A, Control and α-MHC-calcineurin transgenic littermates were sacrificed at 18 days of age and the hearts were removed and photographed. B,C, Hearts shown in A were sectioned longitudinally to reveal the ventricular chambers and interventricular septum. D,E, High magnification views of left ventricular walls of hearts shown in B and C, respectively. F, G, Transverse sections through hearts of control and calcineurin transgenics at 9 weeks of age stained with H&E. H, Sections from the calcineurin transgenic heart shown in G were stained with Masson trichrome to reveal collagen. ca, coronary artery; la, left atrium; lv, left ventricle; re, right atrium; rv, right ventricle. Bars in B,C,F,G,H=1 mm. Bars in D,E=50 μm.

FIGS. 10A, B, and C are bar graphs showing luciferase reporter levels after transfection of ANF, skeletal α-actin, and cardiac a-actin, respectively, into ventricular myocardial cells, and treatment, 24 hours after transfection, with PE (100 μM), DOB (10 μM), or TGF-β1 (1 ng/ml). Values are corrected for transfection efficiency and reported as the mean±SD from at least three experiments. FIG. 10D. Ventricular myocardial cells were switched to serum-free medium. DOB was added to the medium at various time points. "Control" represents cells treated with the DOB vehicle. 24 hours after incubation, total RNA was extracted and analyzed by Northern blot Results are representative of n=3 or greater for each time point.

FIG. 11A shows a time course of target gene transcription. Open circles, empty vector, no DOX; filled circles, empty vector, plus DOX; open triangles, pUHC13-3, no DOX; filled triangles, pUHC13-3, plus DOX. FIG. 11B is a bar graph depicting the ability of tTA to stimulate transcription of the target gene and the inhibitory effect of doxcycline 12 hours after transfection.

MODES FOR CARRYING OUT THE INVENTION

Figure 1:
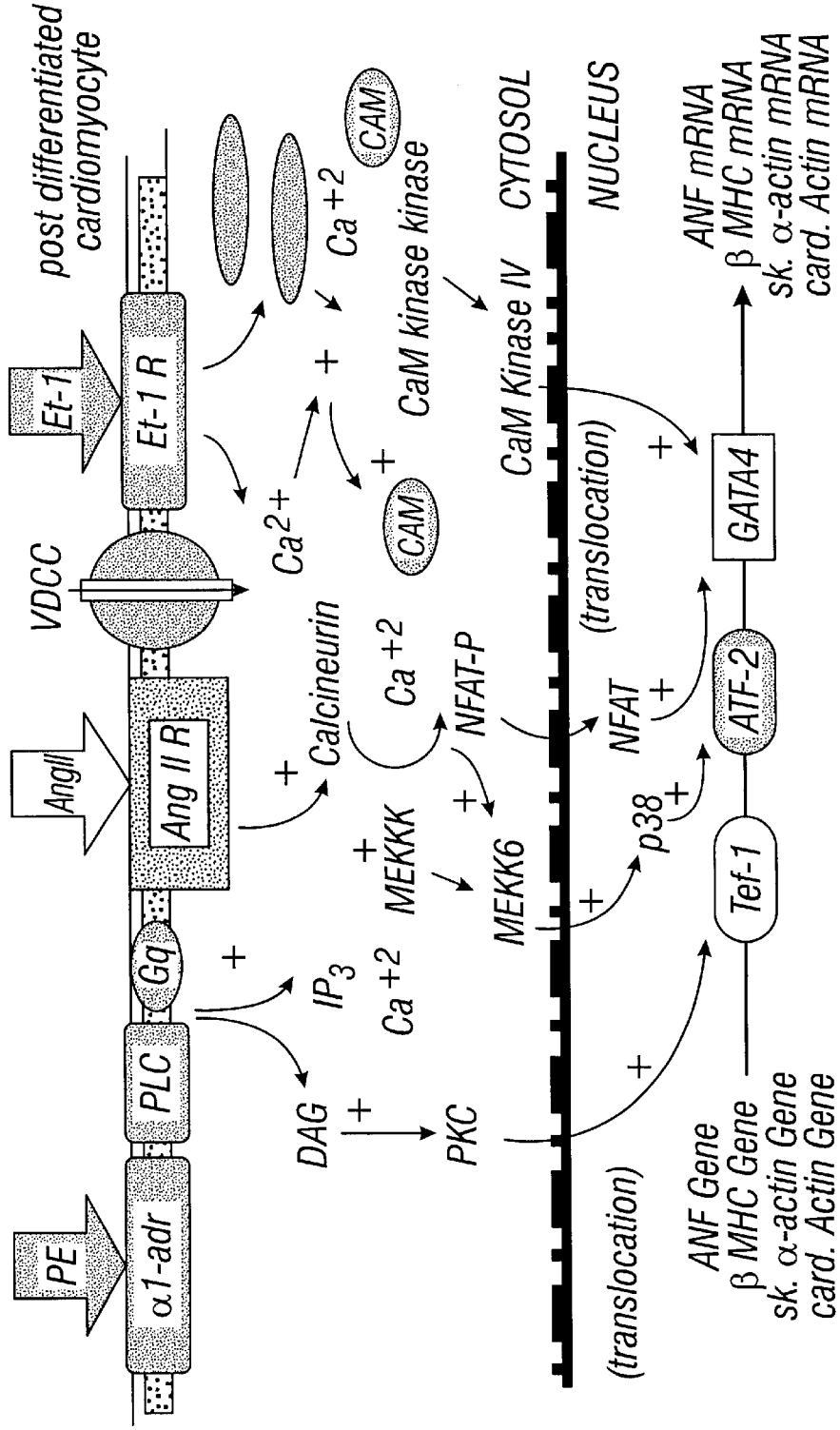
FIG. 1 presents a model of nuclear signaling and transcriptional control of hypertrophy-induced embryonic gene expression. Abbreviations used are as follows: VDCC, voltage-dependent calcium channel; PLC, phospholipase C; AngII, angiotensin II; Et-1, endothelin-1; DAG, diacylglycerol; PKC, protein kinase C; IP3, inositol-3-phosphate; CAM, calmodulin.

The present invention provides transgenic non-human animals which comprise, as transgenes, recombinant polynucleotides comprising a coding sequence encoding a gene product which modulates transcription of at least one gene that is expressed in cardiomyocytes in response to a hypertrophic signal. Depending on the transgene, a transgenic animal of the invention has a substantially increased, or substantially reduced, probability of spontaneously developing cardiac hypertrophy.

The construction of transgenic animal models, using the recombinant polynucleotides for testing potential treatments for cardiac hypertrophy is described. The present invention provides transgenic non-human mammals comprising recombinant polynucleotides comprising a coding sequence encoding a gene product which modulates transcription of at least one gene that is expressed in cardiomyocytes in response to a hypertrophic signal. The constructs are introduced into animal embryos using standard techniques such as microinjection or embryonic stem cells.

The present invention provides transgenic non-human animals and cells isolated from transgenic non-human animals, wherein the transgene encodes a gene product which modulates transcription of at least one gene that is expressed in cardiomyocytes in response to a hypertrophic signal, and wherein the isolated cells express the transgene.

The invention encompasses transgenic animals, or cells isolated therefrom, which can be used to screen for substances which can reduce cardiac hypertrophy, as measured by various parameters including, but not limited to, left ventricular mass/body weight, changes in cardiomyocyte size and organization, changes in cardiac gene expression and changes in cardiac function.

The present invention provides methods for detecting substances having therapeutic potential toward cardiac hypertrophy, using either transgenic animals or cells isolated therefrom. In addition, the present invention provides screening assays using substantially isolated enzymes involved in modulating levels of at least one gene that is expressed in cardiomyocytes in response to a hypertrophic signal. The screening assays can also be carried out using cells that are derived from non-transgenic animals.

The invention further provides methods for treating a cardiac hypertrophy-induced dysfunction, comprising administering to an individual in need of such treatment a composition comprising a substance which modulates active levels of at least one product of a gene expressed in response to a hypertrophic signal. The substances comprised in these compositions include those detected by the methods of the present invention, as well as known substances and their derivatives.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzy-*

*mology* (Academic Press, Inc.); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); and *Current Protocols in Immunology* (J. E. Coligan et al., eds., 1991).

For techniques related to the production of transgenic animals, see, inter alia, Hogan et al (1986) *Manipulating the Mouse Embryo—A Laboratory Manual Cold* Spring Harbor Laboratory, Cold Spring Harbor, N.Y., 1986).

As used herein, the term "a gene product which modulates transcription of at least one gene that is expressed in cardiomyocytes in response to a hypertrophic signal" refers to any gene product, either a protein or an RNA, that modulates the transcription of at least one gene expressed in cardiomyocytes in response to a hypertrophic signal. It is also one which reduces or modulates activity of at least one gene that is expressed in cardiomyocytes in response to a hypertrophic signal by reducing levels of transcription and/or translation or reducing protein activity e.g., by competitive or non-competitive inhibition, or by reducing protein concentration, and the like. The "modulation" can be either a down-regulation or an up-regulation of the gene expressed in cardiomyocytes in response to a hypertrophic signal.

A gene expressed in cardiomyocytes in response to a hypertrophic signal is also referred to herein as a "cardiac hypertrophy-sensitive gene" or a "cardiac hypertrophic-responsive gene". Examples of genes expressed in response to hypertrophic signals include, but are not limited to, atrial natriuretic factor (ANF), α-skeletal actin, b-type natriuretic peptide (BNP), cardiac actin, and β-myosin heavy-chain (β-MHC), as shown schematically in FIG. 1.

The term "transgenic animal" refers to a non-human animal, preferably a non-human mammal, which has integrated into its germline DNA one or more DNA sequences which have been introduced into the animal.

As used herein, the term "hypertrophic signal" indicates any stimulus, mechanical or chemical, which results in measurable symptoms of cardiac hypertrophy. Hypertrophic signals include, but are not limited to, mechanical stretch, β-adrenergic agonists, $\alpha_1$-adrenergic receptor agonists and angiotensin II. Symptoms of cardiac hypertrophy can be measured by various parameters including, but not limited to, left ventricular mass:body weight ratio; changes in cardiomyocyte size, mass, and organization; changes in cardiac gene expression; changes in cardiac function; fibroid deposition; changes in dP/dT, i.e., the rate of change of the ventricular pressure with respect to time; calcium ion flux; stroke length; and ventricular output.

The terms "transcriptional regulatory element" (TRE) and "transcriptional control region", "transcriptional response element", and "transcriptional control element", used interchangeably herein, refer to a polynucleotide sequence, preferably a DNA sequence, which selectively activates transcription of an operably linked polynucleotide sequence in a host cell. A TRE usually includes a promoter region and may optionally include, in addition to a promoter, other control sequences such as enhancers and silencers.

A "heterologous" TRE, promoter or enhancer is one that is not normally associated in a cell with, or is not derived from, a gene's 5' flanking sequence. In the context of a gene encoding a product that modulates active levels of at least one gene product of a hypertrophy-sensitive gene, examples of a heterologous promoter or enhancer include an α-myosin heavy chain gene 5' flanlding region.

The term "operably linked" relates to the orientation of polynucleotide elements in a functional relationship. A TRE is operably linked to a coding segment if the TRE promotes transcription of the coding sequence. Operably linked means that the DNA sequences being linked are generally contiguous and, where necessary to join two protein coding regions, contiguous and in the same reading frame. However, since enhancers generally function when separated from the promoter by several kilobases, some polynucleotide elements may be operably linked but not contiguous.

The terms "polynucleotide" and "nucleic acid", used interchangeably herein, refer to a polymeric form of nucleotides of any length, either ribonucleotides or deoxyribonucleotides. Thus, this term includes double- and single-stranded DNA and RNA. One skilled in the art would recognize that point mutations and deletions can be made to the promoter sequences and coding region sequences used in the present invention without altering the ability of the sequence to carry out its function, whether that function would be to activate transcription or to encode a functional protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A "substantially isolated" or "purified" polynucleotide is one that is substantially free of the materials with which it is associated in nature. By substantially free is meant at least 50%, preferably at least 70%, more preferably at least 80%, and even more preferably at least 90% free of the materials with which it is associated in nature. As used herein, a "substantially isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only intact antibody molecules but also fragments of antibody molecules retaining antigen binding ability. Such fragments are also well known in the art and are regularly employed both in vitro and in vivo. In particular, as used herein, the term "antibody" means not only intact immunoglobulin molecules of any isotype (IgA, IgG, IgE, IgD, IgM) but also the well-known active fragments F(ab')$_2$, Fab, Fv, scFv, Fd, $V_H$ and $V_L$. For antibody fragments, see, for example "Immunochemistry in Practice" (Johnstone and Thorpe, eds., 1996; Blackwell Science), p. 69.

As used herein, a "cardiac hypertrophy-induced dysfunction" is a condition or disease related to cardiac hypertrophy and includes cardiac hypertrophy, compound cardiac hypertrophy, dilated cardiac hypertrophy, decompensated cardiac hypertrophy, and heart failure. A cardiac hypertrophy-induced dysfunction is characterized by one or more of the following symptoms or events: concentric enlarged ventricular mass; eccentric enlarged ventricular mass; progression toward dilated cardiac myopathy; extensive fibroid deposition; changes in dP/dT; cardiomyocyte disarray; calcium ion release and uptake (i.e., $Ca^{2+}$ flux); stroke shortening; diminished ventricular output; arrhythmias; tachycardia; changes in central demand; and heart failure.

Transgenic Animals

The transgenic animals of the present invention include those which have a substantially decreased probability of spontaneously developing cardiac hypertrophy, and those which have a substantially increased probability of spontaneously developing cardiac hypertrophy, when compared with non-transgenic littermates. A "substantially increased" or a "substantially decreased" probability of spontaneously developing cardiac hypertrophy means that a statistically significant increase or decrease, respectively, of measurable symptoms of cardiac hypertrophy is observed when comparing the transgenic animal with a non-transgenic littermate (s).

The transgenic animals of the present invention are produced with transgenes which comprise a coding region that encodes a gene product which modulates transcription of at least one gene that is expressed in cardiomyocytes in response to a hypertrophic signal. Coding regions for use in constructing the transgenes of the present invention include, but are not limited to, those which encode MEF-2, p38, calcineurin (CaN), CaMIIα, CaMKIV, GATA4, and YY1. The coding regions may encode a complete polypeptide, or a fragment thereof, as long as the desired fimction of the polypeptide is retained, i.e., the polypeptide can modulate transcription of at least one gene that is expressed in cardiomyocytes in response to a hypertrophic signal. The coding regions for use in constructing the transgenes of the present invention further include those containing mutations, including silent mutations, mutations which lead to a change in amino acid sequence but which do not result in functional alterations, mutations resulting in a more active protein, mutations that result in a constitutively active protein, mutations resulting in a protein with reduced activity, and dominant negative mutants. Coding regions can be derived from human, rat, or mouse sequences, several of which have been disclosed. Nucleotide sequences have been disclosed for mouse CaN catalytic subunit mRNA (GenBank Accession Nos. M81475 and J05479); human p38 mRNA (GenBank Accession No. AF015256); human YY1 mRNA (GenBank Accession No. Z14077); and rat CaMKIIIα mRNA (GenBank Accession No. J02942). As noted above, these sequences, or variations or mutations thereof, can be used. As examples of constitutively active mutants, constitutively active forms of CaN, CaMKII and CaMKIV have been described. Sun et al. (1994) *Genes Dev.* 8:2527–2539; Cruzalegui and Means (1993) *J. Biol. Chem.* 268:26171–26178; and O'Keefe et al. (1992) *Nature* 357:692–694.

The transgenes, for use in generating transgenic animals, which comprise a coding region that encodes a gene product which modulates transcription of at least one gene that is expressed in cardiomyocytes in response to a hypertrophic signal, include those in which the gene product which modulates transcription of at least one hypertrophy-sensitive gene is 1) under the control of a cardiomyocyte-specific promoter; 2) constitutively expressed in cardiomyocytes under the control of a cardiomyocyte-specific promoter; 3) under the control of a cardiomyocyte-specific promoter but is expressed in an inducible manner.

Transcriptional Regulatory Elements

Transgenic animals of the present invention comprise, as a transgene, a polynucleotide comprising a coding region encoding a gene product that modulates expression of at least one gene expressed in cardiomyocytes in response to a hypertrophic signal. Transcription of the coding region is controlled by a transcriptional regulatory element (TRE). TREs suitable for use in the present invention include those which direct the transcription of a coding region to which they are operably linked preferentially in cardiomyocytes. By "preferentially" is meant that the expression of the transgene in cardiomyocytes is at least about 10-fold, more preferably at least about 10-fold to about 50-fold, even more preferably at least about 50-fold to 100-fold, even more preferably more than 100-fold greater than that in non-cardiomyocytes. Preferably, expression of the transgene is below detectable limits in cells other than cardiomyocytes, as indicated by reporter gene assays, such as those described in the Examples.

A variety of cardiomyocyte-specific TREs have been described in the literature and can be used in the present invention. These include, but are not limited to, TREs derived from the following genes: myosin light chain-2, α-myosin heavy chain, AE3, cardiac troponin C, and cardiac α actin. Franz et al. (1997) *Cardiovasc. Res.* 35:560–566; Robbins et al. (1995) *Ann. N.Y. Acad. Sci.* 752:492–505; Linn et al. (1995) *Circ. Res.* 76:584–591; Parmacek et al. (1994) *Mol. Cell. Biol.* 14:1870–1885; Hunter et al. (1993) *Hypertension* 22:608–617; and Sartorelli et al. (1992) *Proc. Natl. Acad. Sci. USA* 89:4047–4051.

In one embodiment, the TRE comprises a promoter region from the 5' flanking region of an α-MHC gene. A 5443 base 5' flanking sequence for the mouse α-MHC gene is provided in GenBank under accession number U71441. Although the entire 5.4 kb sequence can be used in the transgenes of the present invention, portions thereof which direct transcription of an operably linked coding region preferentially in cardiomyocytes can also be used. The α-MHC expression vector described in Example 2 can be used to insert a desired coding region such that the coding region will be operably linked to the α-MHC promoter. Jones et al. (1994) *Dev. Dyn.* 200:117–128.

In another embodiment, the TRE comprises a promoter region from the 5' flanking region of a b-type natriuretic peptide gene (BNP). Thuerauf and Glembotski (1997) *J. Biol. Chem.* 272:7464–7472; and LaPointe et al. (1996) *Hypertension* 27:715–722. A nucleotide sequence for a 5' flanking region of human BNP has been disclosed (GenBank Accession No. D16641).

In other embodiments, the coding region is operably linked to an inducible regulatory element(s). A variety of inducible promoter systems have been described in the literature and can be used in the present invention. These include, but are not limited to, tetracycline-regulatable systems, (WO 94/29442; WO 96/40892; and WO 96/01313); hormone-responsive systems, interferon-inducible systems, metal-inducible systems, and heat-inducible systems, (WO 93/20218); and ecdysone-inducible systems. Some of these systems, including ecdysone-inducible and tetracycline-inducible systems are commercially available from Invitrogen (Carlsbad, Calif.) and Clontech (Palo Alto, Calif.), respectively.

In some embodiments, the inducible (regulatable) promoter system comprises a tetracycline-binding operator, tetO, regulated by addition of tetracycline (or an analog thereof) to the animal's water or diet, operably linked to a coding region whose product modulates transcription of at least one gene expressed in cardiomyocytes in response to a hypertrophic signal. Systems suitable for use in the present invention are well known. Yu et al. (1996) *Circ. Res.* 79:691–697; Gossen et al. (1992) *Proc. Natl. Acad. Sci. USA* 89:5547–5551; and Hillen and Wissmann, in *Protein-Nucleic Acid Interaction, Topics in Molecular and Structural Biology*, Saenger and Heinemann, eds. CRC Press Boca Raton, Fla. (1989), pp. 143–162. In general, this system makes use of a hybrid fusion protein, the tetracycline transactivator (tTA), which comprises a DNA binding domain, capable of binding tetO, derived from a polypeptide such as the tet repressor (tetR) protein from *E. coli*, coupled to a transcriptional activation domain such as from the viral protein VP16, such that when tTA binds to a minimal promoter containing tetO sequences, transcription of the target gene is activated. Tetracycline binding to tTA prevents activation, presumably by causing a conformational change in the tetR portion of tTA, blocking binding of tTA to tetO. Gene activation occurs by removing tetracycline.

In addition, cell type-specific TREs can be used. Cell type-specific TREs include, but are not limited to, those derived from the following exemplary genes (cell type in which the TREs are specifically functional are in parentheses): vascular endothelial growth factor receptor (endothelium), albumin (liver), factor VII (liver), fatty acid synthase (liver), von Willebrand factor (brain endothelium), alpha-actin and myosin heavy chain (both in smooth muscle), synthetase I (small intestine), Na—K—Cl transporter (kidney), prostate specific antigen (prostate), and glandular kallikrein-1 gene (prostate).

Another class of TREs are those which activate transcription of an operably linked polynucleotide in response to hypoxic conditions. These include TREs regulated, at least in part, by hypoxia-inducible factor-1. Bunn and Poyton (1996) *Physiol. Rev.* 76:839–885; Dachs and Stratford (1996) *Br. J. Cancer* 74:5126–5132; Guillemin and Krasnow (1997) *Cell* 89:9–12. Firth et al. (1994) *Proc. Natl. Acad. Sci. USA* 91:6496–6500; and Jiang et al. (1997) *Cancer Res.* 57:5328–5335.

A wide variety of viral promoters are known in the art and can be used, including, but not limited to, a cytomegalovirus (CMV) promoter, a Rous Sarcoma Virus (RSV) promoter, an SV40 promoter, and an MMTV LTR promoter. Depending on the nature of their regulation, promoters may be constitutive or regulatable by experimental conditions.

Other regulatory sequences which can be included in a transgene include polyadenylation signals, and termination signals, the latter which can serve to enhance message levels and to minimize read-through into other sequences. These regulatory sequences are known in the art.

Polynucleotides for Use in Making Transgenic Animals

Substantially isolated polynucleotides for use in making a transgenic animal of the present invention include polynucleotides comprising a coding region encoding a gene product which modulates transcription of at least one gene that is expressed in cardiomyocytes in response to a hypertrophic signal. Such gene products include polypeptides, antisense polynucleotides, and ribozymes.

Polypeptide gene products which modulate transcription of at least one gene that is expressed in cardiomyocytes in response to a hypertrophic signal include, but are not limited to, calcineurin, YY1, p38/Hog1, CAMKIV, and CaMKIIα.

Several cDNA clones suitable for use in the present invention for creating transgenic animals have been described: p38, Wang et al. (1997) *J. Biol. Chem.* 272:23668–23674 (human sequence, QenBank Accession No. AF015256); calcineurin catalytic subunit, Muramatsu and Kincaid (1992) *Biochim. Biophys. Res. Comm.* 188:265–271 (human sequence for catalytic subunit, GenBank Accession No. S46622), Kincaid et al. (1990) *J. Biol. Chem.* 265:11312–11319 (mouse sequences for catalytic subunit, GenBank Accession Nos. J05479 and M81475); and YY1, Shi et al. (1991) *Cell* 67:377–388 (human sequence, GenBank Accession No. Z14077).

Expression clones for making transgenic mice can also be constructed such that the coding region bears one or more mutations that affect the activity of the encoded protein. For example, a CaM mutant lacking amino acids 75–82 binds $Ca^{2+}$ with kinetic properties similar to those of wild-type CaM, but is unable to activate several CaM-dependent target enzymes in vitro. Van Berkum et al. (1990) *J. Biol. Chem.* 265:3750–3756.

Useful mutations include those that result in constitutively active forms of the encoded protein. For example, genes encoding constitutively active mutant forms of CaMKIV, CaMKIIα, and CaN can be used to generate transgenic animals. For example, a construct termed pSR-CaMKII(1-290), which harbors a constitutively-active truncated mutant form of this wild-type CaMKII has been described. Sei et al. (1991) *J. Biol. Chem.* 266:15910–15916.

Other useful mutations include dominant negative mutants. For example, a dominant negative mutant of a calcium/calmodulin-dependent kinase can be one that is truncated or otherwise mutated so that it loses its calcium ion sensitivity, but retains sensitivity to calmodulin. It can also be a mutant that has lost kinase activity, but still binds calmodulin. Since such a mutant would bind CaM, but would lack enzymatic activity, downstream events would be affected.

Polynucleotide gene products which are useful include antisense polynucleotides, ribozymes, and triple helix polynucleotides that modulate the expression of a product of at least one gene that is expressed in cardiomyocytes in response to a hypertrophic signal. Antisense polynucleotides and ribozymes have been amply described. S. T. Crooke and B. Lebleu, eds. *Antisense Research and Applications* (1993) CRC Press; and *Antisense RNA and DNA* (1988) D. A. Melton, Ed. Cold Spring Harbor Laboratory Cold Spring Harbor, N.Y. Anti-sense RNA and DNA molecules act to directly block the translation of mRNA by binding to targeted mRNA and preventing protein translation. An example of an antisense polynucleotide is an oligodeoxyribonucleotide derived from the translation initiation site, e.g., between −10 and +10 regions of the relevant nucleotide sequence.

Ribozymes are enzymatic RNA molecules capable of catalyzing the specific cleavage of RNA. The mechanism of ribozyme action involves sequence specific interaction of the ribozyme molecule to complementary target RNA, followed by an endonucleolytic cleavage. Within the scope of the invention are engineered hammerhead or other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, Draper PCT WO 93/23569; and U.S. Pat. No. 5,093, 246.

Nucleic acid molecules used in triple helix formation for the inhibition of transcription are generally single stranded and composed of deoxyribonucleotides. The base composition must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Anti-sense RNA and DNA molecules, ribozymes, and triple helix molecules can be prepared by any method known in the art for the synthesis of DNA and RNA molecules. See, Draper, id. These include techniques for chemically synthesizing oligodeoxyribonucleotides well known in the art including, but not limited to, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably or transiently into cells.

Various well-known modifications to the DNA molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Gene products which modulate transcription of at least one gene that is expressed in cardiomyocytes in response to a hypertrophic signal can be identified by any means known in the art, including, but not limited to, a yeast two-hybrid system, a variety of which are known in the art and described in more detail below. A transcription activation assay such as the yeast two-hybrid system allows for the identification and manipulation of protein-protein interactions. Fields and Song (1989) *Nature* 340:245–246. The conceptual basis for a transcription activation assay is predicated on the modular nature of transcription factors, which consist of functionally separable DNA-binding and trans-activation domains. When expressed as separate proteins, these two domains fail to mediate gene transcription. However, the ability to activate transcription can be restored if the DNA-binding domain and the trans-activation domain are bridged together through a protein-protein interaction. These domains can be bridged, for example, by expressing the DNA-binding domain and trans-activation domain as fusion proteins (hybrids), where the proteins that are appended to these domains can interact with each other. The protein-protein interaction of the hybrids can bring the DNA-binding and trans-activation domains together to create a transcriptionally competent complex. A known component of a signal transduction pathway such as GATA4 can act as the "bait", and can be fused to a DNA-binding protein. Expression cDNA libraries can be made which allow the expression of fusion proteins comprising a protein fused to a transcriptional activator. Proteins which bind fimctionally to GATA4 then allow transcription of the lacZ gene to take place. The product of the lacZ gene can then be detected by adding a chromogenic substrate to growth substrate. Kits for conducting such assays are commercially available.

Nucleic Acid Constructs Used to Make Transgenic Animals

Constructs for use in generating transgeric animals comprise a TRE for expression of the construct in an animal cell and a region encoding a gene product which modulates transcription of at least one gene that is expressed in cardiomyocytes in response to a hypertrophic signal.

In some embodiments, a construct for use in generating a transgenic animal comprises a region encoding a gene product which modulates transcription of at least one hypertrophy-sensitive gene in cardiomyocytes, wherein the region encoding the gene product is operably linked to a heterologous promoter such that the gene product is over-expressed in cardiomyocytes. "Over-expressed" indicates that the gene product is expressed at least about 2-fold to about 5-fold, preferably at least about 5-fold to about 50-fold, more preferably at least about 50-fold to about 100-fold, even more preferably at least about 100-fold, when compared with expression of the gene in wild-type cells or when compared with expression of the gene operably linked to its homologous promoter.

In other embodiments, the construct for use in generating a transgenic animal comprises a region encoding a gene product which modulates transcription of at least one hypertrophy-sensitive gene in cardiomyocytes, wherein the region encoding the gene product is operably linked to a heterologous TRE and the region encoding the gene product is mutated such that the encoded gene product is constitutively active in cardiomyocytes.

In other embodiments, the construct for use in generating a transgenic animal comprises a region encoding a gene product which modulates transcription of at least one hypertrophy-sensitive gene in cardiomyocytes, wherein the region encoding the gene product is operably linked to a heterologous ThE and wherein transcription of the region encoding the gene product is inducible. Inducible systems are known in the art and are described herein.

In other embodiments, the construct for use in generating a transgenic animal comprises a region encoding a gene product which modulates transcription of at least one hypertrophy-sensitive gene in cardiomyocytes, wherein the gene product is a dominant negative mutant.

DNA clones for microinjection can be prepared by any means known in the art. For example, DNA clones for microinjection can be cleaved with enzymes appropriate for removing the bacterial plasmid sequences, and the DNA fragments electrophoresed using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elute-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA.

Other methods for purification of DNA for microinjection are described in Hogan et al. *Manipulating the Mouse Embryo* (Cold Spring Harbor Laboratory, Cold Spring Harbor, N.Y., 1986), in Palmiter et al. *Nature* 300:611–615 (1982); in *The Qiagenologist, Application Protocols*, 3rd edition, published by Qiagen, Inc., Chatsworth, Calif.; and in Sambrook et al. *Molecular Cloning: A Laboratory Manual* (Cold Spring Harbor Laboratory, Cold Spring Harbor, N.Y., 1989).

Testing Transgene Constructs in Cell Culture

The transgene constructs can be tested, if desired, for activity in in vitro culture, as described in the Examples. TRE activity can be tested, for example, by introducing into cultured cardiomyocytes a polynucleotide construct comprising a TRE operably linked to a gene whose ability to modulate the transcription of at least one gene that is expressed in cardiomyocytes in response to a hypertrophic signal is to be tested, and monitoring the expression of the hypertrophy-sensitive gene or genes. Alternatively, the activity of a TRE can be tested by introducing into cultured cardiomyocytes a polynucleotide construct comprising a TRE operably linked to a reporter gene which provides for a detectable, desirably quantifiable, signal.

The sequence(s) to be tested can be inserted into a vector such that they are operably linked to an appropriate reporter gene encoding a reporter protein, including, but not limited to, chloramphenicol acetyl transferase (CAT), β-galactosidase (encoded by the lacZ gene), luciferase, (encoded by the luc gene), alkaline phosphatase, green fluorescent protein, and horse radish peroxidase. Such vectors and assays are readily available, from, inter alia, commercial sources. Plasmids thus constructed are transfected into a suitable host cell to test for expression of the reporter gene as controlled by the TRE using transfection methods known in the art, such as calcium phosphate precipitation, electroporation, liposomes (lipofection), and DEAE dextran.

The construct can be prepared in accordance with conventional ways, introducing each of the components of the construct into a plasmid by employing convenient restriction sites, PCR to introduce specific sequences at the termini, which may include restriction sites, and the like. After the expression construct has been prepared, it can be introduced into the cells by any convenient means.

Methods for introducing the expression construct into cells include transfection, complexing with cationic compounds, lipofection, electroporation, and the like. An expression construct can be introduced into a cell in association with any of the delivery vehicles, including viral and non-viral delivery vehicles, as described below. Following introduction of the expression construct into the cells, expression of the reporter gene can be determined by conventional means. Any assay which detects a product of the reporter gene, either by directly detecting the protein encoded by the reporter gene or by detecting an enzymatic product of a reporter gene-encoded enzyme, is suitable for use in the present invention. Assays include calorimetric, fluorimetric, or luminescent assays or even, in the case of protein tags, radioimmunoassays or other immunological assays. Transfection efficiency can be monitored by co-transfecting an expression construct comprising a constitutively active promoter operably linked to a reporter gene.

The activity of a TRE in a TRE-reporter gene construct can be assessed after transient expression, or stable cell lines can be created. If a stable cell line is to be created, then the construct also contains a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g., ampicillin, neomycin, methotrexate or tetracycline, complement auxotrophic deficiencies, or supply critical nutrients not available from complex media. Alternatively, the selectable marker can be contained on a construct separately from the construct containing the TRE-reporter gene, and the two constructs introduced simultaneously into host cells.

To assess the ability of one or more gene products to modulate the activity of a TRE, an expression construct comprising a gene encoding a product to be tested can be co-transfected into cardiomyocytes along with the TRE-reporter gene construct. The effect of the gene product on the expression of the reporter gene can then be assessed as described above.

To assess the ability of one or more gene products to modulate the transcription of one or more hypertrophy-sensitive genes, an expression construct comprising a TRE from a hypertrophy-sensitive gene can be operably linked to a reporter gene as described above, and introduced into cells as described above. Expression constructs comprising a gene encoding a product whose ability to modulate transcription of the one or more hypertrophy-sensitive genes is to be tested can be co-transfected into the cells. The effect of the gene product on the expression of the reporter gene can then be assessed as described above.

Optionally, additional agents can be added to the culture medium such as receptor agonist and antagonists, including, but not limited to, adrenergic receptor agonists or antagonists. The effect, if any, on transcription of a hypertrophy-sensitive gene can be measured as described above.

Agonists and antagonists suitable for use in the present invention include, but are not limited to, β1-specific agonists such as albuterol (ALB) and dobutamine (DOB); β1-specific antagonists such as metoprolol (MET); α1-specific agonists such as phenylephrine (PE); α1-specific antagonists such as prazosin; mixed β agonists such as isoproterenol (ISO); mixed β antagonists such as propanolol (PROP); and Angiotensin II.

Delivery of Polynucleotide Constructs into Cells

A polynucleotide construct can be introduced into a cell in a variety of ways. Delivery vehicles suitable for delivery of a polynucleotide into a cell (whether in vivo, ex vivo, or in vitro) include viral and non-viral delivery vehicles. Generally, a polynucleotide sequence will be operably linked to a transcriptional regulatory element (TRE) and a heterologous polynucleotide. A polynucleotide comprising a coding region encoding a gene product which modulates transcription of at least one gene that is expressed in cardiomyocytes in response to a hypertrophic signal, or a polynucleotide comprising a hypertrophy-sensitive gene can be contained within a cloning or expression vector, using methods well known in the art. These vectors (especially expression vectors) can in turn be manipulated to assume any of a number of forms which may, for example, facilitate delivery to and/or entry into a cell. Delivery of the polynucleotide constructs of the invention to eukaryotic cells, particularly to mammalian cells, more particularly to cardiomyocytes, can be accomplished by any suitable art-known method. Delivery can be accomplished in vivo, ex vivo, or in vitro.

Delivery vehicles suitable for incorporation of a polynucleotide for introduction into a host cell include non-viral vehicles and viral vectors. Verma and Somia (1997) *Nature* 389:239–242.

A wide variety of non-viral vehicles for delivery of a polynucleotide are known in the art and are encompassed in the present invention. A polynucleotide can be delivered to a cell as naked DNA (WO 97/40163). Alternatively, a polynucleotide can be delivered to a cell associated in a variety of ways with a variety of substances (forms of delivery) including, but not limited to cationic lipids; biocompatible polymers, including natural polymers and synthetic polymers; lipoproteins; polypeptides; polysaccharides; lipopolysacchaides; artificial viral envelopes; metal particles; and bacteria. A delivery vehicle can be a microparticle. Mixtures or conjugates of these various substances can also be used as delivery vehicles. A polynucleotide can be associated non-covalently or covalently with these various forms of delivery. Liposomes can be targeted to a particular cell type, e.g., to a cardiomyocyte.

Viral vectors include, but are not limited to, DNA viral vectors such as those based on adenoviruses, herpes simplex virus, poxviruses such as vaccinia virus, and parvoviruses, including adeno-associated virus; and RNA viral vectors, including, but not limited to, the retroviral vectors. Retroviral vectors include murine leukemia virus, and lentiviruses such as human immunodeficiency virus. Naldini et al. (1996) *Science* 272:263–267.

Non-viral delivery vehicles comprising a polynucleotide can be introduced into host cells and/or target cells by any method known in the art, such as transfection by the calcium phosphate coprecipitation technique; electroporation; electropermeabilization; liposome-mediated transfection; ballistic transfection; biolistic processes including microparticle bombardment, jet injection, and needle and syringe injection; or by microinjection. Numerous methods of transfection are known to the skilled worker in the field.

Viral delivery vehicles can be introduced into cells by infection. Alternatively, viral vehicles can be incorporated into any of the non-viral delivery vehicles described above for delivery into cells. For example, viral vectors can be mixed with cationic lipids (Hodgson and Solaiman (1996) *Nature Biotechnol.* 14:339–342); or lamellar liposomes (Wilson et al. (1977) *Proc. Natl. Acad. Sci. USA* 74:3471–3475; and Faller et al. (1984) *J. Virol.* 49:269–272).

For in vivo delivery, the delivery vehicle(s) can be introduced into an individual by any of a number of methods, each of which is familiar in the art.

Animal Sources

Animals which are suitable for the generation of transgenic animals of the present invention are non-human animals, preferably mammals, and include, but are not limited to, mice, rats, rabbits, pigs, cows and sheep.

Animals suitable for transgenic experiments can be obtained from standard commercial sources such as Charles River (Wilmington, Mass.), Taconic (Germantown, N.Y.), and Harlan Sprague Dawley (Indianapolis, Ind.). For example, if the transgenic animal is a mouse, many mouse strins are suitable, but C57BL/6 female mice are preferred for embryo retrieval and transfer. C57BL/6 males can be used for mating and vasectomized C57BL/6 studs can be used to stimulate pseudopregnancy. Vasectomized mice and rats can be obtained from the supplier.

Transgenic Animals

Transgenic animals can be made by any known procedure, including microinjection methods, and embryonic stem cells methods. The procedures for manipulation of the rodent embryo and for microinjection of DNA are described in detail in Hogan et al., *Manipulating the Mouse Embryo* (Cold Spring Harbor Laboratory, Cold Spring Harbor, N.Y., 1986), the teachings of which are generally known and are incorporated herein.

As an example of microinjection, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable stains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infindibulum and the embryos transferred. After the transfer, the incision is closed by two sutures.

Identification and Characterization of Transgenic Animals

Transgenic animals can be identified by analyzing their DNA. For this purpose, when the transgenic animal is a rodent, tail samples (1 to 2 cm) can be removed from three week old animals. DNA from these or other samples can then be prepared and analyzed by Southern blot, PCR, or slot blot to detect transgenic founder ($F_0$) animals and their progeny ($F_1$ and $F_2$).

1. Pathological studies

The various F0, F1 and F2 animals that carry a transgene can be analyzed by any of a variety of techniques, including immunohistology, electron microscopy, electrocardiography and making determinations of total and regional heart weights, measuring cardiomyocyte cross-sectional areas and determining numbers of cardiomyocytes. Immunohistological analysis for the expression of a transgene by using an antibody of appropriate specificity can be performed using known methods. Morphometric analyses to determine regional weights, cardiomyocyte cross-sectional areas and numbers of cardiomyocyte nuclei can be performed using known methods. Hearts can be analyzed for function, histology and expression of fetal cardiac genes.

2. Analysis of Transgene Expression by Measuring mRNA Levels

Messenger RNA can be isolated by any method known in the art, including, but not limited to, the acid guanidinium thiocyanate-phenol:chloroform extraction method (Chomczynski and Sacchi (1987) *Anal. Biochem.* 162:156–159), from cell lines and tissues of transgenic animals to determine expression levels by Northern blots, RNAse, quantitative PCR, and nuclease protection assays.

3. Analysis of Transgene Expression by Measuring Protein Levels

Protein levels can be measured by any means known in the art, including, but not limited to, western blot analysis, ELISA and radioimmunoassay, using one or more antibodies specific for the protein encoded by the transgene.

For Western blot analysis, protein fractions can be isolated from tissue homogenates and cell lysates and subjected to Western blot analysis as described by, for example, Harlow et al. *Antibodies: A Laboratory Manual*, (Cold Spring Harbor, N.Y., 1988).

For example, the protein fractions can be denatured in Laemmli sample buffer and electrophoresed on SDS-Polyacrylamide gels. The proteins are then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of the transgene-encoded proteins.

Crossing Transgenic Animals

The present invention further provides transgenic non-human animals that are progeny of crosses between a transgenic animal of the invention and a second animal. The transgenic animals of the present invention can be bred with other animals to identify other factors that influence the hypertrophic response and which could also serve as targets for drugs. Transgenic animals can be bred with other transgenic animals, where the two transgenic animals were generated using different transgenes, to test the effect of one gene product on another gene product or to test the combined effects of two gene products.

In some embodiments, a first transgenic animal comprising as a transgene a polynucleotide encoding a gene product which increases transcription of at least one cardiac hypertrophy-sensitive gene operably linked to a heterologous, cardiomyocyte-specific TRE, wherein expression of the transgene is embryonic lethal, or otherwise deleterious such that the animals do not survive long enough for analysis, the transgene can be placed under transcriptional control of an inducible promoter, such as the tet inducible system described above, such that the transgene is substantially not expressed until desired. Such animals can be crossed with a tTA constitutive "founder" trasgenic animal, which comprises as a transgene a polynucleotide comprising a tTA under tetracycline control.

In other embodiments, a first transgenic animal, comprising as a transgene a polynucleotide encoding a gene product that increases transcription of at least one cardiac hypertrophy-sensitive gene operably linked to a heterologous, cardiomyocyte-specific TRE, such that the first animal displays one or more symptoms of cardiac hypertrophy, is crossed with a second transgenic animal comprising as a transgene a dominant negative mutant of a gene product which increases transcription of at least one cardiac hypertrophy-sensitive gene. The progeny of such a cross would display a reduction of one or more symptoms associated with cardiac hypertrophy.

In other embodiments, a first transgenic animal, comprising as a transgene a polynucleotide encoding a gene product which decreases or represses transcription of at least one cardiac hypertrophy-sensitive gene operably linked to a heterologous, cardiomyocyte-specific TRE, such that the first animal does not display a symptom of cardiac hypertrophy and is substantially resistant to developing cardiac hypertrophy, is crossed with a second transgenic animal comprising as a transgene a polynucleotide encoding a constitutively active mutation of a gene product which increases transcription of at least one cardiac hypertrophy-sensitive gene.

In other embodiments, a first transgenic animal, comprising as a transgene a polynucleotide which is an antisense polynucleotide targeted to a gene product which modulates transcription of at least one cardiac hypertrophy-sensitive gene, is crossed with a second transgenic animal comprising as a transgene a polynucleotide encoding a constitutively active mutation of a gene product which increases transcription of at least one cardiac hypertrophy-sensitive gene, wherein the antisense polynucleotide inhibits expression of the transgene of the second transgenic animal.

Screening of Substances for Treatment of Cardiac Hypertrophy

The transgenic animals, animal cells isolated from transgenic animals, or isolated enzymes can be used to screen substances for a potential effect in the treatment of cardiac hypertrophy.

Enzyme-based screening assays

In enzyme-based screening assays, substantially isolated enzymes involved in response to a hypertrophic signal in cardiomyocytes are contacted with a substance to be tested. Activity of the enzyme is measured in the presence of the substance, after a suitable time. Conditions and times sufficient for interaction of an enzyme agonist or antagonist candidate with the enzyme will vary with the enzyme, however, conditions generally suitable for binding occur between about 4° C. and about 40° C., preferably between about 4° C. and about 37° C.; in a buffered solution containing appropriate ions in an appropriate concentration range, which may vary for a given enzyme; and within a pH range of between 5 and 9. Sufficient time for the binding and response will generally be between about 1 millisecond and about 24 hours after exposure.

Enzyme activity in the presence of the substance being tested is compared with the activity in the absence of the substance being tested. An increase or decrease in the activity being measured is an indication that the substance is suitable for use in reducing a cardiac hypertrophy-induced dysfunction. A substance is considered to have an effect on enzyme activity if the activity being measured is increased or decreased at least about 2-fold, more preferably at least about 5-fold, more preferably at least about 10-fold or more, relative to the activity of the enzyme activity measured in the absence of the substance being tested. The substance can be further tested in a cell based and/or whole animal-based assay, as described below.

Enzymes which are involved in a response to a hypertrophic signal in cardiomyocytes include, but are not limited to, calcineurin, CaMKIV, CaMKIIα, p38, YY1, a CaMK kinase, and MKK6. Enzymes can be used in their native form; in mutated forms having altered enzymatic activities and/or in vitro stability or solubility; in mutant forms in which a regulatory or other component of the enzyme is absent, but the enzyme retains an enzymatic activity related to response to a hypertrophic signal; covalently or non-covalently associated with another molecule to confer in vitro stability, to facilitate attachment to a solid support, to provide an antigenic determinant, and the like. The enzymes can be conjugated to a label capable of producing a detectable signal or other functional moieties. Suitable labels include, but are not limited to, radionuclides, other enzymes, substrates, cofactors, inhibitors, fluorescent dyes, chemiluminescent dyes, bioluminescent compounds and magnetic particles.

Preferably, for use in a screening assay, an enzyme is substantially purified. A "substantially isolated" or "purified" enzyme is one that is substantially free of the materials with which it is associated in nature, particularly of other proteinaceous material or substances which may inhibit an enzymatic activity related to a response to a hypertrophic signal. By substantially free is meant at least 50%, preferably at least 70%, more preferably at least 80%, and even more preferably at least 90% free of the materials with which it is associated in nature. As used herein, a "substantially isolated" enzyme also refers to recombinant enzymes, which, by virtue of origin or manipulation: (1) are not associated with all or a portion of an enzyme with which it is associated in nature, (2) are linked to a polypeptide other than that to which it is linked in nature, or (3) does not occur in nature.

Enzymes for use in these assays are obtainable by any method known in the art, including, but not limited to, natural sources, chemical synthesis or recombinant techniques. An enzyme for use in the screening assays of the invention can be purified by any known method. A wide variety of methods are known in the art. See, for example, *Protein Purification: Principles and Practice*, R. Scopes, ed. (1987) Springer-Verlag.

Enzyme activity can be determined by any known method. For example, kinase activity of p38 can be measured by incubating the enzyme together with a protein substrate and $\gamma^{32}P$-ATp, and detecting $^{32}P$ incorporation into the substrate, for example, by scintillation counting. Assays for p38 kinase activity have been described. See, for example, PCT Publication No. WO 98/27098.

Cell-based screening assays

In the cell-based screening assays of the present invention, the compound to be tested is introduced into the culture media of cells, over period of time and in various dosages, then the cells are examined for one or more functions, including, but not limited to, changes in expression levels of a hypertrophy-sensitive gene, changes in levels of a polypeptide product of a hypertrophy-sensitive gene, and changes in cell size and/or morphology.

Screening assays for determining the therapeutic potential of compounds can be performed using animal cells derived from transgenics for the disclosed transgene constructs in cell cultures and stably or transiently transfected with the disclosed constructs. Cell-based screening assays can also be performed using primary cells, such as cardiomyocytes, derived from a non-transgenic animal, the cells being stably or transiently transfected with the polynucleotide constructs, or being stimulated with hypertrophic signals such as Angiotensin II or α-adrenergic agonists.

To detect a change in levels of a polypeptide product of a hypertrophy-sensitive gene, a variety of assay methods can be used, each of which is known in the art. For example, an immunological assay such as an ELISA can be used, employing one or more antibodies specific for one or more polypeptide products of a hypertrophy-sensitive gene.

To detect a change in expression levels of a hypertrophy-sensitive gene, any known method can be used, including, but not limited to, hybridization with a polynucleotide probe which is complementary to an RNA product of the gene; and a polymerase chain reaction using oligonucleotide primers that prime extension of a cDNA copy of an RNA product of the gene. Nucleotide sequences of some hypertrophy-sensitive genes have been disclosed, and this information can be used to design oligonucleotide primers.

Alternatively, the cells can be transfected with a reporter gene construct comprising a reporter gene operably linked to a TRE, particularly one derived from a hypertrophy-sensitive gene. In these assays, the readout from these assays is level of active reporter gene product. Nucleotide sequences of 5' flanking regions of some hypertrophy-sensitive gene have been disclosed, and can be used to generate constructs comprising a cardiac hypertrophy-sensitive gene TRE operably linked to a reporter gene. Such nucleotide sequences include, for example, rat ANF 5' flanking sequences (GenBank Accession No. J03267); and mouse β-MHC 5' flanking sequences (GenBank Accession No. U86076).

The cell-based screening assays described herein can be used as primary screens, or alternatively, as secondary screens to further test compounds which are active in an above-described enzyme-based screen.

For these assays, suitable cells include, but are not limited to, primary cardiomyocytes, isolated from either transgenic or non-transgenic animals. Other cells suitable for use in cell-based screening assays include non-cardiomyocyte cell types such as fibroblasts.

In some embodiments, cells are transfected with a construct comprising a TRE from a hypertrophy-responsive gene operably linked to a reporter gene. Reporter genes are known in the art and described above. One example is a green fluorescent protein (GFP) and variants thereof. See, for example, Heim and Tsien (1996) *Curr. Biol.* 6:178–182; Mitra et al. (1996) *Gene* 173:13–17; and Yang et al. (1996) *Nucl. Acids Res.* 24:4592–4593. The transfected cells are then placed in 96-well culture plates at 1.5 to $2.5 \times 10^4$ cells per well in a suitable culture medium, such as Dulbecco's minimal essential medium plus 10% fetal bovine serum. Following overnight incubation at 37° C. in an incubator equilibrated with 5% carbon dioxide, media are removed and replaced with media containing a compound to be tested and incubated for a suitable period of time. For the present invention, a suitable time period for incubation with a substance to be tested can be from about 0.5 hours to about 24 hours. In addition to the test compound, a hypertrophy-inducing substance is added to the culture medium. The hypertrophy-inducing substance can be added simultaneously with, before, or after, addition of the test substance. Hypertrophy-inducing substances include, but are not limited to, angiotensin II and PE. Stocks containing the compound to be tested are first prepared in suitable solvent. Several dilutions of the test compound are tested. Appropriate controls include cells to which solvent containing no test substance is added, and cells to which a test substance was added, but to which no hypertrophy-inducing substance is added.

After treatment, an effect of the test compound is measured using a suitable assay for the reporter gene product.

Reporter genes which may be employed are well known and include, but are not limited to, luciferase; a green fluorescent protein (GFP), for example, a GFP from *Aequorea victoria*, or any of a variety of GFP known in the art; β-galactosidase, chloramphenicol acetyl transferase; immunologically detectable protein "tags" such as human growth hormone; and the like. See, for example, Current Protocols in Molecular Biology (F. M. Ausubel et al., eds., 1987) and periodic updates.

Any assay which detects a product of the reporter gene, either by directly detecting the protein encoded by the reporter gene or by detecting an enzymatic product of a reporter gene-encoded enzyme, is suitable for use in the present invention. Assays include colorimetric, fluorimetric, or luminescent assays or even, in the case of protein tags, radioimmunoassays or other immunological assays.

A substance is considered to have an effect if transcription of the operably linked reporter gene is increased or decreased in cells at least about 2-fold, more preferably at least about 5-fold, more preferably at least about 10-fold or more, relative to control cells which were not exposed to the substance.

Cytotoxic effects of the substances can be measured by any means known in the art. For example, cytotoxic effects of the substances can be measured by a modification of the method of Hansen et al. (1989) *J. Immunol. Method.* 119:203–210. To the cells remaining in the tissue culture plate, 25 $\mu$L of a 3,(4,5-dimethylthiazol-2-yl)2,5-diphenyltetrazolium bromide (MTT) stock solution (5 mg/mL) is added to a final concentration of 1 mg/mL. Cells are incubated at 37° C. for one hour, and cellular activity is stopped by the addition of an equal volume of MTT lysis buffer (20% w/v sodium dodecylsulfate in 50% dimethylformamide, pH 4.7). Complete extraction is achieved by overnight shaking at room temperature. The difference in the $OD_{562nm}$ and the $OD_{650nm}$ is measured in a Molecular Device's $UV_{max}$ microplate reader, or equivalent, as an indicator of the cellular viability. Other assays for cell viability include trypan blue exclusion.

Whole animal-based screening assays

In the whole animal-based screening assays of the present invention, the compound is administered to a transgenic animal of the present invention, over period of time and in various dosages, then the animals are examined for cardiac function, as measured by various parameters including, but not limited to, left ventricular mass:body weight ratio; cardiomyocyte size and organization; cardiac hypertrophy-sensitive gene expression; cardiac function; dP/dT; fibroid deposition; calcium ion flux; stroke length; and ventricular output. A whole-animal based assay can be used as a primary screen, or can be used as a secondary screen to further evaluate substances identified in an enzyme- and/or cell-based screen. In some embodiments, parts of a transgenic animal of the invention can be used in an in vitro screening assay. For example, a heart isolated from a transgenic animal can be used in an in vitro screening assay. Parameters which can be measured are as for whole animal drug screens.

Assays to detect proteins which interact with enzymes involved in response to a hypertrophic signal The enzyme targets used in the enzyme-based screening assays described above are also useful for identifying other factors, which may be polypeptides, that interact with the enzyme target. Such factors can then be evaluated for their utility as therapeutic targets in treating a cardiac hypertrophy-induced dysfunction. Such factors can also be analyzed for a potential role in modulating a biological function of the target gene product.

Any known method can be used to identify polypeptides which interact with an enzyme target. Suitable assays include in vitro and in vivo assays. In vitro assays include, but are not limited to, co-precipitation, protein interactive trapping, and ELISA. Assays can be designed to identify compounds that bind to target gene products, bind to other cellular or extracellular proteins that interact with a target gene product, and interfere with the interaction of a target gene product with other cellular proteins.

As an example of protein interactive trapping, a yeast two-hybrid screen can be performed using mouse GATA4 as bait to identify potential interacting factors in the adult myocardium, as described. Molkentin et al. (1998) *Cell* 93:215–228. In this example, the GATA4 bait contains amino acids 130–409 fused in-frame with the GAL4 DNA binding domain. This region of GATA4 encompasses the two zinc finger domains and is encoded within a PstI-NsiI fragment, which was cloned into a Pst I site in the pAS yeast expression vector. pAS-GATA4 was co-transformed into yeast with an adult mouse heart library that contained the GAL4 activation domain fused to random cDNAs and over 5 million primary colonies were screened for positive interactions. Approximately 100 positive yeast colonies were initially identified. From each individual colony, the activating plasmid was rescued and the cDNA insert was sequenced. Clones containing cDNA inserts in the antisense orientation or out-of-frame were discarded. The remaining clones (approximately 21) were retransformed back into yeast to test for specificity.

Specificity of binding can be determined using the following criteria: 1) the isolated clone should recapitulate the interaction with the original bait; 2) the isolated clone should not interact with a nonspecific bait, in this case a GAL4-E12 fusion. As a further test of specificity, one can test interaction with related proteins that share a high degree of amino acid sequence homology.

Use of Transgenic Animal or Cells Derived Therefrom

The transgenic animals produced in accordance with the invention are especially useful for screening and identifying or testing substances or potential drugs for treating hypertrophic cardiomyopathies and/or for research in connection with hypertrophic cardiomyopathies with the object of developing improved therapeutic treatments or diagnostic methods applicable in human medicine.

Substances to be tested include naturally-occurring and synthetic substances. These substances include not only natural and synthetic inorganic and organic compounds based on various core structures, but also oligomers, such as oligopeptides and oligonucleotides. Various natural sources can be screened for active compounds, including those found in jungles, the ocean, and the like. In addition, combinatorial libraries of compounds can be generated and tested. Also to be included for testing are antibodies to a gene product, particularly a polypeptide, of a gene involved in modulating transcription of a cardiac hypertrophy-sensitive gene.

Compositions Comprising Substances Useful for Treatment of Cardiac Hypertrophy or Cardiac Failure The present invention provides compositions comprising a substance for use in treating a cardiac hypertrophy-induced dysfunction. For the purposes of this invention, a substance for use in treating a cardiac hypertrophy-induced dysfunction is one that modulates levels of an active product of at least one gene that is expressed in cardiomyocytes in response to a hypertrophic signal. Substances which are suitable include natural or synthetic organic or inorganic compounds that 1) modulate the expression of a hypertrophy-sensitive gene; 2) modulate the expression of a gene whose product modulates the expression of a hypertrophy-sensitive gene; and/or 3) modulate an activity of a gene product which modulates the expression of a hypertrophy-sensitive gene. A "substance" also includes a polynucleotide that 1) modulates the expression of a hypertrophy-sensitive gene; 2) modulates the expression of a gene whose product modulates the expression of a hypertrophy-sensitive gene; 3) modulates the level of active product of at least one gene that is expressed in cardiomyocytes in response to a hypertrophic signal.

An "effective amount" of a substance is that amount required to achieve amelioration or palliation of cardiac hypertrophy or other condition being treated by the methods of the present invention.

The present invention also encompasses the use of known substances to treat cardiac hypertrophy. Such substances include, but are not limited to, the calcineurin inhibitors FK506 and cyclosporin and related drugs. These drugs are routinely used as immunosuppressants in transplant patients but have not yet been used to treat cardiac hypertrophy or heart failure. "Cyclosporins" are cyclic undecapeptides. A variety of cyclosporins which inhibit phosphatase activity of CaN have been described and are encompassed in the term "cyclosporin". These include, but are not limited to, cyclosporin A; derivatives of cyclosporin A, including, but not limited to, (O-(2-hydroxyethyl)-D-ser)8 and (3'-deshydroxy-3'-keto-MeBmt)1-(Val)2 derivatives (U.S. Pat. Nos. 5,284,826 and 5,525,590); and cyclosporin G. Pharmaceutical formulations of cyclosporin which may be suitable for use in the treatment methods of the present invention include, but are not limited to, those described in UK Patent Publication No. GB 2,257,359; PCT Publication Nos. WO 95/34285 and WO 97/07787; and U.S. Pat. Nos. 5,739,105 and 5,641,745. FK596 is a macrocyclic lactone. The term "FK506", as used herein, includes FK506 and derivatives that inhibit a phosphatase activity of CaN, including, but not limited to, derivatives disclosed in U.S. Pat. Nos. 5,530,120 and 5,493,019. Also included are substances which are inhibitors of CaMKIV, including KN62, KN93, and related drugs which inhibit kinase activity of CaMKIV. Further included are inhibitors of p38 kinase, such as those described in PCT Publication No. WO 98/27098.

Substances which have potential for treatment of cardiac hypertrophy and heart failure include substances which enhance the expression of one or more gene products which normally repress transcription of at least one gene that is expressed in cardiomyocytes in response to a hypertrophic signal, thereby reducing the expression of the at least one gene that is expressed in cardiomyocytes in response to a hypertrophic signal. For example, the transcription factor YY1 has been discovered to be a global repressor of cardiac hypertrophic responsive genes. Over-expression of YY1 in cultured cardiomyocytes prevents cardiac hypertrophy and silences all hypertrophy-sensitive gene expression. Substances which are regulators of YY1 can then potentially be used to regulate cardiac hypertrophy, cardiomyocyte growth and cardiac function. As a further example, constitutively active CaMKIIα silences all hypertrophy-sensitive genes in cardiomyocyte cultures. Substances that activate CaMKIIα have potential to regulate cardiac hypertrophy.

Substances which have potential for treatment of cardiac hypertrophy and heart failure include also include substances which reduce the expression of one or more gene products which normally increase transcription of at least one gene that is expressed in cardiomyocytes in response to a hypertrophic signal, thereby reducing the expression of the at least one gene that is expressed in cardiomyocytes in response to a hypertrophic signal.

Compositions within the scope of the invention include compositions wherein the active ingredient is contained in an effective amount to alleviate the symptoms of the condition being treated. Determination of the effective amounts can readily be determined empirically by those of ordinary skill of the art.

A substance of the present invention can be administered alone or together with other drug therapies, including, β-adrenergic receptor antagonists, endothelin receptor antagonists, ACE inhibitors, and the like. ACE inhibitors include drugs designated by the trademarks Accupril®, Altace®, Capoten®, Lotensin®, Monopril®, Prinivil®, Vasotec®, and Zestril®.

Pharmaceutical compositions are prepared using a substance or by combining a substance to the appropriate carrier, which itself can be an immunological adjuvant. These compositions can be administered by any means that achieves the intended purpose. For example, administration can be subcutaneous, cutaneous, intravenous, intradermal, intramuscular, or intraperitoneal.

The amount of the substance administered as well as the frequency of administration is dependent upon the age, sex, health and weight of the recipient as well as the nature of the effect desired.

In addition to the substance identified by the screening methods of the present invention, these pharmaceutical compositions can contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to 99 percent by weight, and preferably from about 25 to 85 percent by weight, of active ingredient, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture, and processing the mixture of granules, after adding suitable auxiliaries, if desired or necessary, to obtain tablets or dragee cores.

Suitable excipients are, in particular, fillers such as sugars, for example, lactose, sucrose, mannitol, or sorbitol, cellulose preparations and/or calcium phosphate, such as tricalcium phosphate or calcium hydrogen phosphate, as well as binders such as starch paste using, for example, maize starch, wheat starch, rice starch, potato starch, gelatin, gum tragacanth, methyl cellulose, hydroxypropylcellulose, sodium carboxymethylcellulose, and/or polyvinyl pyrrolidone. If desired, disintegrating agents can be added, such as the above-mentioned starches and derivatives thereof, as well as carboxymethyl starch, cross-linked polyvinylpyrrolidone, agar, or alginic acid or a salt thereof such as sodium alginate. Auxiliaries include flow-regulating agents and lubricants, such as silica, talc, stearic acid or salts thereof such as magnesium or calcium stearate, and/or polyethylene glycol. Dragee cores can be provided with suitable coatings which, if desired, are resistant to gastric juice. For this purpose, concentrated sugar solutions can be used, which can optionally contain gum Arabic, talc, polyvinyl pyrrolidone, polyethylene glycol, and/or titanium dioxide, lacquer solutions, and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dyestuffs or pigments can be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers can be added.

Pharmaceutical preparations which can be administered rectally include suppositories, which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a suitable base. Suitable base materials include, for example, liquid triglycerides, polyethylene glycols, and paraffin hydrocarbons.

A variety of devices are known which allow controlled delivery of a substance to a tissue. Suitable examples of sustained-release preparations include semipermeable matrices of solid hydrophobic polymers containing the protein, which matrices are in the form of shaped articles, e.g., films, or microcapsules.

Suitable formulations for parenteral administration include aqueous solutions of the active compounds in water-soluble form. In addition, suspensions of the active compounds as appropriate oily injection suspensions can be administered. Suitable lipophilic solvents or vehicles include fatty oils, such as sesame oil, or synthetic fatty acid esters, such as ethyl oleate or triglycerides. Aqueous injection suspensions can contain substances which increase the viscosity of the suspension, such as sodium carboxymethyl cellulose, sorbitol, and/or dextran. Optionally, the suspension can contain stabilizers.

Pharmaceutical excipients are well known in the art and need not be described in detail herein. See, for example, *Remington: The Science and Practice of Pharmacy* (19$^{th}$ edition, 1995), Gennaro, ed.

Methods of Treating a Cardiac Hypertrophy-induced Dysfunction

The present invention provides methods for treating a cardiac hypertrophy-induced dysfunction, comprising administering to an individual (a "subject") in need thereof an amount of a substance effective to diminish or reverse progression of the dysfunction. As described above, for use in the methods described herein, a "substance" includes a natural or synthetic organic or inorganic compound that 1) modulates the expression of a hypertrophy-sensitive gene; 2) modulates the expression of a gene whose product modulates the expression of a hypertrophy-sensitive gene; or 3) modulates an activity of a gene product which modulates the expression of a hypertrophy-sensitive gene.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. As used herein, the term "treatment" includes prophylaxis.

"Palliating" a disease means that the extent and/or undesirable clinical manifestations of a disease state are lessened and/or time course of the progression is slowed or lengthened, as compared to not a substance detected by the methods of the present invention.

The methods comprise administering to an individual (a "subject") in need thereof an amount of a substance effective to diminish or reverse progression of the dysfunction. In the context of prophylaxis, a "subject in need thereof" includes, but is not limited to, individuals in the general population who are 55 years of age and older; individuals who have a genetic predisposition to developing cardiac hypertrophy; dilated cardiac myopathy patients; hypertensive patients; patients with renal failure and vascular hypertension; individuals with vascular hypertensive due to pressure overload, volume overload, or increased peripheral bed resistance; individuals with respiratory ailments such as emphysema or cystic fibrosis; chronic asthmatics; individuals with tuberculosis; and organ transplant patients.

In some embodiments, the methods involve blocking an activity of cardiac calcineurin (CaN), particularly with respect to its dephosphorylation action on cardiac transcription factors such as NFAT-3 or other NFAT family members. In some embodiments, the methods involve the use of inhibitors of CaN to block the transcriptional activation of NFAT or other nuclear transcription factors activated by CaN-mediated dephosphorylation. In other embodiments, the methods involve inhibition of CaN by clinically approved specific inhibitor drugs, including members of the immunosuppressive family of cyclosporin A derivatives, to reduce the dephosphorylation activity of CaN, in the cytosol and/or the nucleus of the cardiomyocyte. Blocking the dephosphorylation of NFAT transcription factors by immunosuppressive drugs which specifically inhibit CaN substantially reduces or prevents translocation of these transcription factors to the cardiomyocyte nuclear compartment, rendering them incompetent to form an active heteroduplex with GATA4. The inability to form the NFAT-3/GATA-4 heteroduplex or similar complexes between activated NFAT members and GATA transcription factors prevents such complexes from binding to their specific enhancer sites on a number of hypertrophy-sensitive cardiac promoters. Since a number of cardiac hypertrophy-sensitive promoters contain such binding sites and are responsive to NFAT-3/GATA-4 or similar complexes, their gene products can be up-regulated by CaN activity and therefore can be inhibited by CaN-specific immunosuppressive inhibitors.

CaN-specific immunosuppressive inhibitors block most nuclear signaling converging through CaN due to cardiovascular pressure overload-induced cardiac hypertrophy and block the transcriptional induction leading to chronic hypertrophy, in turn leading to dilated cardiac myopathy in the chronic untreated animal. In other embodiments, the use of inhibitors of CaN blocks all pressure overload membrane receptor-mediated nuclear signaling for the transcriptional induction of cardiac hypertrophy. Receptor-mediated transcriptional induction of cardiac hypertrophy through pressor agents, Angiotensin II (AngII), Endothelin-1 (ET-1) thrombin (Thrb) and alpha adrenergic signaling through the alpha-1-adrenergic receptor converge as a nuclear transcription activation signal at CaN. Because these pathways converge at CaN, pressor agent- and alpha-1-adrenergic receptor-mediated transcriptional induction of hypertrophy-sensitive cardiac genes can be blocked by CaN inhibitors.

In other embodiments, the methods inhibit the expression of gene products which are expressed in response to CaN dephosphorylation of NFAT transcription factors, i.e., gene products of hypertrophy-sensitive genes. In some of these embodiments, the agent that inhibits expression of one or more hypertrophy-sensitive genes is an antisense polynucleotide which targets a hypertrophy-sensitive gene.

In embodiments which comprise administration of an agent(s) which inhibits CaN, thereby blocking the dephosphorylation of NFAT-3 and/or one or more related family members, an agent that blocks CaN is a member of the cyclosporin family of immunosuppressive drugs, such as cyclosporin A (CsA) or FK506. Any agent that inhibits cardiac CaN activity to block the dephosphorylation of one or more NFAT transcription factor family members may prove useful.

In some embodiments, the methods administer an agent that reduces expression of cardiac CAN. Such agents include, but are not limited to, a dominant negative form of CaN (e.g., negative truncated form of the coding region of the alpha subunit of CaN); an antisense construct which targets a CaN gene; and a truncated, inactive form of the beta subunit of CaN. A truncated, inactive form of the β-subunit of CaN can sequester the active alpha subunit of CaN, and render it incompetent for activation. In other embodiments, the methods comprise administering an antibody specific for CaN, or the alpha or beta subunit thereof. In some of these embodiments, the antibody is a single chain antibody. In other embodiments, the antibody is an antibody that blocks CaN activity or prevents NFAT-3 and/or an NFAT family member from being dephosphorylated by cardiac CaN.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, a delivery system can be designed that targets such compounds to the site of affected tissue in order to minimize potential damage to non-target cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture and/or in whole animals. Such information can be used to more accurately determine useful doses in humans.

The therapeutic efficacy of a substance detected by the methods of the present invention in the treatment of cardiac hypertrophy can be accomplished by those skilled in the art using known principles of diagnosis and treatment.

The following examples are provided to illustrate, but not to limit, the present invention.

EXAMPLE 1

Inhibition of the Hypertrophic Effects of AngII and PE by CsA and FK506 in Primary Cardiomyocytes
Experimental Protocol To visualize primary cardiomyocytes and their sarcomeric organization, anti-α-actinin mouse monoclonal antibody was used (Sigma). This antibody is specific for the cardiac and skeletal α-actin proteins. Cells were washed in 1×phosphate-buffered saline (PBS), fixed in 3.7% paraformaldehyde for 5 minutes, washed three times with 1×PBS and then pre-blocked in 1×PBS containing 2% horse serum, 2% BSA, and 0.1% non-ionic detergent NP40 for 30 minutes. Anti-α-actinin antibody was added at a dilution of 1:800 in fresh preblock solution and incubated for an additional 30 minutes. Subsequently, the cells were washed three times in 1×PBS with 0.1% NP40. Anti-mouse TRITC-conjugated secondary antibody was then added at a dilution of 1:400 for 30 minutes in pre-block solution and the cells were again washed three times in 1×PBS containing 0.1% NP40. Nuclear staining for DNA was performed with 0.5 μg/ml of bisbenzimide in PBS for 15 minutes followed by three rinses with PBS.

Results

Figure 2G:
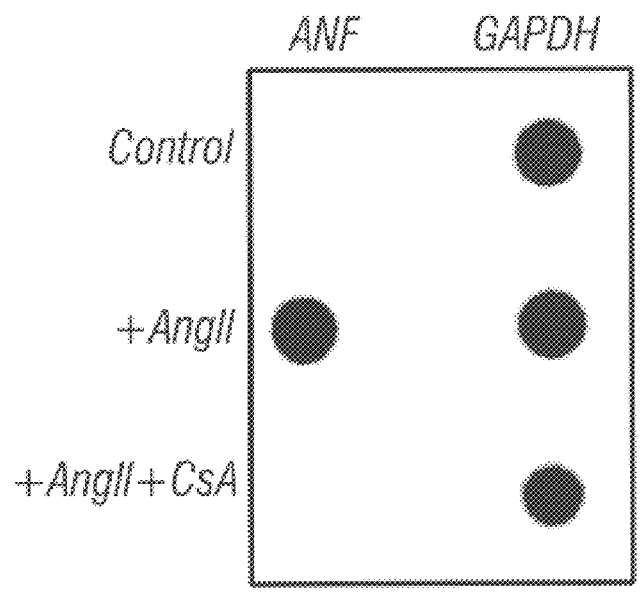
FIG. 2G, shows Total RNA was isolated from primary cardiocyte cultures treated with AngII in the presence or absence of CsA as in A and analyzed for expression of GAPDH and ANF transcripts by dot blot.
Figure 2H:
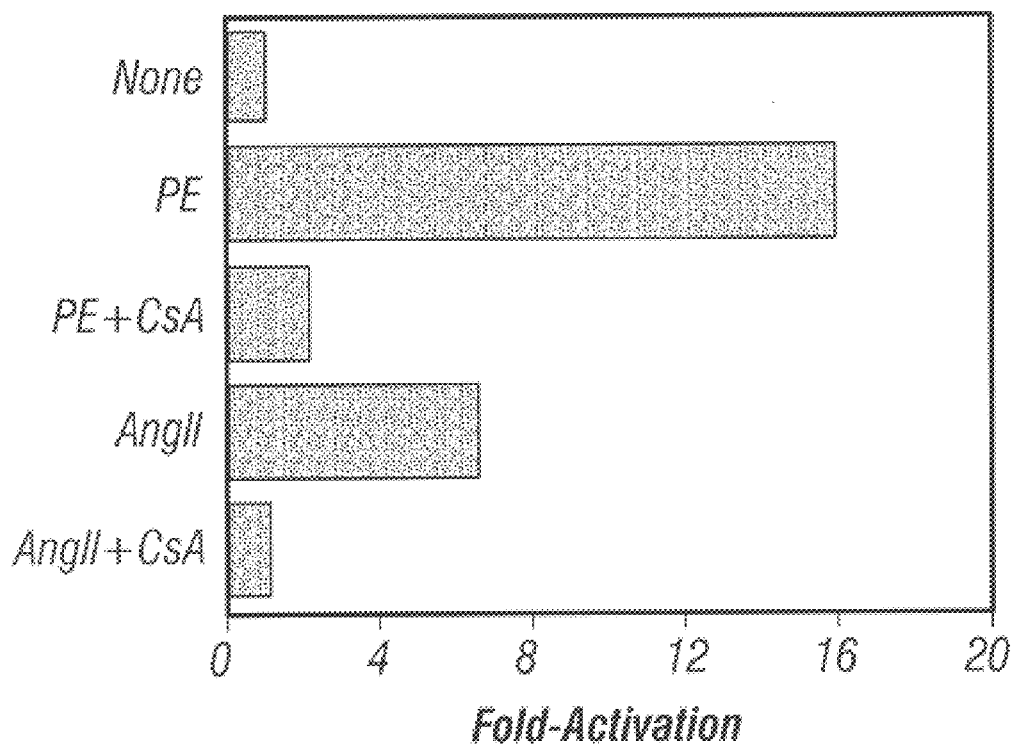
FIG. 2H, shows Primary rat cardiomyocytes were transiently transfected with a luciferase reporter gene linked to 3 tandem copies of the NF-AT consensus binding site. Cells were then treated with AngII or PE in the presence or absence of CsA, as described above. Forty-eight hours later, cells were harvested and luciferase activity was determined.

Exposure of primary cardiomyocytes to AngII and PE results in a pronounced hypertrophic response, which is characterized by an increase in cell size and sarcomeric assembly, upregulation of several fetal contractile protein genes, and enhanced contractility. These events are preceded by an increase in intracellular calcium. To determine whether the hypertrophic response of cardiomyocytes to these agonists was mediated by calcineurin, neonatal rat cardiomyocytes were exposed to AngII (10 nM) or PE (10 μM) in the presence and absence of CsA or FK506. Cardiomyocytes demonstrated a dramatic increase in size and sarcomeric assembly after 72 hr of exposure to AngII or PE (FIGS. 2B and 2E). In the presence of CsA (FIGS. 2C and 2F) or FK506, the response to AngII was completely abolished and the response to PE was dramatically reduced.

To determine whether changes in cardiomyocyte gene expression in response to AngII were also controlled by a calcineurin-dependent signaling pathway, the expression of ANF mRNA in cardiomyocytes treated with AngII was examined in the presence and absence of CsA by a dot blot assay. Exposure to AngII resulted in a 15-fold increase in atrial natriuretic factor (ANF) mRNA, which was completely blocked by CsA (FIG. 23G). GAPDH mRNA was measured as a control. Together, these morphologic and molecular data demonstrate that the AngII and PE signaling pathways are CsA-/FK506-sensitive. Because calcineurin is the only known target for inhibition by both CsA and FK506, these results suggest that calcineurin activation is a necessary step in the signaling pathway for AngII- and PE-dependent induction of cardiac hypertrophy.

EXAMPLE 2

Induction of Cardiac Hypertrophy in vivo
Experimental Protocols

Transgenic mice. Transgenic mice expressing calcineurin in the heart were created as follows. A cDNA encoding a constitutively active form of the calcineurin A catalytic subunit (O'Keefe et al. (1992) Nature 357:692–694) was cloned by PCR with a 5' SalI linker and 31 HindIII linker into an expression vector containing the α-MHC promoter. The expression pattern and characteristics of this expression vector have been described previously (Jones et al. (1994) Dev. Dyn. 200:117–128). The calcineurin-α-MHC vector was digested with NotI to liberate the pBluescript backbone and allow purification of the α-MHC-fusion cDNA fragment. This fragment was purified on an agarose gel using the Qiaex II gel extraction kit (Qiagen) and eluted in oocyte injection buffer (5 mM Tris-HCl pH 7.4 and 0.2 mM EDTA). The purified fragment was injected into recently fertilized oocytes derived from FVB mice and transferred into the oviducts of pseudopregnant ICR mice.

Transgenic mice expressing CaMKIV in the heart were created as follows. A cDNA encoding a constitutively active form of CaMKIV (O'Keefe et al. (1992) *Nature* 357:692–694) was cloned by PCR and inserted into an expression vector containing the α-MHC promoter, as described above for the calcineurin mouse. DNA was prepared for injection into oocytes, and transgenic mice were generated, as described above.

RNA analysis. Total RNA was collected and purified with Triazol reagent (Gibco BRL) as recommended. RNA from wild-type and transgenic hearts, as well as from cultured cardiomyocytes, was subjected to dot blot hybridization against a panel of oligonucleotide probes as described previously (Jones et al. (1996) *J. Clin. Invest.* 98, 1906–1917).

Histology. Hearts from wild-type and trnsgenic mice were subjected to histological analysis. Briefly, hearts were collected, fixed overnight in 10% formalin buffered with PBS, dehydrated in ethanol, transferred to xylene then into paraffin. Paraffin-embedded hearts were sectioned at 4 µm and subsequently stained with hematoxylin and eosin for routine histologic examination or with Masson trichrome for collagen (Woods and Ellis In, *Laboratory Histopathology: A Complete Reference* (1994) Churchill Livingstone Publishers pp. 7.1–13).

Results

Induction of cardiac hypertrophy in vivo by activated calcineurin. The above results indicated that calcineurin was a potent regulator of cardiac hypertrophy in cultured primary cardiomyocytes. To determine whether this signal transduction pathway could also operate in the myocardium in vivo, transgenic mice were generated that expressed the constitutively active form of the calcineurin catalytic subunit in the heart, using the a-MHC promoter to drive expression. Previous studies have shown that this cardiac-specific promoter is active in the ventricular chambers primarily after birth (Jones et al. (1994) *Dev. Dyn.* 200:117–128). A total of 10 independent founder transgenic mice were generated, which contained between 2 and 68 copies of the α-MHC-calcineurin transgenic (Table 1).

TABLE 1

Summary of α-MHC-Calcineurin Transgenic Lines

| Transgenic Line | Transgene Copy | Cause of Death | Age at Death | Heart: Body wt. | Cardiac Phenotype |
|---|---|---|---|---|---|
| 46 | 8 | Sacrificed | 18 days | 2.2 | Hypertrophic |
| 22 | 22 | Sudden | 10 weeks | 2.3 | Dilated |
| 110 | 3 | Sudden | 4 weeks | 2.6 | Hypertrophic |
| 106 | 2 | Sudden | 9 weeks | N.D. | N.D. |
| 108 | 3 | Still alive | (14 weeks) | — | — |
| 41 | 68 | Still alive | (24 weeks) | — | — |
| 37 | 15 | Still alive | (23 weeks) | — | — |
| 37-1 | 15 | Sacrificed | 5 weeks | 2.3 | Hypertrophic |
| 37-2 | 15 | Sudden | 4 weeks | N.D. | Hypertrophic |
| 37-3 | 15 | Sudden | 3 weeks | 2.5 | Hypertrophic |
| 37-4 | 15 | Still alive | (8 weeks) | — | — |
| 37-5 | 15 | Still alive | (8 weeks) | — | — |
| 37-6 | 15 | Sudden | 12 weeks | 2.9 | Dilated |
| 39 | 3 | Sudden | 11 weeks | 2.7 | Hypertrophic |
| 39-1 | 3 | Sudden | 3 weeks | N.D. | Hypertrophic |
| 39-2 | 3 | Sudden | 4 weeks | N.D. | N.D. |
| 39-3 | 3 | Still alive | (10 weeks) | — | — |

Heart:body weight (heart:body wt) ratios were calculated by weighing the hearts and bodies of nonstransgenic and transgenic litter mates. Values are expressed as the relative weight of the transgenic heart compared to nontransgenic litter mate. Ages of mice that were still alive as of Feb. 18, 1998 are shown in parenthesis. 37 and 39 were founder transgenics and mice designated as 37- and 39-were their offspring. The term "N.D." indicates that this value was not determined.

Every calcineurin transgenic mouse analyzed showed a dramatic increase in heart size relative to nontransgenic littermates. The heart-to-body weight ratio averaged 2- to 3-fold greater in the calcineurin transgenics compared to control littermates, even as early as 18 days postnatally (FIG. 3; Table 1). No difference in the cardiac phenotype in males and females was observed. Histological analysis showed concentric hypertrophy wherein the cross-sectional areas of the ventricular walls and interventricular septum were dramatically increased (FIG. 3C). The left ventricle was most affected, but the right ventricle and the atrial chambers were also enlarged. In contrast to the well-organized, striated musculature of the normal ventricular wall, cardiomyocytes from the calcineurin transgenic hearts were disorganized and obviously hypertrophic (FIGS. 3D and 3E). The hypertrophic cardiomyocytes often had dramatic karyomegaly. Measurement of cross-sectional areas of myocytes within the left ventricular wall showed a greater than 2-fold increase in calcineurin transgenics compared to controls.

In humans, cardiac hypertrophy frequently progresses to ventricular dilatation, heart failure and sudden death. Similarly, in calcineurin transgenic mice, dilatation of the ventricular chambers with increasing age was observed (FIGS. 3F and 3G). Calcineurin transgenic mice were also highly susceptible to sudden death. This occurred spontaneously, as well as during handling or anesthesia. The mice that died from sudden death showed right and left ventricular dilatation indicative of heart failure. Histology of the lungs also revealed extensive perivascular edema and intra-alveolar macrophages containing red blood cells, findings consistent with heart failure. One of the hallmarks of heart failure is fibrosis of the ventricular wall. The hearts of calcineurin transgenics contained extensive, primarily interstitial, deposits of collagen, as revealed by trichrome staining (FIG. 3H). In foci with marked fibrosis, myofiber degeneration was evident.

Figure 5:
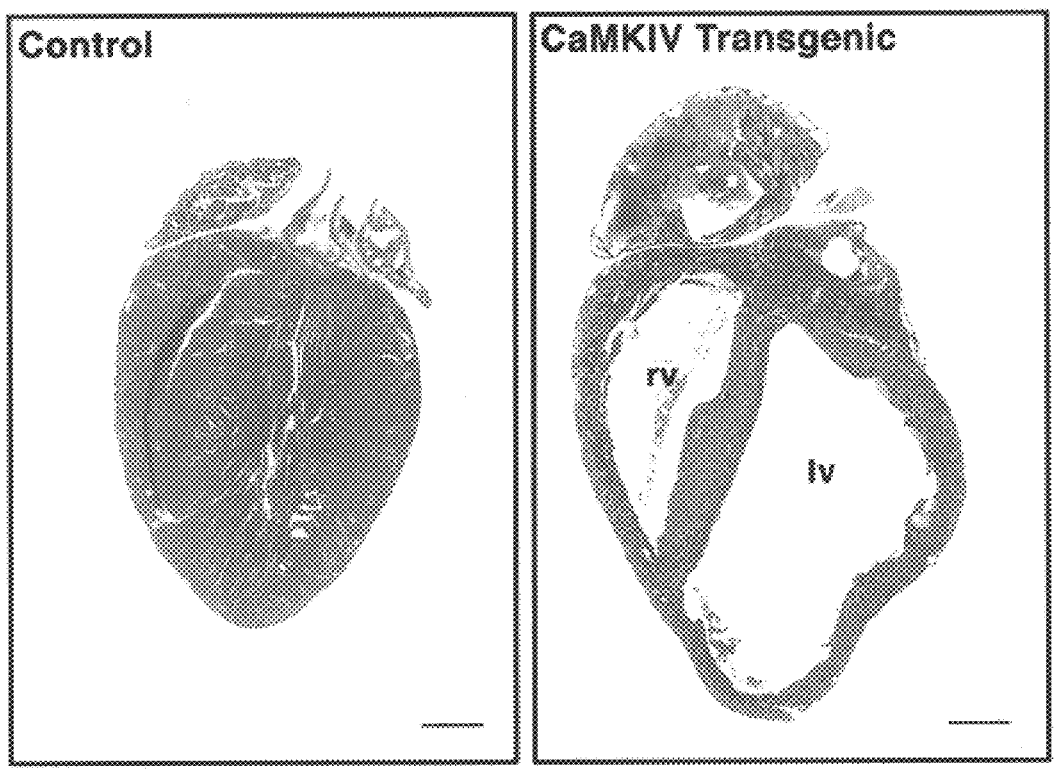
FIG. 5 shows photographs of hearts of α-MHC CaMKIV transgenic mice. Control and α-MHC-CaMKIV transgenic littermates were sacrificed at 3 weeks of age and the hearts were removed and sectioned longitudinally and stained with hematoxylin and eosin. la, left atrium; lv, left ventricle; re, right atrium; rv, right ventricle.

Similarly, transgenic mice expressing a constitutively active form of CaMKIV under control of an α-MHC promoter, showed dramatic increases in heart size relative to nontransgenic littermates, as shown in FIG. 5.

Activation of the molecular response to hypertrophy in vivo by calcineurin. To determine whether activated calcineurin induced changes in cardiac gene expression characteristic of hypertrophy and heart failure, a quantitative dot blot assay was used to examine RNA from hearts of calcineurin transgenics and nontransgenic littermates. Consistent with the reactivation of the fetal program of gene expression, MHC, α-skeletal actin, and BNP transcripts were dramatically upregulated in transgenic hearts, whereas α-MHC was downregulated. Transcripts for sarcoplasmic reticulum $Ca^{++}$-ATPase (SERCA) and phospholamban (PLB) have been shown previously to be downregulated during heart failure, as the failing myocardium exhibits defective $Ca^{++}$-handling (Mercadier et al. (1990) *J. Clin. Invest.* 85:305–309; Schwinger et al. (1995) *Circulation* 92:3220–3228); both transcripts were decreased in calcineurin trangenics. There was no significant change in glyceraldehyde-3-phosphate dehydrogenase (GAPDH) expression.

Prevention of cardiac hypertrophy with CsA. To determine whether inhibition of calcineurin activity in vivo might be an effective means of preventing cardiac hypertrophy, we tested whether subcutaneous injection of CsA could prevent cardiac dysfunction in calcineurin transgenic mice. For these experiments, 8 transgenic littermates from a litter of transgenic mouse #37 (Table 1) were used.

Figure 4A:
FIGS. 4A–C depict the results of treatment of α-MHC-calcineurin mice with CsA. A) The regimen for CsA treatment is shown. B) α-MHC-calcineurin transgenic and nontransgenic mice, were treated with or without CsA (25 mg/kg), as indicated. Heart-to-body weight ratios are expressed±standard deviations. Transgenic littermates obtained from male calcineurin transgenic #37 (see Table 1) were treated with CsA or vehicle alone beginning at 9 days of age, as described in Example 2. At 25 days of age, animals were sacrificed and hearts were removed and sectioned longitudinally. C) Hematoxylin and eosin-stined sections of hearts from nontransgenic (control) and transgenic mice treated with vehicle (center panel) or CsA (right panel). la, left atrium; lv, left ventricle; ra, right atrium; rv, right ventricle. The right atrium was removed from the control and both atria were removed from the transgenic treated with CsA. Bar=2 mm.
Figure 4B:
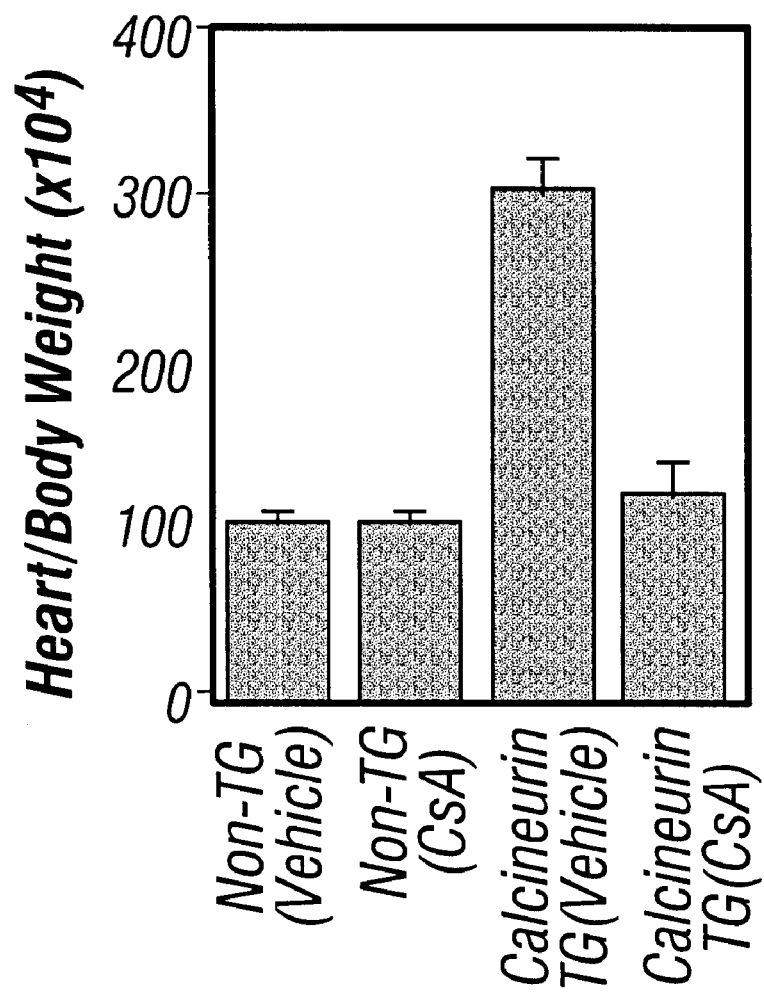
Figure 4C:
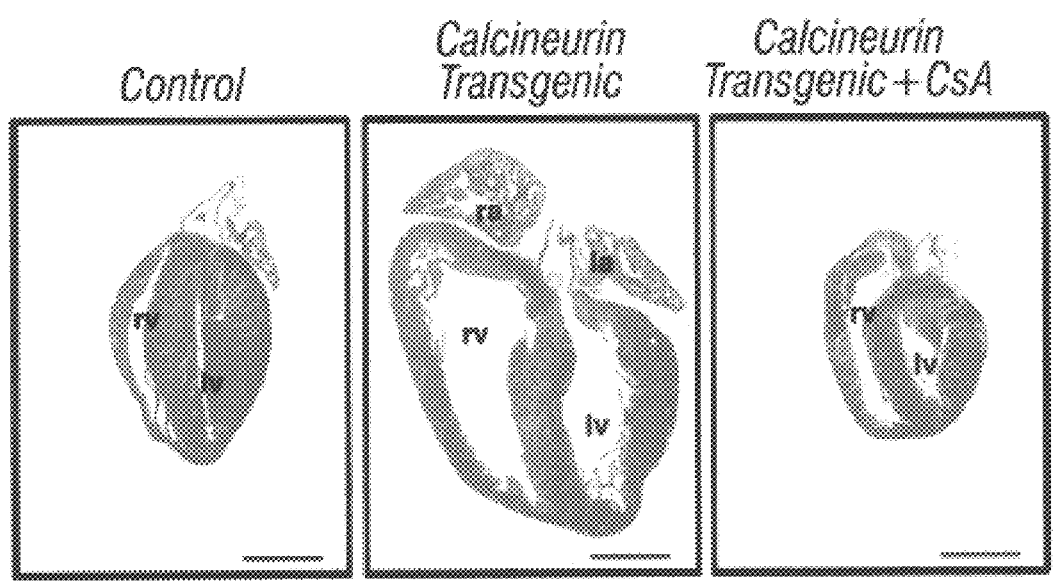

Four transgene-positive offspring were injected twice daily with 25 mg/ml CsA and four were injected with vehicle alone. Four nontransgenic littermates were also treated with CsA to control for potential toxic effects or any cardiac abnormalities induced by CsA. CsA treatment was initiated at 9 days of age and animals were sacrificed 16 days later. As shown in FIG. 4C, the hearts of vehicle-treated animals were highly hypertrophic and dilated by day 25, whereas those from CsA-treated littermates were not significantly different in size from nontransgenic controls. The mean heart-to-body weight ratios for calcineurin transgenics were nearly 3-fold larger than those of CsA-treated transgenics and nontransgenics, as shown in FIG. 4B. CsA treatment also prevented fibrosis of the hearts of calcineurin transgenics.

At a cellular level, the hypertrophic response of cardiomyocytes in the calcineurin transgenics was largely inhibited by CsA, although there were isolated areas of myofiber disarray and scattered cells with prominent hyperchromatic nuclei. CsA treatment prevented gross cardiac hypertrophy and associated pathology in response to activated calcineurin in vivo.

EXAMPLE 3

Characterization of Effects of CaMKII and CaN on Expression of Hypertrophy-sensitive Genes in a Cultured Cardiomyocyte Cell Model Protocols Primary myocardial cell cultures. Primary cultures of neonatal rat cardiac myocytes were prepared using 1–4 days old Sprague-Dawley rats. Rat pups (an average of 15 pups per preparation) were decapitated and hearts were removed sterilely from thoracic cavity and washed with Medium 199 (Life Technologies, Gaithersburg, Md.) to remove residual blood. The atria were removed and ventricles were finely minced and subjected to three sequential Viokase (A. H. Robbins Company, Richmond, Va.) digestion of 18 minutes each. Viokase containing lipase, protease and amylase as well as other pancreatic enzymes was made at 1 mg/ml in PBS buffer and used at a rate of 120 ml per 15 hearts. Supernatants pooled from the three digestions were put on ice bath in order to quench the digestion reaction. The supernatants were then centrifuged at 2000 rpm for 8 min at room temperature in a Beckman TJ-6 rotor. Cell pellets were resuspended in Medium 199 supplemented with 10% fetal bovine serum and 50 $\mu$g/ml gentamicin. Cells were then plated in 100-mm tissue culture dishes and incubated in a 37° C. cell culture incubator. This process, called "pre-plating", selectively removes rapidly attaching, non-cardiac myocyte cells such as fibroblasts from the cell population therefore enriching the cell population for cardiomyocytes. Forty-five to fifty minutes later, the non-attached cells were transferred to fresh 60-mm dishes at a density of about 150 cells/mm$^2$ for the initiation of long-term culture. After 20–24 hours, myocardial cell cultures were washed and maintained in fresh medium supplemented with 10% fetal bovine serum as described above in 60-mm dishes. The cultures of cardiomyocyte could be maintained for up to 7 days.

Transient transfection. It was necessary to culture the isolated cardiomyocytes in serum-free medium to eliminate effects on gene expression mediated through serum response elements. Primary myocardial cultures were first washed with serum-free growth medium and then maintained in serum-free Medium 199 supplemented with Nutridoma HU (Boehringer Mannheim Corporation, Indianapolis, Ind.) which contained human serum albumin, bovine insulin and human transferrin. Transfection were carried out by using a liposome-based transfecting agent, Lipofectamine (Life Technologies, Grand Island, N.Y.). The procedures used for transient transfection were followed as the manufacturer's instructions. The optimal values including DNA concentration, lipofectamine concentration, and time length for transfection were determined prior to experiments carried out in this study. Briefly, for each transfection, 2 $\mu$g DNA and 20 $\mu$g lipofectamine were diluted into separate vials containing 300 $\mu$l serum-free nutridoma supplemented medium. The two solutions were then combined and incubated at room temperature for 15–45 minutes to allow DNA-liposome complexes to form. For each transfection, 2.4 ml of serum-free nutridoma supplemented medium were added to the tube containing the DNA-liposome complexes and the diluted mixture was overlaid onto the adherent cardiomyocytes that had been rinsed once with 2 ml of serum-free medium in a 60-mm tissue culture plate. The cell cultures were incubated at 37° C. in a $CO_2$ incubator containing 5% $CO_2$ for 24 hours, at which time various test compounds were added. Promoter activities from cell extracts were assayed within 48 hours following the start oftransfection.

For $\alpha_1$-adrenergic stimulation, 100 $\mu$M PE (Sigma, St. Louis, Mo.) was added to the cells. DOB (Gensia Laboratories, Ltd., Irving, Calif.), a selective $\beta_1$-adrenergic agonist, was added at a concentration of 10 $\mu$M. To correct for variation in transfection efficiencies, p$\beta$Gal-Control was used as an internal control. Chemiluminescent $\beta$-galactosidase activity was assayed by using an aliquot of the same cell lysates collected for the luciferase assay and measured in the same luminometer as described below.

Firefly luciferase assay. The firefly luciferase assay is based upon a commercial (Promega, Madison, Wis.) long term "glow" type of bioluminescence assay. Briefly, activation of luciferin results in the formation of an enzyme-bound luciferyl adenylate (luciferyl-AMP). The enzyme intermediate, luciferyl-AMP is oxidated in the presence of coenzyme A (CoA) and leads to the formation of an enzyme-bound excited product which subsequently decomposes to emit light and a tightly enzyme-bound product. In the presence of CoA, oxidation occurs instead from luciferyl-CoA with more favorable total kinetics. Cells to be assayed for luciferase activity were rinsed twice with PBS buffer and lysed in Reporter Lysis 1×Buffer (Promega) and then harvested by scraping. Large debris were pelleted by brief centrifugation and supernatant was transferred to fresh tubes. For luciferase assay, 20 $\mu$l of cell extract was mixed with 100 $\mu$l Luciferase Assay Reagent (Promega) which contained 20 mM Tricine, 1.07 mM $(MgCO_3)_4Mg(OH)_2$ $5H_2O$, 2.67 mM $MgSO_4$, 0.1 mM EDTA, 33.3 mM DTT, 270 $\mu$M coenzyme A, 470 $\mu$M luciferin, and 530 $\mu$M ATP. Integrated light emission over 10 seconds to 5 minutes was determined in a Turner Designs Luminometer Model 20 (Promega). All assays were performed at room temperature within 1 hour of cell lysis.

Northern Analysis. For ANF message analysis, total RNA were extracted from 1–3-day-old neonate rat cardiomyocyte cell cultures according to the method of Chomczynski and Sacchi using the commercially available TRIzol Reagent (Life Technologies, Grand Island, N.Y.). Rat primary cell cultures were homogenized in TRIzol, and the RNA was extracted by the addition of chloroform and precipitated in the presence of isopropanol. The isolated total RNA were fractionated on a 1% agarose/formaldehyde gel, and transferred to a nylon membrane by capillary blotting. Blots were prehybridized in a 50% formamide solution (Life Technologies, Grand Island, N.Y.) for 3–4 hours at 42° C. and then hybridized overnight with a random primer, biotin-labeled ANF cDNA probe. After washing at high stringency (0.1×SSPE, 0.1% SDS, 65° C.), hybridized biotinylated cDNA were detected by using Chemiluminescent Detection System (TROPIX, Inc., Bedford, Mass.) and then exposed to X-ray film. The ANF bands were quantitated with a Howteck gel scanner (PDI, Huntington station, N.Y.) and normalized to the 28 S rRNA signal to correct for loading and/or transfer efficiencies.

Determination of autonomous CaM kinase II activity. CaM kinase II autonomous activity was determined in rat heart tissue homogenates using the synthetic peptide substrate, autocamtide-2 (KKALRRQETVDAL) (Mar et al. (1990) *Mol. Cell. Biol.* 10:4271–4283; and Farrance et al. (1992) *J. Biol. Chem.* 267:17234–17240) as exogenous substrate. This peptide was modeled after the core autophosphorylation sequence of the rat brain α-CaM kinase II and is highly selective for CaM kinase II. Autonomous CaM kinase II activity was assayed by the phosphorylation of autocamtide-2 in the absence of $Ca^{2+}$/calmodulin and expressed as a proportion of activity obtained in the presence of these cofactors. Tissue slices were incubated in the presence or absence of various drug compounds for required time. At termination of the incubation the tissue slices were homogenized in ice-cold buffer (20 mM Tris-HCl, pH 7.5, 0.5 mM EGTA, 1.0 mM EDTA, 2.0 mM dithiothreitol, 10 mM sodium pyrophosphate, 0.4 mM ammonium molybdate, 100 mg/ml leupeptin) by sonication. Supernatant were cleared by centrifugation (12,000×g, 2 minutes) and then assayed in a reaction mixture containing 50 mM PIPES (pH 7.0), 10 mM $MgCl_2$ 0.1 mg/ml bovine serum albumin, 10 mM autocamtide-2, 20 mM [$\gamma$-$^{32}$P] ATP and either 0.5 mM $CaCl_2$, 5 mg/ml calmodulin for $Ca^{2+}$-stimulated activity or 1 mM EGTA for autonomous activity. The assay was conducted at 30° C. for 30 seconds and terminated by the addition of trichloroacetic acid to a final concentration of 5%. Endogenous protein was sedimented by centrifugation and supernatants containing autocamtide-2 were spotted onto p81 phosphocellulose strips, washed 5 times, dried and $^{32}$P-$PO_4$ content was quantitated by Cerenkov radiation.

Figure 8A:
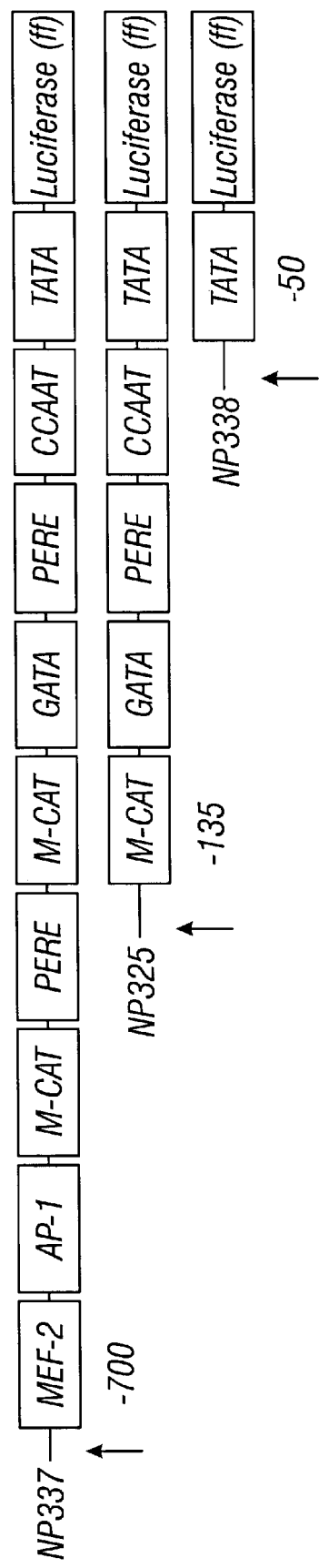
FIGS. 8A–C are bar graphs depicting effects of PE, exogenous CaMKII or CaN on ANF nested deletion promoter-reporter constructs. Values are corrected for transfection efficiency and reported as the mean±SD from at least three experiments.

Plasmid constructs. A series of nested deletion mutants containing various rat cardiac ANF promoter fragments and the rat ANF cDNA were used. This series of promoter-reporter constructs were subcloned into luciferase-based pxp2 vectors. The 5' deletions were generated using appropriate restriction enzyme sites or by PCR amplification. A diagram of key enhancer elements thought to regulate ANF transcription is shown in FIG. 8A. The skeletal α-actin reporter, harboring approximately 400 bp of proximal upstream promoter domain (−394 bp to +24 bp relative to the transcription start site) of the avian cardiac skeletal α-actin gene (containing the majority of the enhancer domains responsive to growth signaling linked to the structural portion of the firefly luciferase gene) was used. Another luciferase-based promoter-reporter construct harboring 400 bp of proximal upstream promoter domain of the avian cardiac α-actin gene was also used. Two isoforms of δ-CaM kinase ($\delta_A$ & $\delta_B$) harbored in pSRα expression vector were used. Expression plasmids for CaM kinase IV including both a full-length form (CaMKIVwt) and a mutated form (CaMKIV313) were used. The constitutively-active form of calcineurin, from neuronal origin, was generated by polymerase chain reaction mutagenesis technique which resulted in the deletion of the auto-inhibitory domain of calcineurin. The mutated fragment was then subcloned into pSRα expression vector. The expression plasmid for mutant brain α-CaM kinase II was constructed by subcloning a cDNA encoding a truncated version (amino acids 1–290) of the wild-type CaM kinase II enzyme which is constitutively active into the EcoRI site of pCMV5, a mammalian expression plasmid containing a multiple cloning sequence immediately down stream from the strong viral promoter of cytomegalovirus. This construct, when transfected into the cardiomyocyte cultures, constitutively produces CaM kinase II enzyme which does not bind $Ca^{2+}$ or calmodulin.

Results

Figure 6C:
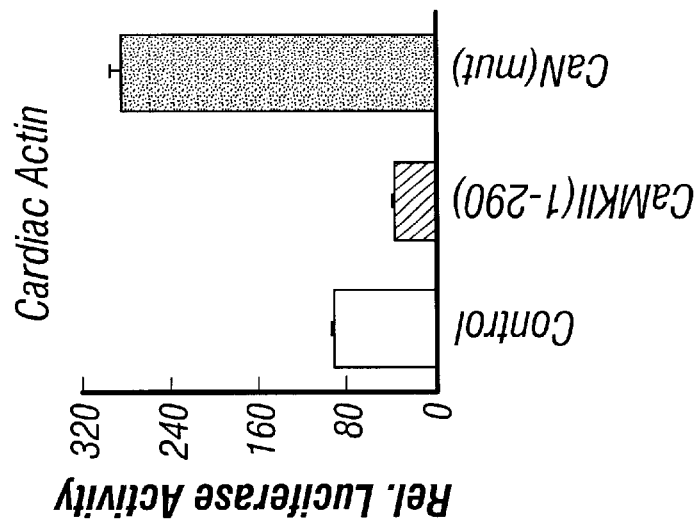
FIGS. 6A–C are bar graphs showing effects of mutated CaMKII and CaN on promoter-reporter constructs comprising ANF, skeletal a-actin, and cardiac a-actin promoters driving luciferase expression. Duplicate dishes of ventricular myocardial cells were co-transfected with reporter plasmids and CaMKII(1-290) or $CaN_{mut}$, constitutively active forms of CaMKII and CaN, respectively. "Control" represents cells co-transfected with expression vectors without cDNA inserts and promoter-reporter plasmids. Values are corrected for transfection efficiency and reported as the mean±standard deviation (SD) from at least three experiments.
Figure 6B:
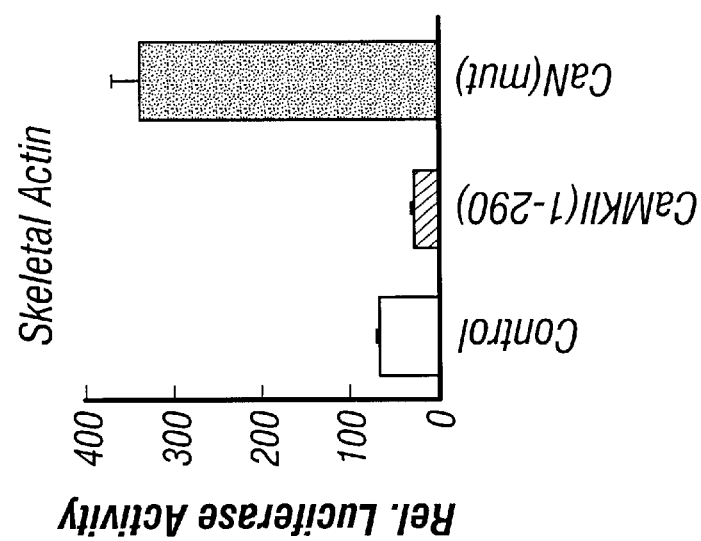
Figure 6A:
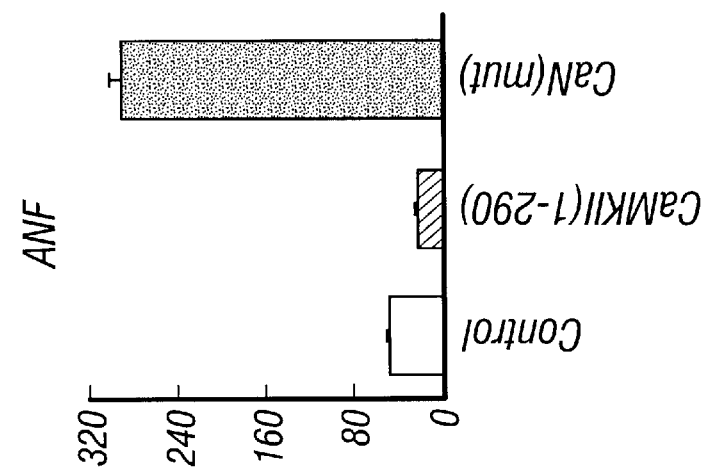

Effects of exogenous CaM kinase II and calcineurin on promoter-reporter activities for ANF, skeletal α-actin and cardiac α-actin genes In this study, we explored a potential functional role for a calcium-dependent protein kinase, CaM kinase II (CaMKII), and a calcium-sensitive phosphatase, calcineurin (CaN), in regulating ANF, skeletal α-actin and cardiac α-actin gene expression. Three luciferase-based promoter-reporter constructs containing nearly full length ANF, skeletal α-actin or cardiac α-actin promoter regions as described above were employed in this study. A co-transfection protocol using vector constructs harboring a mutant, constitutively-active CaMKII α-isoform or a constitutively active mutant form of CaN with the ANF/luciferase, skeletal α-actin/luciferase or cardiac α-actin/luciferase fusion genes was carried out on neonate cardiomyocyte cultures prepared from 1–4-day-old rat pups. Luciferase reporter activities were evaluated As shown in FIG. 6, over-expression of the exogenous CaMKII α-isoform silenced promoter-reporter activities for ANF, skeletal α-actin and cardiac α-actin by 50% compared to control cultures (co-transfected with empty vector). In contrast, over-expression of the exogenous constitutively-active CaN increased ANF, skeletal α-actin and cardiac α-actin promoter activities by 300%–600% over control cells. Results in this experiment suggested that overexpression of a heterologous CaMKII α-isoform leads to silencing of promoter activities for both the cardiac embryonic genes, ANF & skeletal α-actin, and constitutive contractile protein gene, cardiac α-actin. In contrast, activation of a exogenous CaN results in superinduction of the promoter activities for these three genes.

Effects of CaM kinase isoenzymes on ANF promoter-reporter activity

Figure 7B:
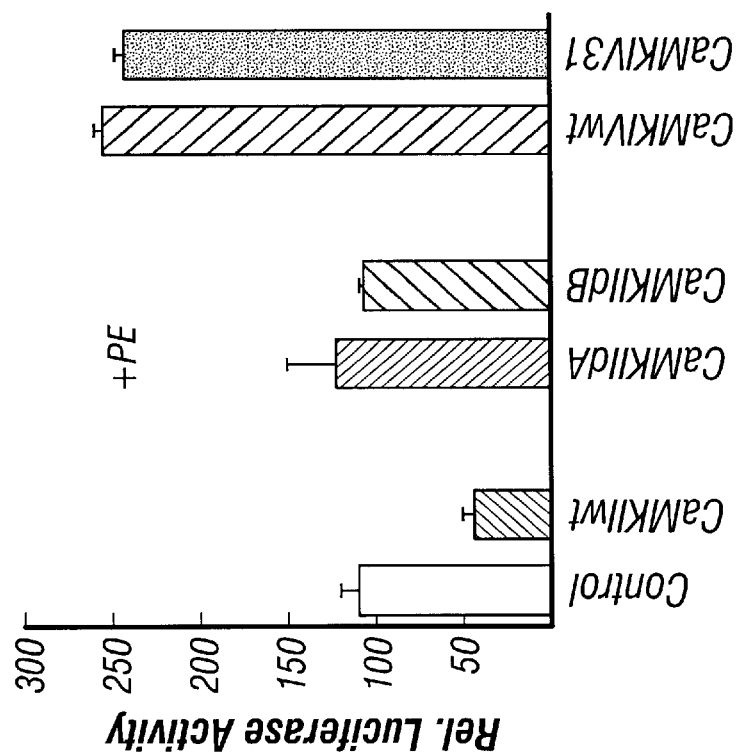
FIGS. 7A and 7B are bar graphs depicting effects of exogenous CaM kinase isoenzymes on ANF promoter-reporter activity. Duplicate dishes of ventricular cardiomyocytes were co-transfected with ANF promoter-reporter construct and expression constructs encoding various CaMK isoforms. "Control" represents cells co-transfected with expression vector without a cDNA insert and promoter-reporter plasmid. Values are corrected for transfection efficiency and reported as the mean±SD from at least three experiments.
Figure 7A:
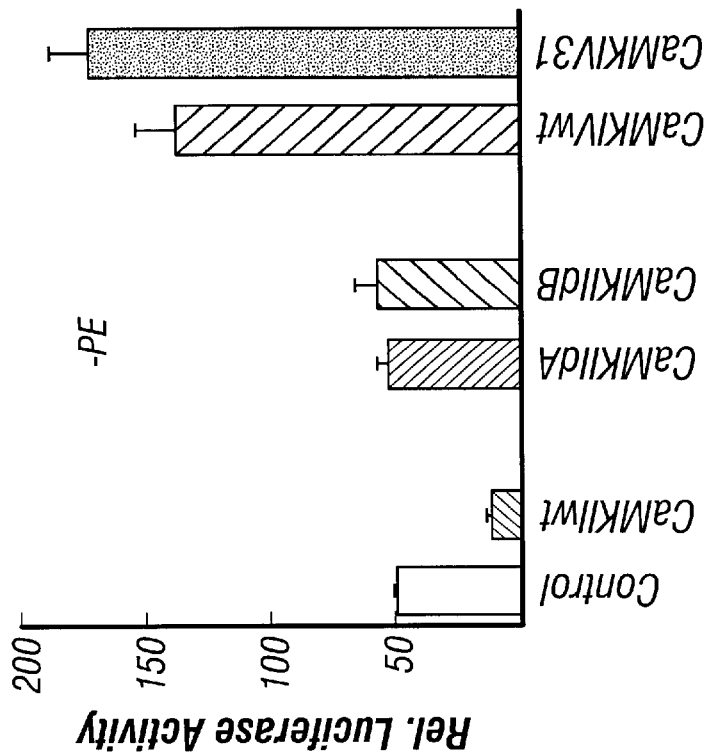

The CaM kinase family has at least ten members, which differ in structure, distribution, regulation and enzymatic activity. The results, presented in FIG. 6, suggest that mutated α-CaMKII induced down-regulation of hypertrophy-sensitive genes. It was of interest to determine what effects of other CaM kinase family members play on the prototypical hypertrophy-sensitive gene, ANF. Select members of CaM kinase family, including wild type CaMKII (CaMKII$_{wt}$), δ-CaMKII ($\delta_A$ & $\delta_B$), and CaMKIV (wild-type & mutated form), were used for co-transfection with the ANF promoter-reporter construct described above. PE induction of ANF was also evaluated in the presence of each of the exogenous CaM kinase members. As shown in FIG. 7, CaMKII$_{wt}$ reduced ANF promoter activity by ~400%. In contrast, CaMKIV$_{wt}$ increased ANF promoter activity by 270%, while CaMKIV$_{mut}$, increased ANF promoter activity by ~400%. CaMKII δ isoforms including both $\delta_A$ and $\delta_B$ virtually did not alter the promoter activities of ANF. Similar results were obtained in the presence of PE stimulation in transfected cardiomyocytes, as shown in FIG.

7B. Taken together, these data indicate that different CaM kinase family members show differential effects on the expression of ANF.

Figure 8C:
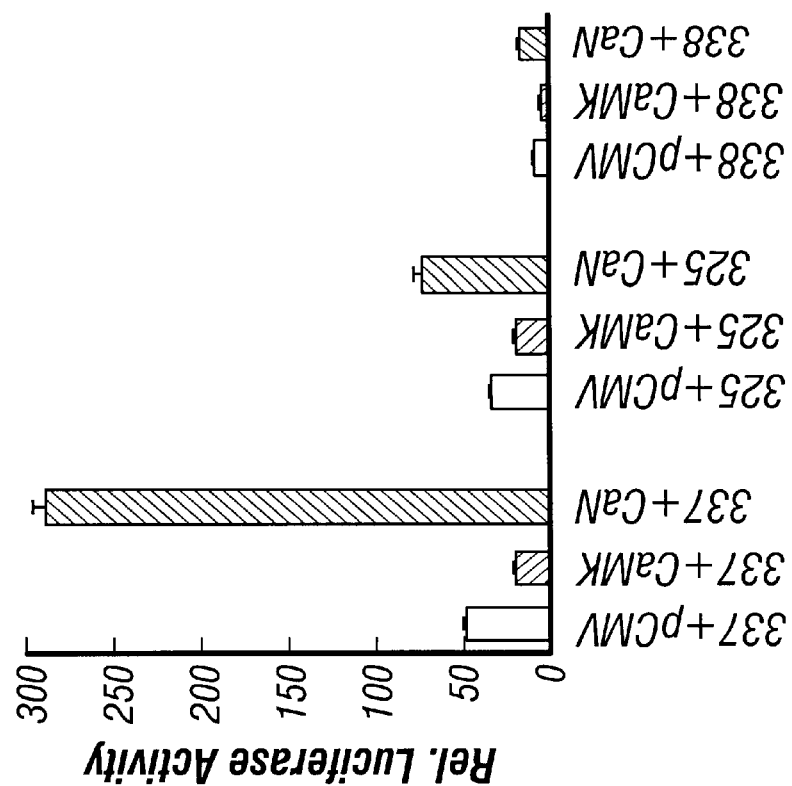
Figure 8B:
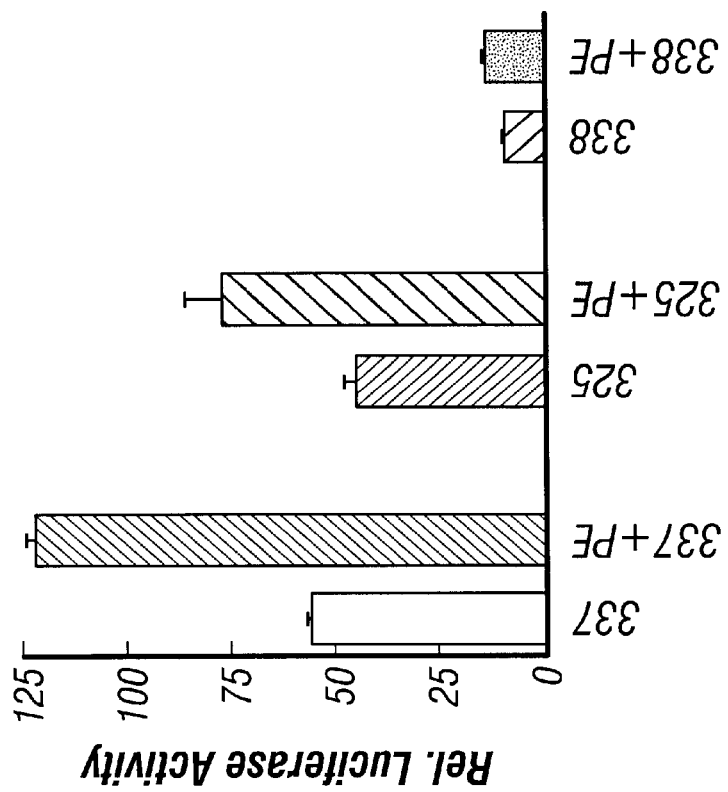

Effect of exogenous CaMKII or CaN on ANF promoter-reporter nested deletion constructs In these studies, a series of nested deletion constructs generated from the 5' promoter/enhancer domain of the rat cardiac ANF gene was used. Three different lengths of the native ANF promoter fragments were ligated to the structural portion of the firefly luciferase gene as described above. A diagram of all of the identified functional enhancer elements for ANF gene is shown in FIG. 8A. Reporter activity for each of the nested deletion constructs in cardiomyocyte cultures exposed to PE is shown in FIG. 8B. Promoter-reporter constructs containing sufficient upstream sequence to include the PERE (PE Response Element) motif, ANF700 (NP337) and ANF135 (NP325), but not promoter sequences which have lost this motif, ANF50 (NP338), were activated by PE exposure. It was assessed whether silencing/induction of the ANF promoter-reporter activity by expression of exogenous CaMKII/CaN could be localized to a region of the ANF promoter domain. The ANF promoter-reporter nested deletion constructs described above were co-transfected respectively with constitutively-active CaMKII or CaN. As shown in FIG. 8C, over-expression of exogenous CaMKII resulted in silencing of all three ANF 5'-deletion promoter constructs by 50% compared to control cultures, whereas over-expression of exogenous CaN increased each of the three ANF promoter construct by a range from 200–600% over control cultures. These data indicate that inhibition/induction of the ANF promoter-reporter activity by CaMKII/CaN could not be restricted to a defined region or domain for the ANF promoter.

Beta-adrenergic receptor signaling and cardiac CaM kinase II activation

Figure 9:
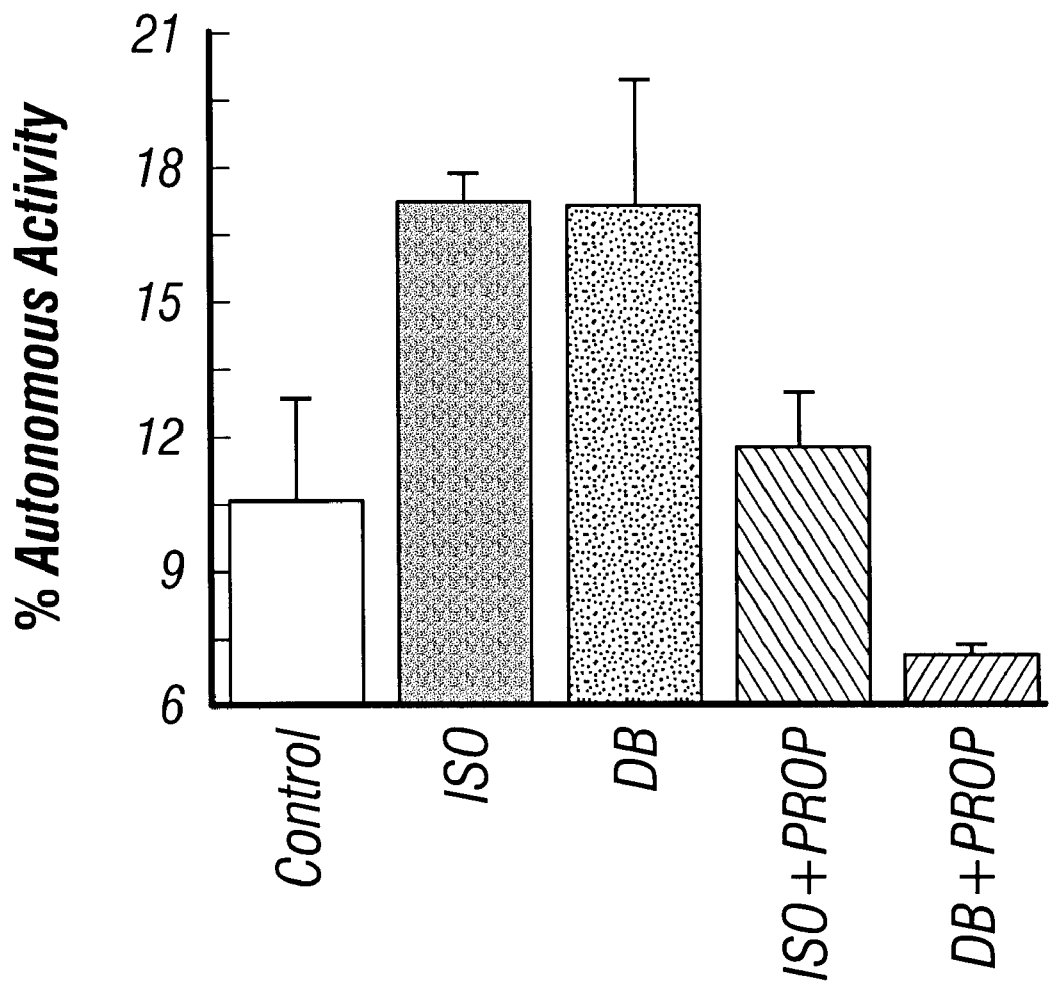
FIG. 9 is a bar graph depicting stimulation of CAMKII activity by b1-adrenergic receptor in neonate rat heart tissue. Neonatal (1–4 day old) heart tissue slices were isolated and treated with isoproterenol (ISO, 100 μM), dolbutamine (DOB, 10 μM, or vehicle alone (control). Propanolol (PROP, 20 μM) was added 2 minutes before agonists were added. After 30 seconds of treatment, autonomous CaMKII activity was assayed. Data are shown as percentage of the ratio of calcium independent activity divided by total activity and represented as the mean±SD from at least three experiments.

These experiments determined whether signaling through $\beta_1$-adrenergic receptor subtype could activate cardiac CaMKII. Heart tissue slices from 1–4-day-old neonatal rats were freshly isolated and treated with either the β1 selective agonist, dolbutamine (DOB), or the mixed β1 (β1 & β2) agonist, isoproterenol (ISO). In parallel studies, β1 antagonist, propanolol (PROP) was added 15 sec before agonists were added. Later, autonomous activity (% of calcium independent activity) of CaMKII was assayed. The results of such an experiment are shown in FIG. 9. CaMKII autonomous activation was increased ~170% over the activity observed in unstimulated heart tissues 30 seconds following treatment by DOB or ISO. In addition, the β1 antagonist, PROP, when added prior to either DOB or ISO addition, blocked activation of CaMKII autonomous activity. These results demonstrate that exposure to $\beta_1$-adrenergic agonist leads to cardiac endogenous CaMKII activation. This activation of CaMKII activity is a $\beta_1$-receptor-mediated response.

Effect of adrenoceptor agonists on promoter-reporter activities for ANF, skeletal α-actin and cardiac α-actin genes Results of experiments shown above suggested that CaN leads to induction of these three genes in neonate rat cardiomyocytes. It was of interest to determine the effect of α- and β-adrenergic stimuli on the expression of ANF, skeletal α-actin and cardiac α-actin. Luciferase-based promoter-reporter constructs harboring ANF, skeletal α-actin and cardiac α-actin promoter domains as described above were transfected into primary neonatal rat cardiomyocyte cultures. The transfected cardiomyocytes were then exposed to the $\alpha_1$-adrenergic agonist, phenylephrine (PE), $\beta_1$-adrenergic agonist, DOB, or type β-transforming growth factor (TGF-β1). As shown in FIG. 10, panels A, B and C, each of these promoter-reporter activities was decreased approximately 50% by treatment with DOB. Reporter activities for ANF and skeletal α-actin were transactivated by 200% over that in control cells when cardiomyocytes were exposed to PE, as shown in FIG. 10, panels A and B. Promoter activity for cardiac α-actin was not significantly stimulated in PE-treated cardiomyocytes, whereas treatment with TGF-β1, in agreement with previous studies, induced cardiac α-actin promoter-reporter activity by 700% over control cells. These data show that both α-adrenergic and β-adrenergic stimulation modulates the expression of cardiac hypertrophy-sensitive genes, such as ANF, skeletal α-actin and cardiac α-actin. $\beta_1$-adrenergic stimulation is able to inhibit the promoter activities for both embryonic genes, like ANF, skeletal α-actin, and constitutive contractile protein gene, like cardiac α-actin. Therefore, it was of interest to assess whether the changing of ANF reporter activity observed in the above experiments was a response to the alteration of ANF message pools.

Figure 10C:
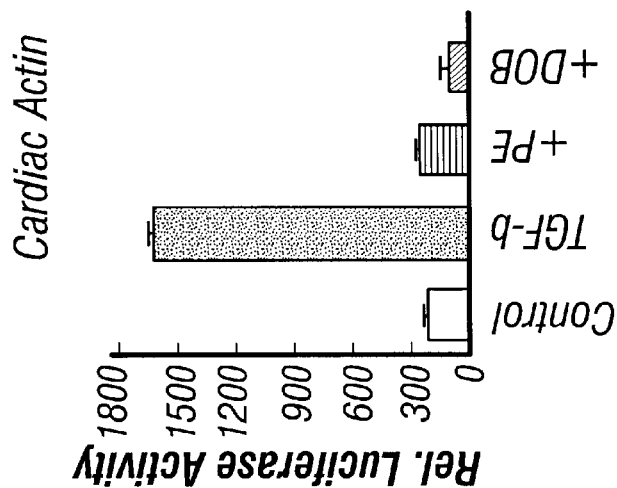
FIGS. 10A–E presents data showing the effects of adrenoceptor agonists on promoter-reporter activities for ANF, skeletal a-actin and cardiac a-actin, and a time course of effects of DOB on ANF message levels.
Figure 10B:
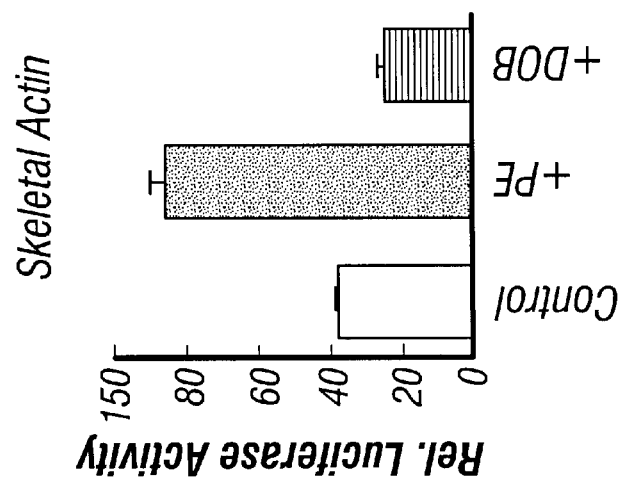
Figure 10A:
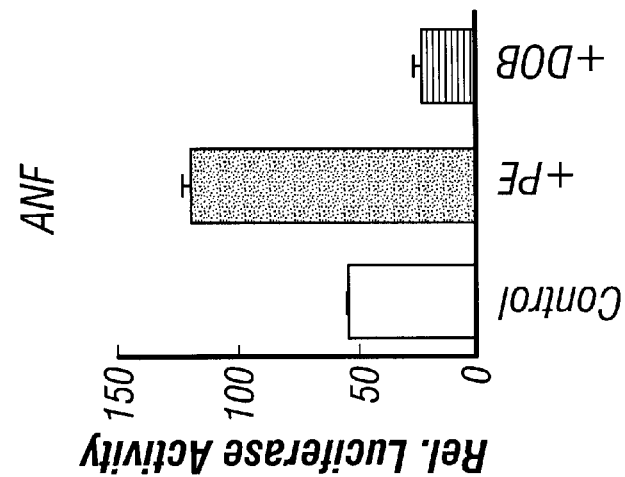
Figure 10D:
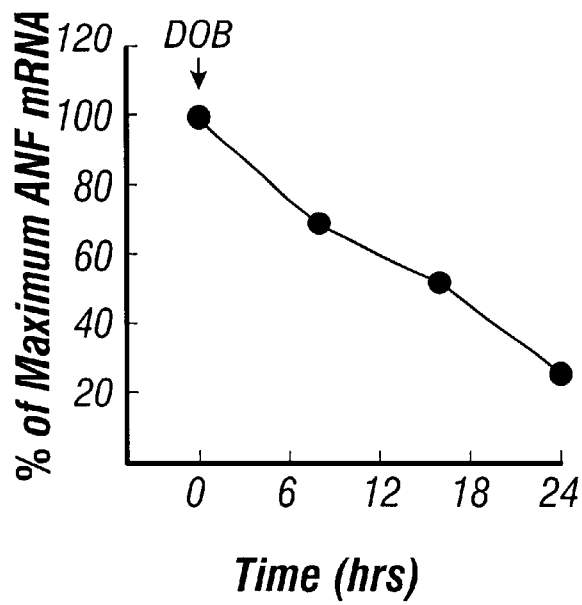
Figure 10E:
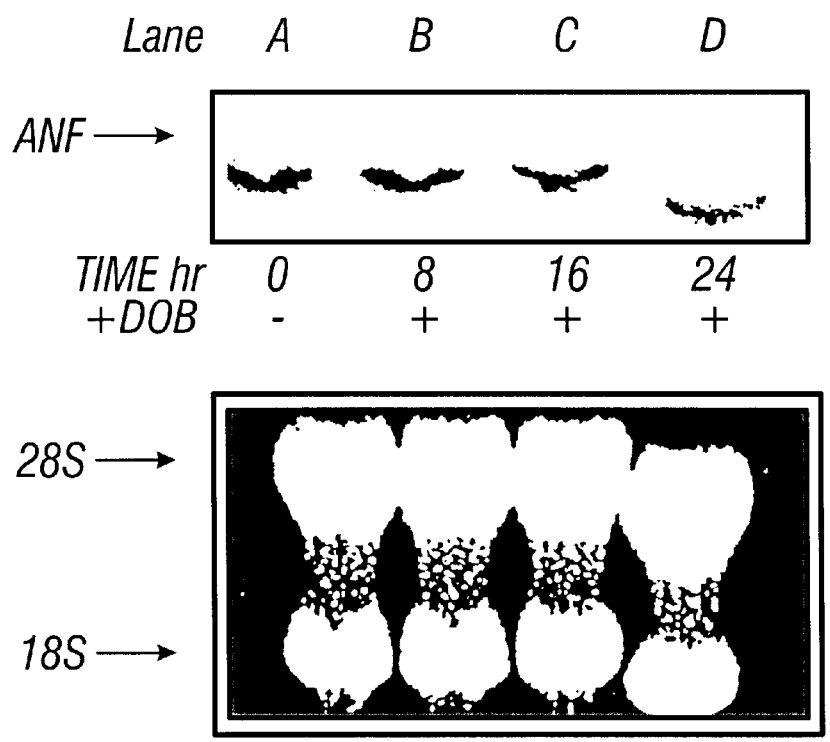

Primary cultures of neonatal cardiocytes were kept in serum-free medium and β1 agonist, DOB, was applied to the cells at various times. ANF message RNA was evaluated in the end by northern analysis protocols as described above. As shown in FIG. 10D, when cell cultures were exposed to DOB, abundance of the ANF message began to drop so that within 16 hours it was only about half that observed in control cultures (no drug addition). This trend continued so that 24 hours after DOB exposure, ANF mRNA had declined by 75% compared to control values. These results suggest that part, if not all, of the changes in reporter activities occurred at the level of gene transcription.

EXAMPLE 4

Transcriptional Regulation of Hypertrophy-sensitive Genes by an Inducible Calcineurin Expression System Plasmids Constructs Tetracycline-controlled transactivator (tTA) expression plasmid pUHD15-1 encodes chimeric protein tTA under the control of the human cytomegalovirus (CMV) promoter and enhancer. tTA consists of amino acid residues 1–207 from the tetR protein and residues 363–490 from VP16 (Gossen and Bujard (1992) *Proc. Natl. Acad. Sci. USA* 89:5547–5551.

Plasmid pUHD10-3 contains a chimeric tet operon/CMV minimal promoter upstream of multiple cloning sites (Bujard, 1996). pUHC13-3 is a firefly luciferase reporter gene expression plasmid driven by the chimeric tet operon/CMV minimal promoter (Gossen and Bujard (1992).

A constitutively active gene form of calcineurin (ΔCaM-AI) was originally recovered from plasmid pCN(α)ΔCaM-AI, which was generated by subcloning the auto-inhibitory domain-deleted calcineurin gene mutant into pSRα expression vector (Parson et al., 1994 *J. Biol. Chem.* 269:19610–19616). To generate tTA inducible calcineurin construct p10-3CaN, a 1.2 Kbp EcoRI fragment of pCN(α)ΔCaM-AI, coding the constitutively active calcineurin, was subcloned into the unique EcoRI cleavage site of the plasmid pUHD10-3, which contains a tTA-dependent cytomegalovirus (CMV) minimal promoter in front of the EcoRI cloning site (Bujard, 1996 http://www.zmbh.uniheidelberg.de/bujard/reporter/pUHD10-3).

ANF-luciferase promoter-reporter construct, NP337 was made by cloning about 700-bp nucleotides of ANF proximal promoter fragment into luciferase-based pXP-2 vector as previously described elsewhere (McBride et al. (1993) *Mol. Cell. Biol.* 13:600–612).

The skeletal α-actin reporter, SkA-Luc, was constructed by subcloning approximately 420 bp proximal upstream promoter (−394 bp to +24 bp) of avian skeletal α-actin gene into the firefly luciferase expression vector pXP1 (MacLellan et al. (1994) *J. Biol. Chem.* 269:16754–16760). Another reporter construct, cardiac α-actin promoter-luciferase (CardA-Luc), was generated by subcloning a 330-bp fragment of chicken cardiac α-actin promoter and immediate upstream region (from −315 to +15, relative to the transcription start site) into the HindIII cloning site of the pGL2-basic luciferase vector (Chen and Schwartz (1996) *Mol. Cell. Biol.* 16:6372–6384).

Cell Cultures

Primary myocardial cell cultures Primary ventricular myocytes were prepared from 1–4 day old Sprague-Dawley rats, as described in Example 3.

Results

Regulation of an exogenous target gene transcription by the tetracycline-dependent transactivator (tTA) expression system in primary neonatal rat cardiomyocytes.

Figure 11A:
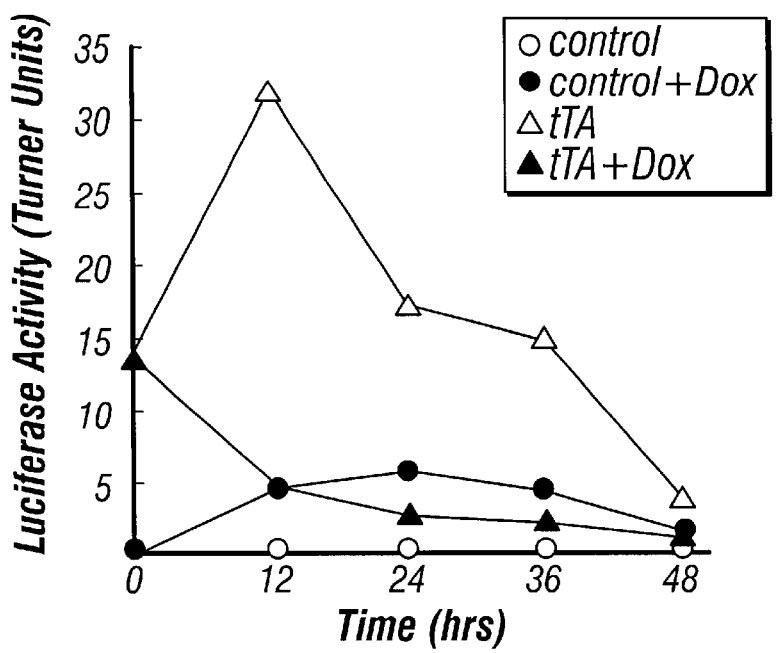
FIGS. 11A and 11B show regulation of tTA-dependent target gene expression in primary rat cardiomyocytes. Cardiomyocytes were co-transfected with tTA expression plasmid pUHD15-1 and either a tTA-dependent luciferase construct pUHC13-3 or empty vector as control. 16 hours after transfection, cells were incubated in either medium without doxcycline (DOX) or medium with doxcycline.
Figure 11B:
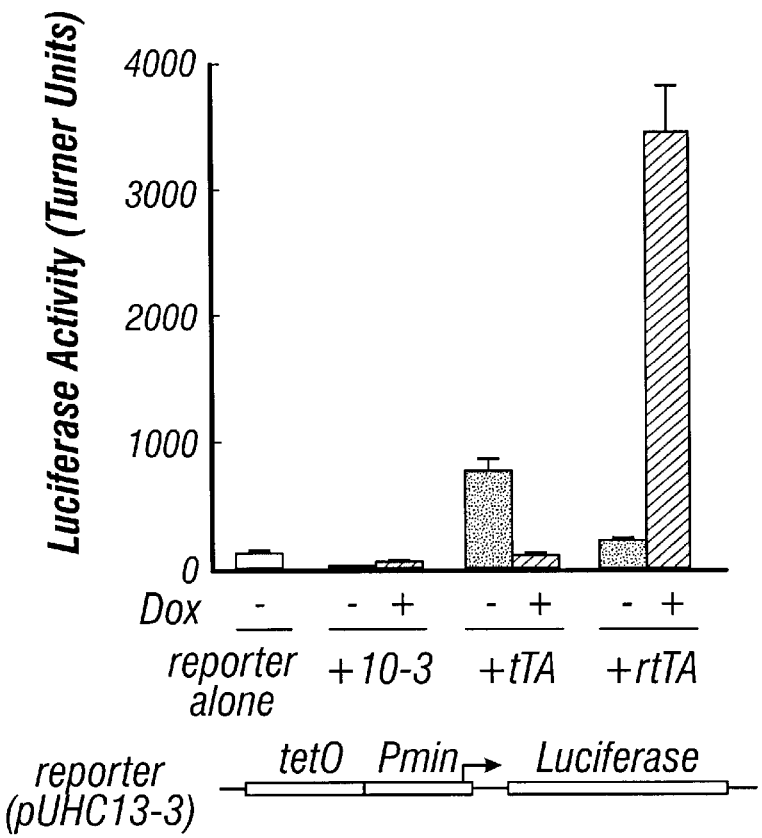

The firefly luciferase gene as a reporter gene was under control of the chimeric tet operon/CMV minimal promoter in pUHC13-3. Transient transfections were carried out as described in Example 3. When this construct and tTA expression plasmid pUHD15-1 were co-transfected into cells, in the absence or presence of the effector substance doxcycline, changes in luciferase activity would indicate the ability of tTA system to regulate the transcription of target gene transcription. To test whether a tetracycline-regulated gene expression system functions in primary rat cardiomyocytes, cell cultures were co-transfected with tTA expression plasmid pUHD15-1 (0.25 μg) and tTA-stimulated luciferase gene expression construct pUHC13-3 (0.25 μg). As a control, the same amounts of reporter plasmid pUHC13-3 plus an empty vector, pUHD10-3, were transfected into cardiomyocytes from same cell preparation. After transfection, luciferase activities in cell extracts were examined at various time points, using the luciferase assay as described in Example 3. In the absence of tTA, only very low levels of reporter gene activity were detected during the 48 hours post-transfection. tTA expression resulted in a dramatic increase in reporter activity during this period, and target gene activities reached a maximum at 12 hours after transfection, as shown in FIG. 11A. At 12 hours post-transfection, the luciferase activities in the tTA-transfected cells were over 30-fold higher than those in the cell without tTA transfection (FIGS. 11A and 11B). When the cells were treated with 1 μg/ml doxcycline (Fluka Chemical Corp.) after transfection, transactivation of the target gene was markedly repressed. However, the doxcycline treatment itself caused a transiently low level expression of the target gene (about a 4-fold increase at 12 hour post-transfection) (FIGS. 11A and 11B), suggesting that doxcycline repression to the target gene in primary cardiomyocytes is not complete. It is possible that exogenous gene expression in transient transfection is not under tight control of native gene regulation machinery in these cells. Doxcycline treatment might cause a weak signal to stimulate the low level expression of this target gene. Therefore, doxcycline does not appear to be the best effector to regulate cardiac gene transcription in this system.

Figure 12:
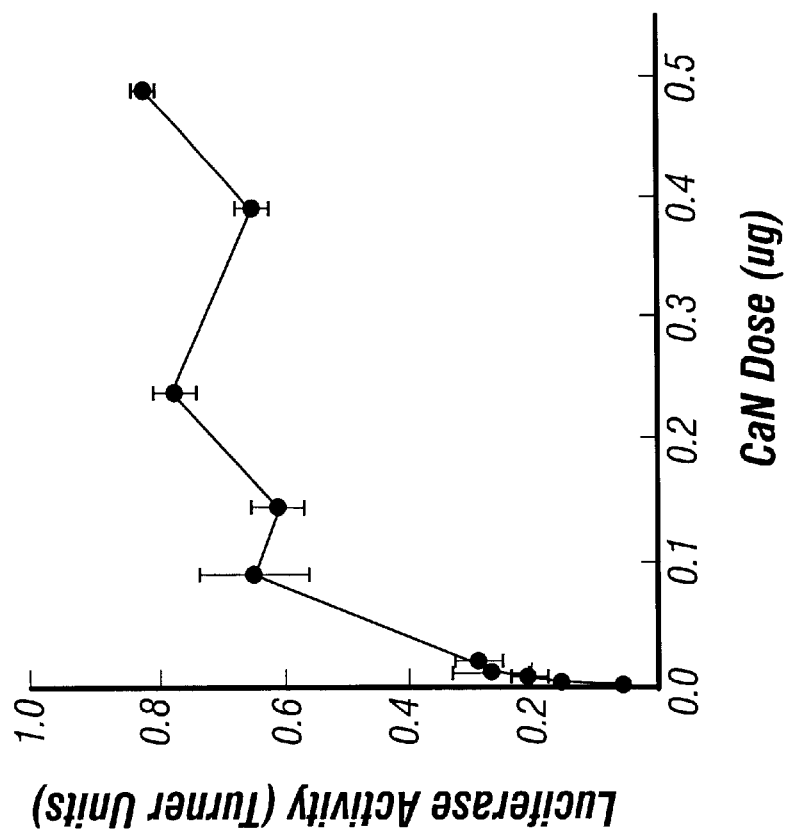
FIG. 12 is a graph showing dose dependency of the transcription of cardiac hypertrophy-sensitive genes in myocardial cells. 0.25 µg tTA expression construct pUHD15-1, 0.25 µg cardiac a-actin promoter-reporter plasmid CardA-Luc, and various amounts of tTA-dependent CaN expression construct p10-3CaN were cotransfected into cells. Data are representative of six independent experiments. Values are reported as mean±SE; n=3 cultures.

Transcription of the Hypertrophy-sensitive Genes Induced by tTA-regulated Calcineurin Expression System depends on Calcineurin Gene Dose Constitutively expressed active calcineurin activates the transcription of ANF reporter gene in primary rat cardiomyocytes. Furthermore, the transcription of cardiac α-actin reporter gene is induced by tTA-stimulated active calcineurin expression in Pac-1 smooth muscle cells. To detect the effects of active calcineurin on the cardiac gene transcription in primary cardiomyocytes and determine the optimal concentration of calcineurin construct in transfection to induce cardiac gene expression, various amounts of tTA-dependent activated calcineurin expression construct p10-3CaN, 0.25 μg tTA expression plasmid pUHD1 5-1 and 0.25 μg cardiac α-actin promoter-reporter plasmid CardA-Luc were transfected into primary rat cardiomyocytes. The results are shown in FIG. 12. The empty vector, pUHD 10-3, was used as a control to substitute for p10-3CaN or to complement total DNA to 0.75 μg/per well. At 24 hours after transfection, the expression levels of cardiac α-actin reporter gene were analyzed by the luciferase assay, as described in Example 3. As shown in FIG. 12, in the absence of exogenous active calcineurin, the level of reporter gene expression was quite low, whereas the transcription of cardiac α-actin reporter gene was gradually enhanced by increasing doses of transfected p10-3CaN. When the amount of calcineurin DNA was up to 0.25 μg, the expression of reporter gene was increased to nearly maximum levels. Clearly, the expression of cardiac α-actin gene is active calcineurin gene dose-dependent. 0.25 μg p10-3CaN was used as the optimal dose in subsequent experiments.

Figure 13A:
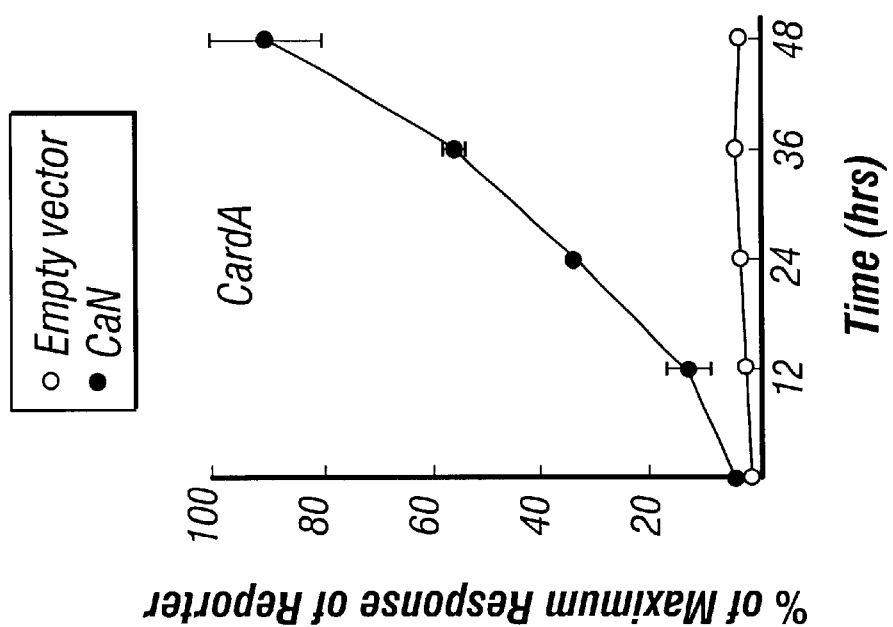
FIG. 13 presents graphs showing a time course of transcription of cardiac hypertrophy-response genes induced by exogenous active CaN in myocardial cells. Data are normalized, and are expressed as a percentage of the maximum response. Data are representative of three independent experiments. Values are reported as mean±SE; n=3 cultures.
Figure 13C:
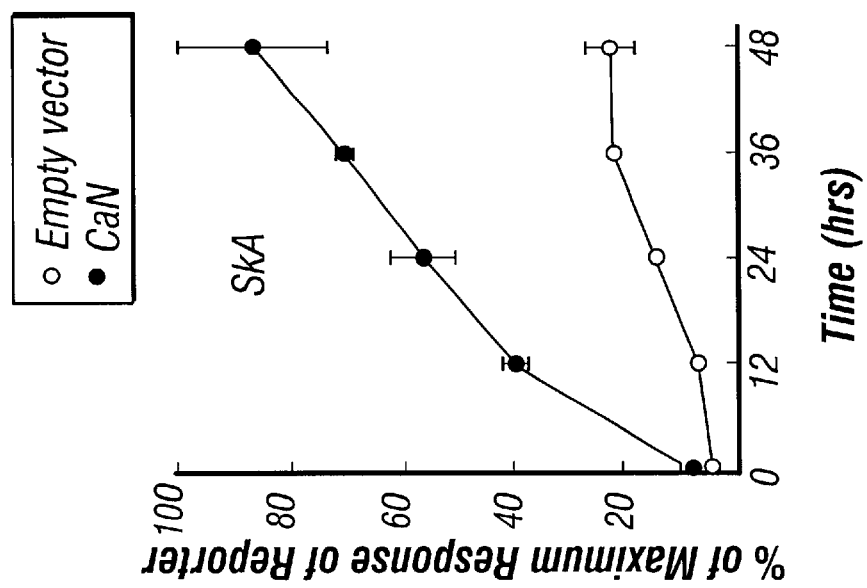
Figure 13B:
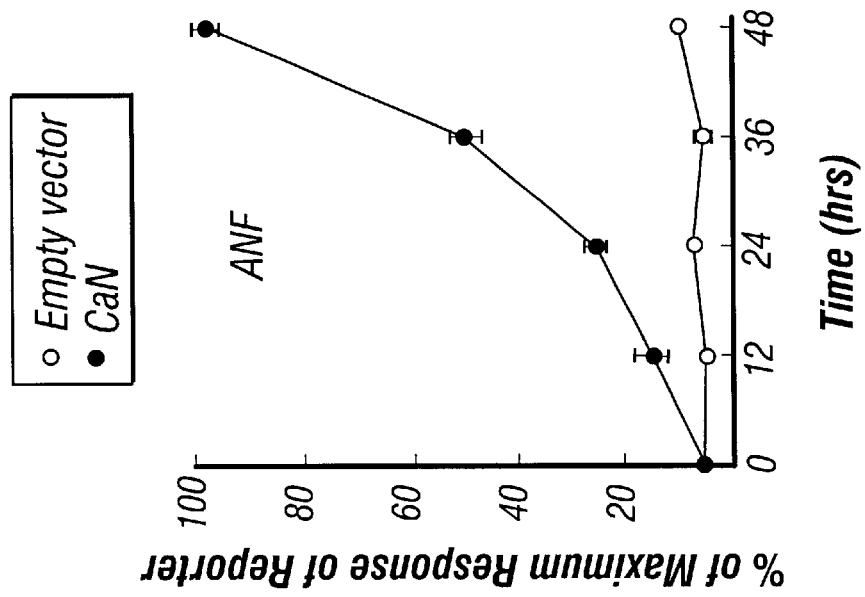

Induced Expression of an Active Form of Calcineurin Rapidly Activates the Transcription of Three Hypertrophy-sensitive Genes in Myocardial Cells To further assess the ability of calcineurin to regulate the cardiac gene expression in myocardial cells, we studied the time courses of expression of three hypertrophic response genes under the induction of active calcineurin expression. Cardiac α-actin, skeletal α-actin, and ANF promoter-Luc plasmids were used as reporters. Primary neonatal rat cardiomyocytes were co-transfected with either reporter, pUHD15-1, and p10-3CaN, or empty vector pUHD10-3 instead of p10-3CaN, together with pUHD15-1 and reporter plasmids. The amount of each plasmid was 0.25 μg. Transfections were carried out as described in Example 3. At various time points after transfection, the luciferase activities of cell extracts were measured, as described in Example 3. In each experiment, the highest level of luciferase activity was used as the maximum response of reporter gene, all data were normalized to a percentage of the maximum response. In the absence of the expression of exogenous active calcineurin, the transcription levels of three cardiac genes were very low. However, active calcineurin expression markedly induced the transcription of three cardiac genes, as shown in FIG. 13. The expression of cardiac α-actin, skeletal α-actin, and ANF genes were all significantly increased to nearly maximum levels 48 hours post-transfection, suggesting that active calcineurin rapidly activates the transcription of these hypertrophy response gene in primary cardiomyocytes.

Figure 14C:
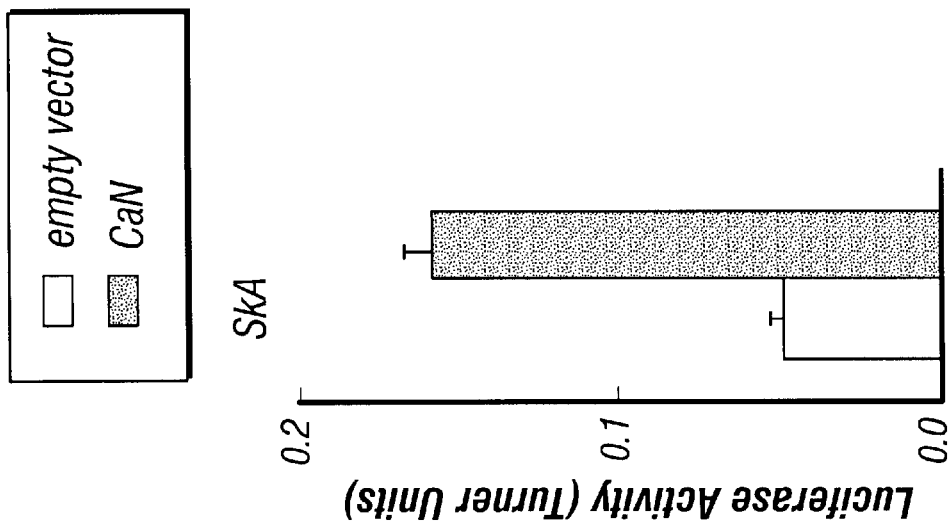
FIG. 14 presents bar graphs depicting effects of activated CaN on transcription of hypertrophy-sensitive genes in myocardial cells. Data are representative of three independent experiments. Values are reported as mean±SE; n=3 cultures.
Figure 14B:
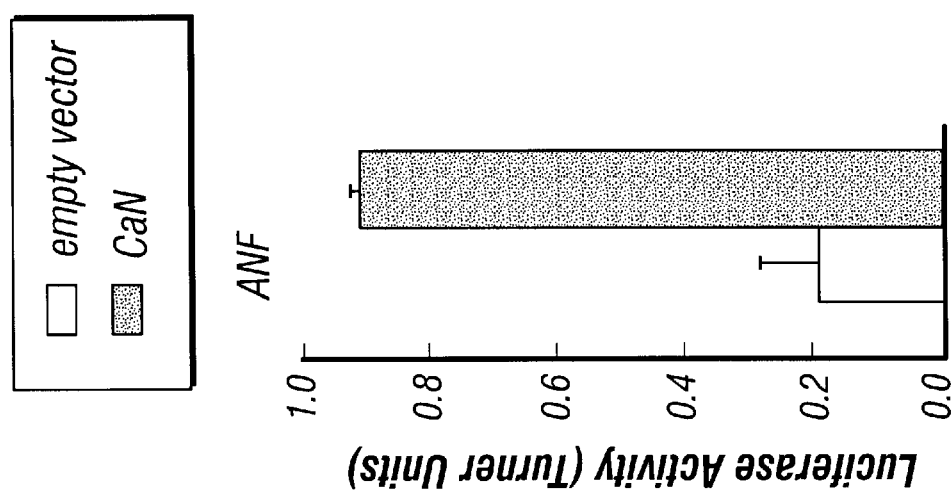
Figure 14A:
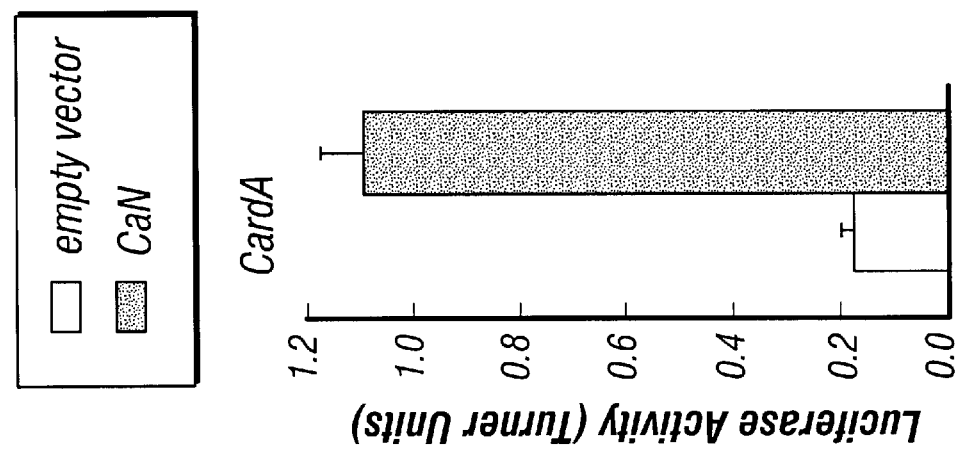

When the same cardiac cell preparations were co-transfected with same amounts of reporter, tTA, and calcineurin plasmid DNA as indicated in FIG. 14, expression levels of three cardiac genes were detected at 48 hours after transfection. Compared with the controls in which only empty vector pUHD10-3 instead of calcineurin plasmids, together with reporter and tTA plasmid, were transfected into the cardiomyocytes, calcineurin strongly activated the transcription of cardiac α-actin by about 8 to 10-fold, and moderately activated ANF and skeletal α-actin expression by about 6-fold and 3-fold, as shown in FIGS. 14B and 14C.

These results not only indicated the stimulatory effect of calcineurin on the transcription of hypertrophy-sensitive genes, but also demonstrated utility of the inducible gene expression system. The ability of activated calcineurin to induce the transcription of hypertrophy response gene in the cardiomyocytes is consistent with the result from transgenic mice overexpressing the constitutively active form of calcineurin (Molkentin et al., 1998). For example, the mRNA level of skeletal α-actin gene in the heart of calcineurin transgenic mice was about 5-fold higher than that in normal mouse heart The increased fold of ANF gene expression induced by calcineurin in our inducible expression system is similar to that of BNP gene activation in calcineurin transgenic mice. However, the increased fold in transcription level of cardiac α-actin gene in our system is higher than that in transgenic mice overexpressing calcineurin.

Figures 15, 16:
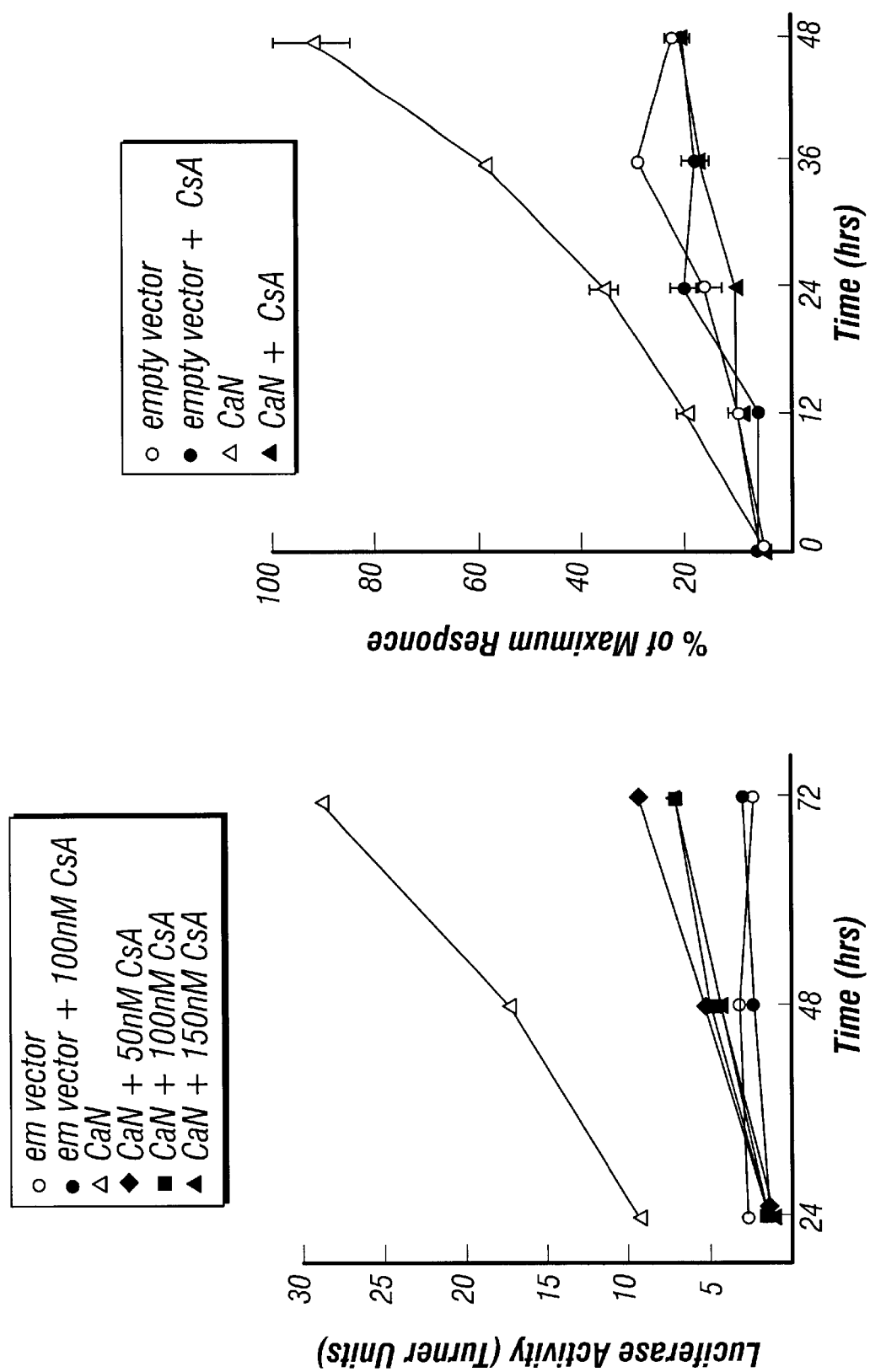
FIG. 15 is a graph depicting inhibition by CsA of CaN induction of cardiac hypertrophy response gene transcription. Myocardial cells were co-transfected with pUHDI 5-1, CardA-Luc, and either p10-3CaN or empty vector. Following transfection, cells were treated with 50 nM, 100 nM, or 150 nM CsA. At 24, 48, and 72 hours after treatment, luciferase activity was measured.
FIG. 16 is a graph showing a time course of CsA inhibition of CaN induction of transcription of a cardiac hypertrophy-sensitive gene. Values are reported as mean±SE; n=3 cultures.

Repression of Calcineurin Induction of Hypertrophic Response Gene Expression by Cyclosporin A To evaluate whether the transcriptional activation of hypertrophy-sensitive genes by activated calcineurin could be inhibited by CsA, a specific inhibitor of calcineurin, both the myocardial cell cultures transfected with either p10-3CaN construct or empty vector pUHD10-3, together with tTA and cardA-Luc reporter plasmids as described in Example 3, were treated with different concentrations of CsA (Sandoz Pharmaceuticals Corp., East Hanover, N.J.) or without CsA treatment from 0 hour after transfection. At various time points, the luciferase activities in those cells were assayed and compared. In the control group which had no calcineurin transfection, CsA treatment only resulted in a less decrease in the transcription level of cardiac α-actin gene compared with no treatment, as shown in FIG. 15. However, cardiac α-actin gene expression stimulated by activated calcineurin was significantly repressed by all those different concentrations of CsA, as shown in FIG. 15, further supporting the conclusion that the expression of these cardiac hypertrophic response gene is activated by a calcineurin-dependent signal transduction pathway. At 72 hours after transfection, cardiac α-actin gene activity induced by calcineurin was inhibited over 80% by 100 nM or 150 nM CsA treatment, as shown in FIG. 15, indicating that the very low concentrations of CsA can inhibit transcriptional activation of cardiac α-actin gene induced by calcineurin. Therefore, 100 nM was chosen as the optimal concentration of CsA in subsequent experiments.

To further demonstrate the effect of CsA on the transcription of hypertrophy-sensitive genes induced by calcineurin, we analyzed how the expression of cardiac α-actin promoter-reporter gene under active calcineurin stimulation responds to CsA. Primary cardiomyocytes were co-transfected with either tTA, cardiac α-actin reporter constructs, and calcineurin, or tTA, cardiac α-actin reporter gene and empty vector as the control. CsA treatment (100 nM) was initiated at 0 hour after transfection. Cardiac α-actin gene activity in cardiac cell cultures was examined by luciferase assay and results were normalized to a percentage of the maximum response. In the cells transfected with the empty vector, the expression of cardiac α-actin gene was low and there was no marked different in the gene activity between the CsA treated and untreated cells, as shown in FIG. 16. However, CsA treatment lead to a dramatic reduction in cardiac gene transcription in active calcineurin-transfected cells. 48 hours after CsA treatment, the expression of cardiac α-actin gene activated by calcineurin was decreased nearly to basal levels, as shown in FIG. 16.

Figure 17C:
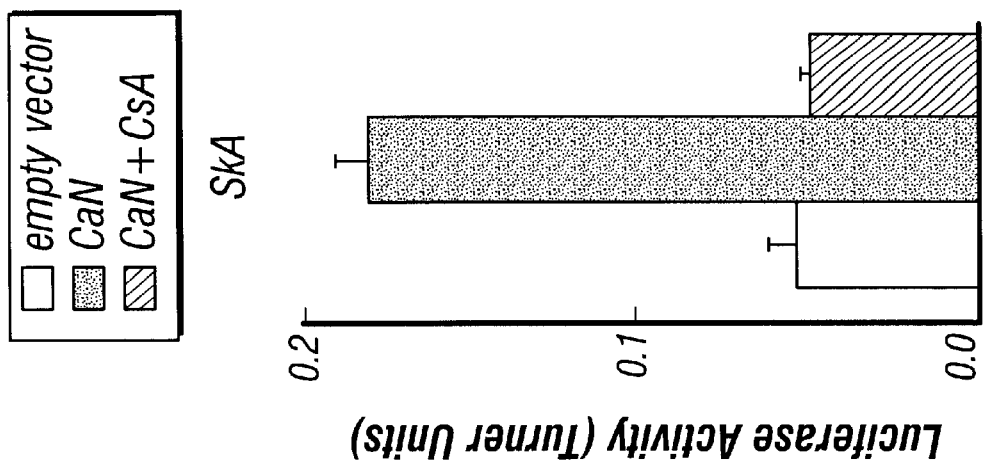
FIG. 17 is a bar graph depicting the effects of CsA treatment on transcriptional activation of cardiac hypertrophy-sensitive genes by CaN in myocardial cells. Values are reported as mean±SE; n=3 cultures.
Figure 17B:
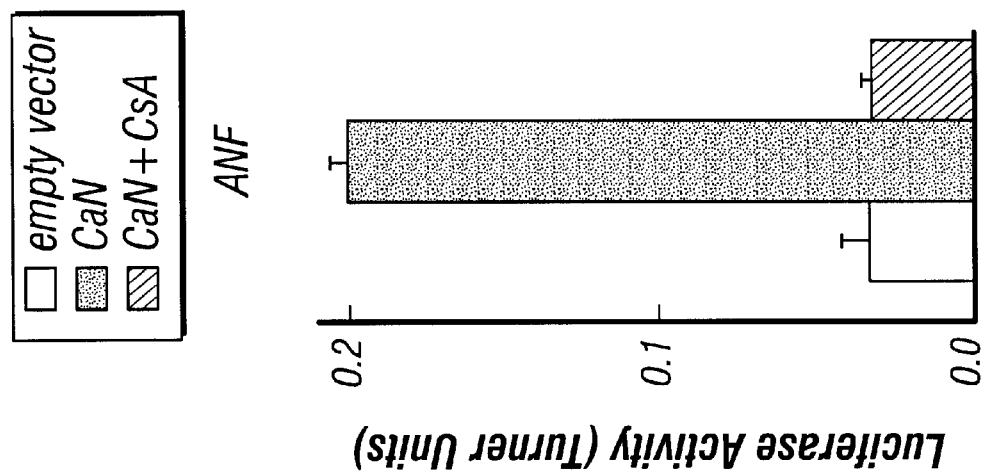
Figure 17A:
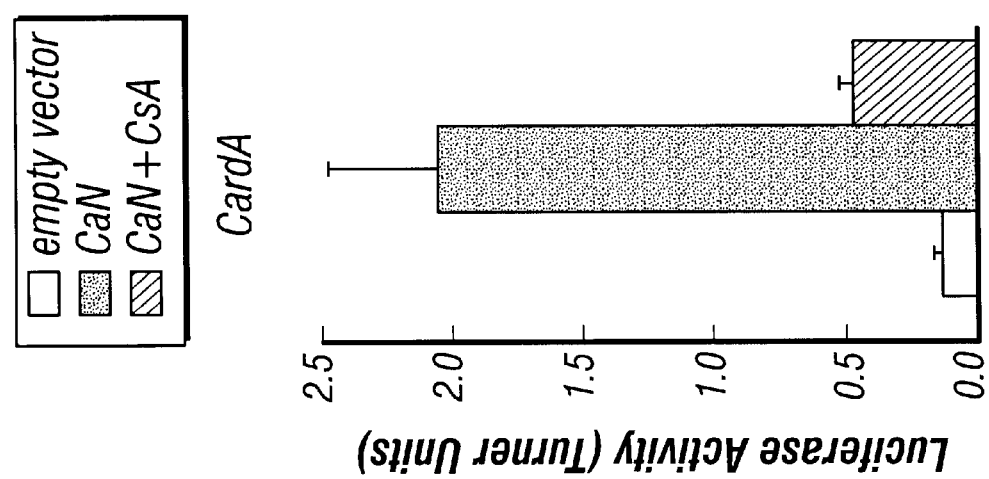

Based on the results above, we tested the effects of CsA on the calcineurin-mediated transcriptional activation of ANF, cardiac α-actin and skeletal α-actin genes. Equal amounts of each reporter construct, together with tTA and p10-3CaN DNA, were co-transfected into the cells derived from the same primary culture preparation. The empty vector, pUHD10-3, instead of p10-3CaN was used as a control. After transfection, the cells transfected with active calcineurin were cultured for 48 hours in either culture medium containing 100 nM CsA or in culture medium lacking CsA. Cells transfected with empty vector were cultured in medium lacking CsA for same amount of time. Then these cardiomyocytes were lysed to analyze the activities of these cardiac hypertrophy response genes. The results are shown in FIG. 17. The transcriptional activation of ANF and skeletal α-actin genes mediated by active calcineurin was almost completely blocked by CsA in primary rat cardiomyocytes: about 80% of transcriptional activity of cardiac α-actin gene up-regulated by the action of calcineurin was inhibited by CsA.

Figure 18:
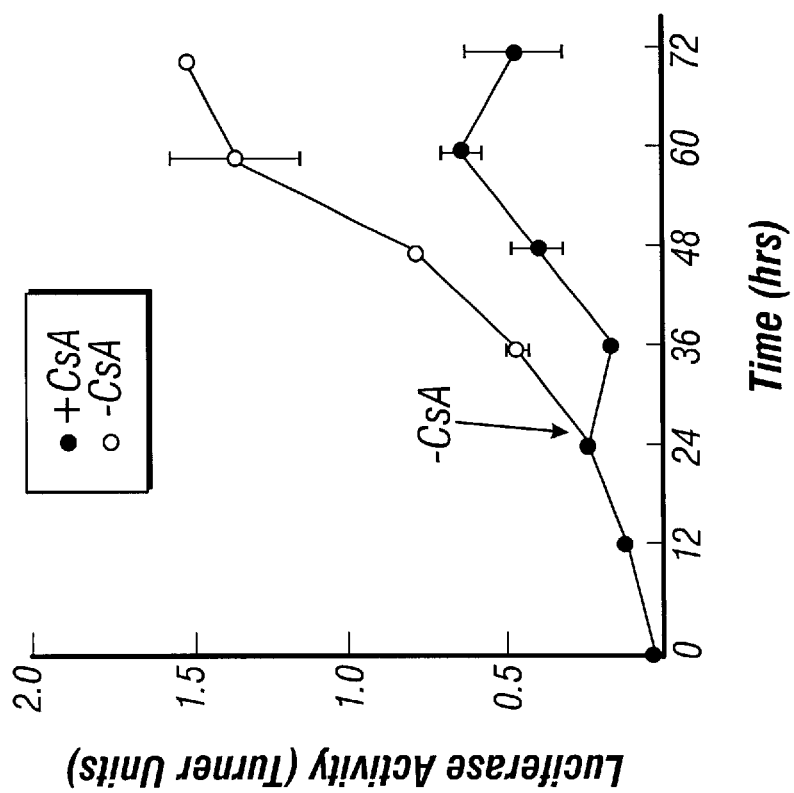
FIG. 18 is a graph showing reversible regulation of transcriptional repression of cardiac hypertrophy-response gene expression by CsA. Values are reported as mean±SE; n=3 cultures.

Repression of the Transcription of Hypertrophy-sensitive Genes by CsA Treatment is Reversible Due to practical requirements in complex studies, the ability to bidirectionally regulate the expression of exogenous gene would have a great significance in the studies of gene function as well as in gene therapies. To evaluate whether the repressed expression of the exogenous hypertrophic response genes in our system could be reversibly controlled by discontinuing CsA treatment, primary cardiomyocytes from the same preparation were transfected with tTA, calcineurin construct, and cardiac α-actin reporter plasmids. After transfection, all cells were treated with 100 nM CsA. 24 hours later, a portion of the cells were continuously cultured in CsA-containing medium, while another portion of the cells were switched to medium without CsA. At various time points, reporter gene expression in these cardiomyocytes was examined by luciferase assay. As shown in FIG. 18, during a 72-hour period, the reporter gene activities in CsA-treated cells were low. However, the expression of the cardiac gene was rapidly elevated after discontinuing CsA treatment. 48 hours after removing CsA from media (72 hour time point), cardiac α-actin reporter gene activity had increased about 2.5-fold compared with that in cells treated with CsA. The data demonstrated that the repressed transcription of the cardiac gene by CsA could be rapidly reversed. Therefore, based on these results shown above, the expression of exogenous hypertrophy-sensitive genes in primary cardiomyocytes, under the experimental conditions used, could be rapidly regulated in either a positive or a negative way.

EXAMPLE 5

Characterization of Effects of CaMKIV and YY1 on Expression of Hypertrophy-sensitive Genes in a Cultured Cardiomyocyte Cell Model Experimental procedures with respect to cardiomyocyte cell culture, cardiomyocyte transient transfections, and luciferase activity measurements were carried out as described in Example 3. Cardiac hypertrophy-sensitive promoter-reporter constructs are as described in Example 3.

Results

Figure 19:
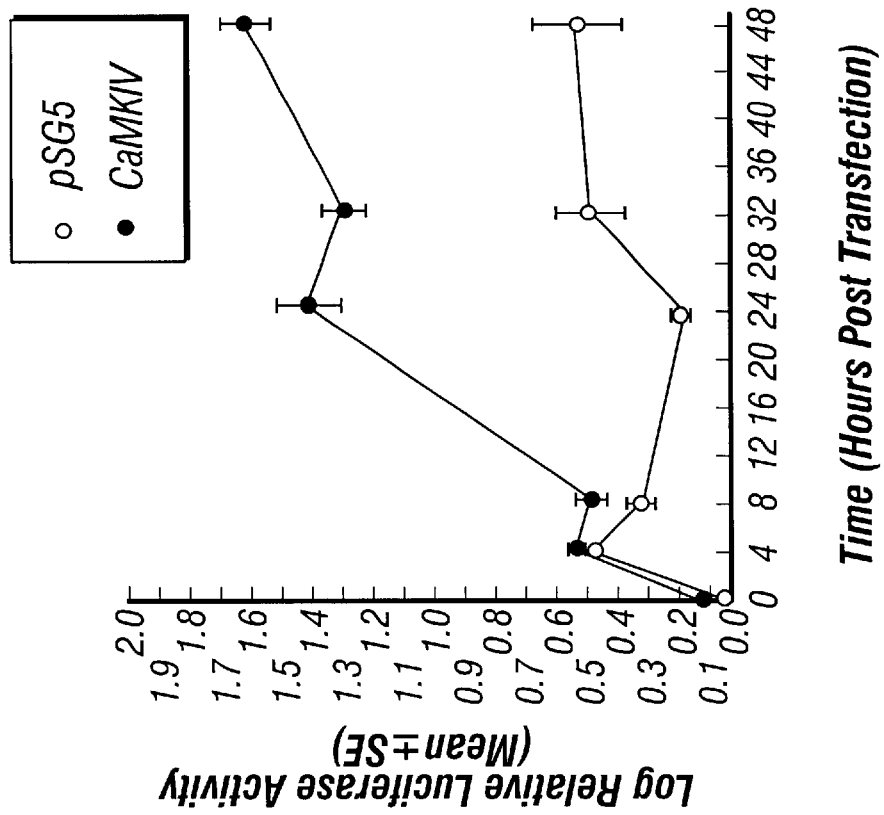
FIG. 19 is a graph showing time-dependent response of constitutively-active CaMKIV on skeletal α-actin promoter-reporter activity in rat neonate cardiomyocytes.

Constitutively active CaMKIV increases transcription of cardiac hypertrophy-sensitive gene promoter-reporter activity in neonate cardiomyocytes A cDNA encoding a constitutively active form of CaMKIV, as described above, was inserted into an expression vector containing the α-MHC promoter. Neonate cardiomyocytes were co-transfected with skeletal α-actin-luciferase plasmid described in Example 3 and a constitutively active mutant form of CaMKIV in an expression plasmid. pSG (empty vector) served as a negative control. Luciferase activity was measured at various times after transfection. The results are shown in FIG. 19. Over-expression of constitutively active exogenous CaMKIV increased skeletal α-actin promoter activity more than 300% over controls.

Figure 20:
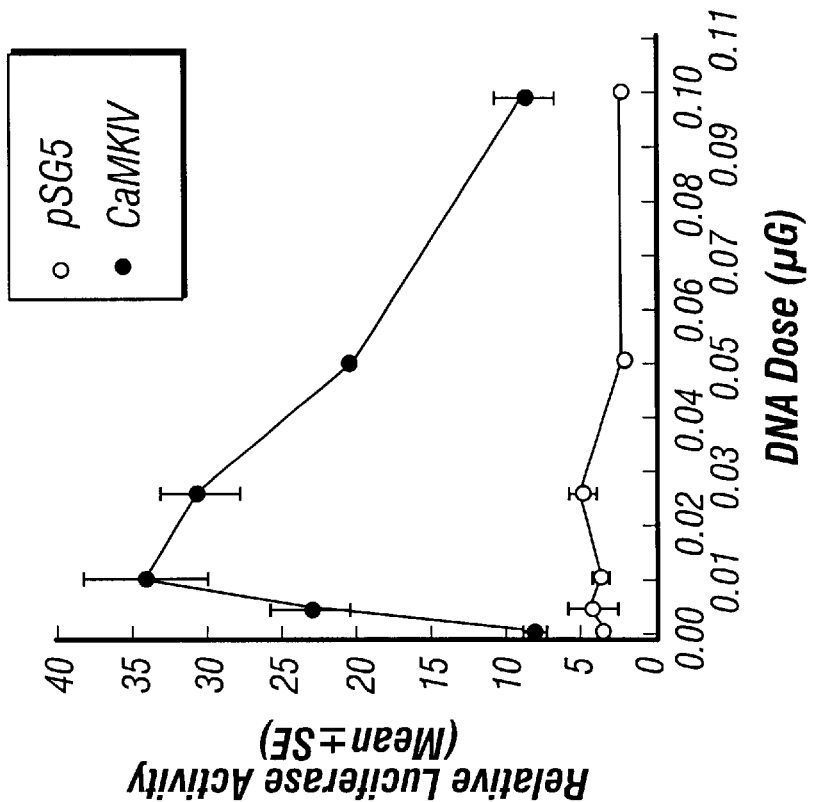
FIG. 20 is a graph showing dose-dependent response of constitutively active CaMKIV on cardiac α-actin promoter-reporter activity in rat neonate cardiomyocytes.

The effect of overexpression of constitutively active exogenous CaMKIV on a cardiac α-actin promoter-reporter construct in neonate cardiomyocytes was explored. Cardiomyocytes were co-transfected with a cardiac α-actin promoter-reporter construct as described in Example 3, and various amounts of the expression plasmid encoding constitutively active CaMKIV. The results, shown in FIG. 20, indicate that over-expression of constitutively active CaMKIV results in modest increases in cardiac α-actin promoter activity. Peak induction (about 7-fold over control) was achieved using 0.01 μg CaMKIV expression plasmid, and dropped to nearly control levels when 0.10 μg CaMKIV expression plasmid was used.

Figure 21:
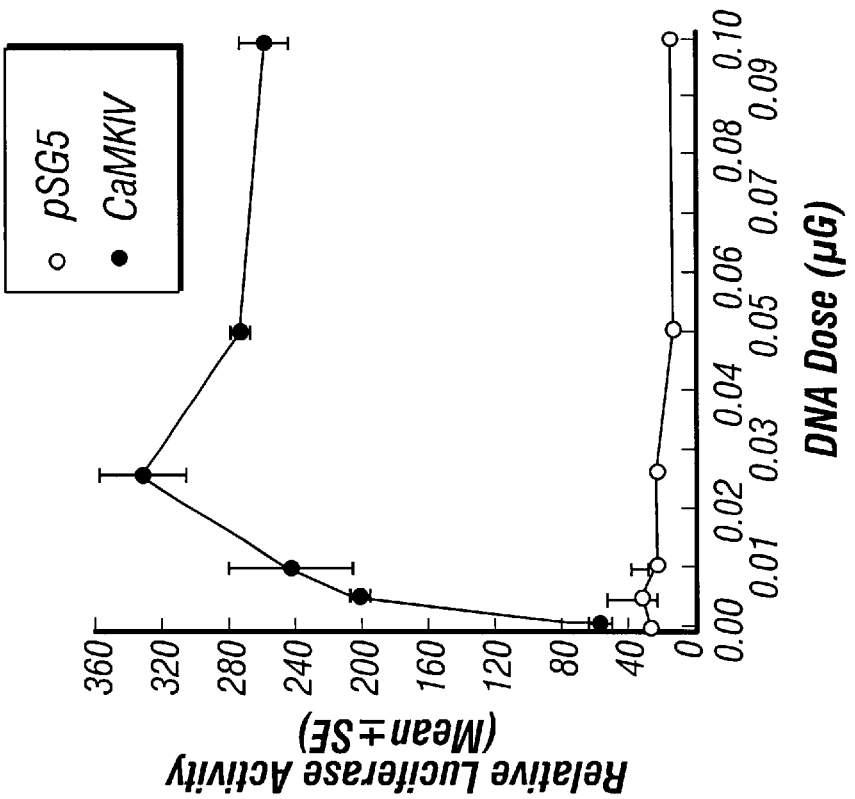
FIG. 21 is a graph showing dose-dependent response of constitutively active CaMKIV on skeletal α-actin promoter-reporter activity in rat neonate cardiomyocytes.
Figure 22:
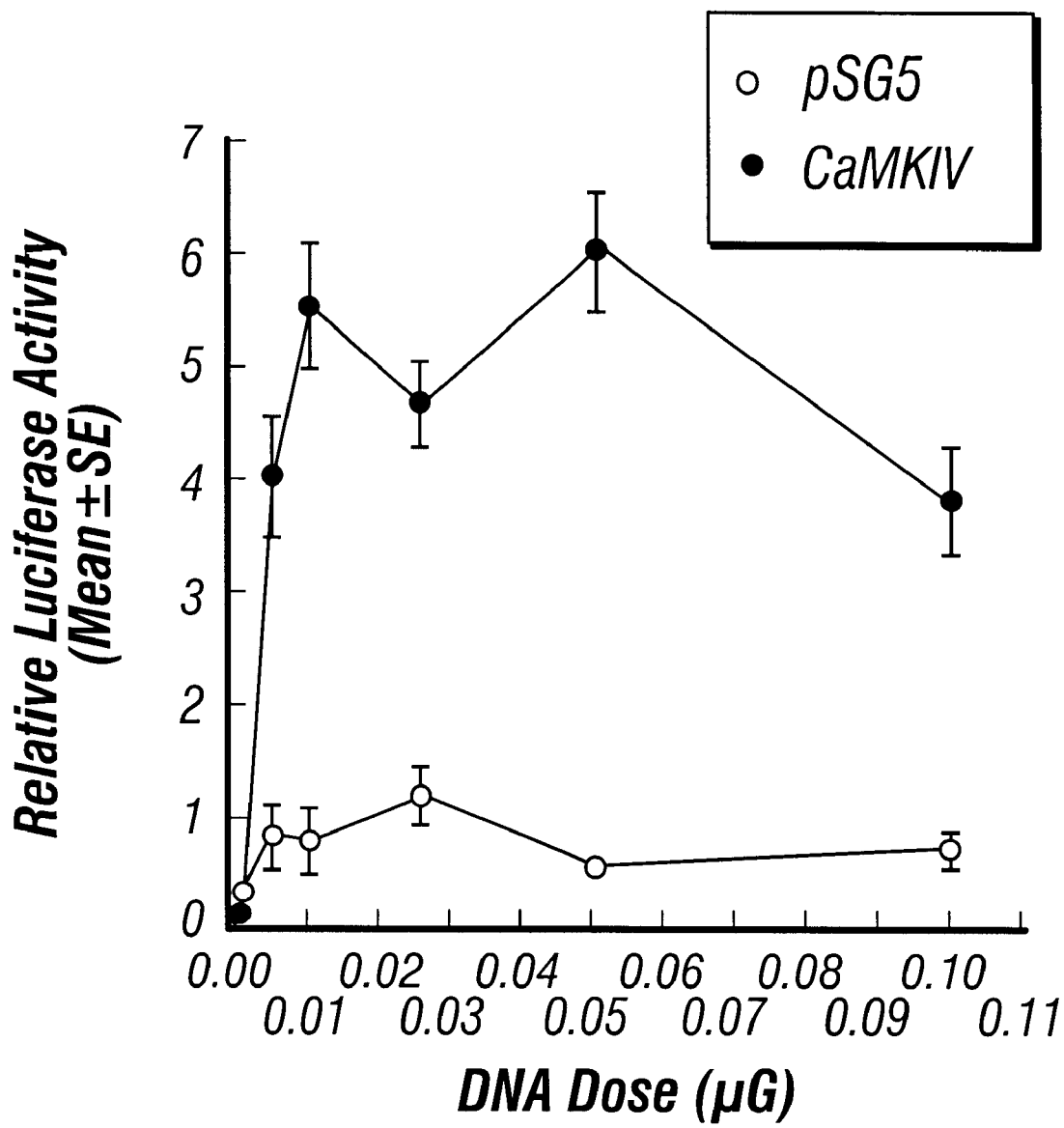
FIG. 22 is a graph showing dose-dependent response of constitutively active CaMKIV on ANF promoter-reporter activity in rat neonate cardiomyocytes.

In contrast, when a similar dose-dependence study was performed using skeletal α-actin promoter-reporter plasmid, over-expression of constitutively active CaMKIV resulted in substantial increases in skeletal α-actin promoter activity, as shown in FIG. 21. A similar result was observed using an ANF promoter-reporter construct, as shown in FIG. 22.

All publications and patent applications mentioned in this specification are herein incorporated by reference to the same extent as if each individual publication or patent application was specifically and individually indicated to be incorporated by reference.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

wherein the expression of calcineurin, CaMKIV, or a functional fragment of calcineurin or CaMKIV in said transgenic mouse results in an increased probability of spontaneously developing cardiac hypertrophy when compared to a non-transgenic littermate.

2. The transgenic mouse according to claim 1, wherein the promoter is an α-myosin heavy chain promoter.

3. The transgenic mouse according to claim 1, wherein the coding region encodes calcineurin or a functional fragment thereof.

4. The transgenic mouse according to claim 3, wherein a phosphatase activity of the calcineurin is constitutively activated.

5. A cardiomyocyte isolated from the transgenic mouse of claim 1.

6. The transgenic mouse according to claim 1, wherein the coding region encodes calcium calmodulin dependent kinase IV (CaMKIV).

7. The transgenic mouse according to claim 1, wherein the coding region encodes calcineurin.

8. The transgenic mouse according to claim 1, wherein the coding region encodes calcium calmodulin dependent Kinase IV (CaMKIV) or a functional fragment thereof.

9. A method of making a transgenic mouse comprising:
a) introducing into a mouse embryo a polynucleotide comprising a coding region which encodes a gene product selected from the group consisting of calcineurin, calcium calmodulin dependent kinase IV (CaMKIV), a functional fragment of calcineurin, and a functional fragment of CAMKIV, said coding region being operably linked to a transcriptional regulatory element (TRE) comprising a promoter preferentially active in cardiomyocytes;
b) transferring the embryo into a foster mother mouse;
c) permitting the embryo to gestate; and
d) selecting a transgenic mouse born to said foster mother mouse,
wherein said transgenic mouse is characterized in that it has an increased probability of spontaneously devel-

What is claimed is:

1. A transgenic mouse having a genome comprising a transgene which comprises:

a) a coding region which encodes calcineurin, calcium calmodulin dependent kinase IV (CaMKIV), or a functional fragment of calcineurin or CaMKIV; and b) a transcriptional control element (TRE) operably linked to said coding region, wherein said TRE comprises a promoter preferentially active in cardiomyocytes, oping cardiac hypertrophy when compared to a non-transgenic littermate.

10. The method of claim 9, wherein said gene is calcineurin or a functional fragment thereof.

11. The method according to claim 9, wherein the promoter is an α-myosin heavy chain promoter.

12. The method of claim 9, wherein said gene is calcium calmodulin dependent kinase IV (CaMKIV) or a functional fragment thereof.

13. A method for screening a substance for the ability to reduce cardiac hypertrophy comprising:

a) administering the substance to the transgenic mouse of claim 1;

b) measuring a cardiac hypertrophy parameter in the mouse of step (a)

c) comparing the measurement obtained in step (b) to that of a transgenic littermate not administered the substance, wherein the measurement of the cardiac hypertrophy parameter in the mouse of step (a) is consistent with a reduction in cardiac hypertrophy.

14. The method according to claim 13, wherein the cardiac hypertrophy parameter is expression of a gene selected from the group consisting of an atrial natriuretic factor gene, a b-type natriuretic peptide gene, a β-myosin heavy chain gene, and an α-skeletal actin gene.

15. The method according to claim 13, wherein the promoter is an α-myosin heavy chain promoter.

16. The method according to claim 13, wherein the coding region encodes calcineurin.

17. The method according to claim 13, wherein the coding region encodes calcium calmodulin dependent kinase IV (CaMKIV).

18. The method of claim 13, wherein the coding region encodes calcineurin or a functional fragment thereof.

19. The method of claim 13, wherein the coding region encodes calcium calmodulin dependent kinase IV (CaMKIV) or a functional fragment thereof.

* * * * *